United States Patent
Nishimura et al.

(10) Patent No.: US 6,410,576 B1
(45) Date of Patent: Jun. 25, 2002

(54) THIAZOLIDINE DERIVATIVES

(75) Inventors: Kazuo Nishimura; Ken-ichi Fujimura, both of Osaka; Junzo Matsumoto, deceased, late of Ashiya, by Eiko Matsumoto legal representative; Tadayuki Kobayashi, Osaka, all of (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/744,710

(22) PCT Filed: Jul. 27, 1999

(86) PCT No.: PCT/JP99/04017

§ 371 (c)(1),
(2), (4) Date: Jan. 29, 2001

(87) PCT Pub. No.: WO00/06594

PCT Pub. Date: Feb. 10, 2000

(30) Foreign Application Priority Data

Jul. 28, 1998 (JP) ............................ 10-212368

(51) Int. Cl.$^7$ ............. A61K 31/425; A61K 31/445; A61K 31/495; C07D 277/04; C07D 401/00
(52) U.S. Cl. ............. 514/365; 514/397; 514/326; 514/254.04; 514/386; 548/200; 548/311.1; 546/209; 544/367
(58) Field of Search ............. 548/200, 311.1; 546/209; 544/367; 514/365, 397, 326, 254.04, 386

(56) References Cited

U.S. PATENT DOCUMENTS

| | | | |
|---|---|---|---|
| 4,425,333 A | 1/1984 | Iwao et al. | 424/177 |
| 5,773,455 A | * 6/1998 | Dong et al. | 514/365 |

FOREIGN PATENT DOCUMENTS

| | | |
|---|---|---|
| JP | 56-49373 A | 5/1981 |
| JP | 56-139455 A | 10/1981 |
| JP | 1-143897 A | 6/1989 |
| JP | 9-124691 A | 5/1997 |
| WO | WO-98/00409 | * 1/1988 |

OTHER PUBLICATIONS

Cregge et al. Inhibition of human neutrophil elastage. 4. Design, synthesis, X-ray . . . peptidyl pentafluoroethyl ketones. J. Med. Chem. vol. 41, pp. 2461–2480; Pub date: Jun. 3, 1988.*

Streitwieser et al. Introduction to Organic Chemistry, 2nd Edn., pp. 390, 752, 785, and 786; Pub year: 1976; Macmilan Publishing Company, New York; ISBN 0–02–97810–8 (International Edition).*

Bogert et al. Synthesis and antitrypanosomal evaluation of some thiazole–containing amino acids and peptides. Eur. J. Med. Chem. vol. 28, pp. 387–397; Pub year: 1993.*

G.M. Rishton et al, "Aβ–turn mimic and a thiomethylene dipeptide surrogate employed in the study of cyclic peptide RGD and RCD cell–adhesion inhibitors", *Letters in Peptide Science*, vol. 3, pp. 37–44 (1996).

* cited by examiner

*Primary Examiner*—Mukund J. Shah
*Assistant Examiner*—Sudhaker B. Patel
(74) *Attorney, Agent, or Firm*—Frishauf, Holtz, Goodman & Chick, P.C.

(57) ABSTRACT

An object of the present invention is to provide novel thiazolidine derivatives which are useful as drugs. The thiazolidine derivatives according to the present invention are compounds represented by the following general formula [I] and salts thereof,

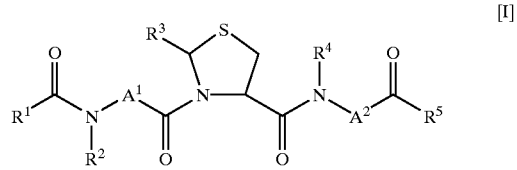

wherein $R^1$ is alkyl, hydroxy, alkoxy, alkoxyalkyl, phenyl, phenylalkyl, phenylalkoxy, phenoxy, phenoxyalkyl, amino, alkylamino or a nonaromatic heterocycle; $R^2$ is H or alkyl; $R^3$ is H, alkyl or phenyl; $R^4$ is H or alkyl; $R^5$ is alkyl, halogenoalkyl, hydroxy, alkoxy, phenyl, phenylalkoxy, phenoxy, carboxyl, alkoxycarbonyl, phenylalkoxycarbonyl or an aromatic heterocycle; $A^1$ is alkylene; and $A^2$ is alkylene.

12 Claims, No Drawings

THIAZOLIDINE DERIVATIVES

CROSS REFERENCE TO RELATED APPLICATION

This application is the United States National Phase Application under 35 USC 371 of International Application PCT/JP99/04017 (not published in English) filed Jul. 27, 1999.

TECHNICAL FIELD

The present invention relates to novel thiazolidine derivatives which are useful as drugs such as chymase inhibitors.

BACKGROUND ART

Compounds having a thiazolidine ring as a main skeleton is known to be useful for various drugs, and many derivatives thereof have also been synthesized. Main synthesis studies are as follows; a study of converting 4-thiazolidinecarboxylic acid, which can be synthesized easily, into amide compounds; and a study of introducing various substituents into the nitrogen atom at the 3rd-position through a carbonyl linkage. For example, it was reported that carboxylic acid derivatives were further introduced into the amide linkage at the 4th-position through an alkylene chain (see Japanese Laid-open Patent Publication No. 49373/1981 and Japanese Laid-open Patent Publication No. 139455/1981). Many studies were also reported wherein the various substituents are introduced into the nitrogen at the 3rd-position through the carbonyl linkage. However, compounds wherein the nitrogen atom joins with the carbonyl through an alkylene chain have scarcely been studied.

There are still many unknown compounds in the compounds having a thiazolidine ring as the main skeleton, and preparation of novel compounds and a study of their pharmacological actions are very interesting subjects.

DISCLOSURE OF THE INVENTION

The present inventors studied preparation of various novel compounds derived from 4-thiazolidinecarboxylic acid. They focused attention on synthesis of novel compounds wherein 1) the carboxyl group at the 4th-position is amidated and the resulting amide moiety is substituted by substituents having a carbonyl group through an alkylene chain, and further 2) various substituents are introduced into the nitrogen atom at the 3rd-position through a carbonyl group. In particular, their efforts were focused on selection of substituents joining with the carbonyl group through an alkylene chain as the substituents introduced into the nitrogen atom at the 3rd-position through the carbonyl group. As a result, the present inventors succeeded in preparing many novel compounds as mentioned later. Studying their pharmacological actions, these novel compounds were found to have chymase inhibitory actions and to be useful as drugs. In a process of the synthesis of the above-mentioned novel thiazolidine derivatives, the present inventors succeeded also in preparing novel compounds which are useful as synthetic intermediates of the derivatives.

The present invention relates to compounds represented by the following general formula [I] and salts thereof (hereinafter referred to as "the present compounds" as far as there is no proviso), pharmaceutical compositions containing the present compound or the salt thereof as an active ingredient, and compounds which are represented by the following general formula [II] and are useful as synthetic intermediates of the present compounds and salts thereof (hereinafter referred to as "the present synthetic intermediates" as far as there is no proviso).

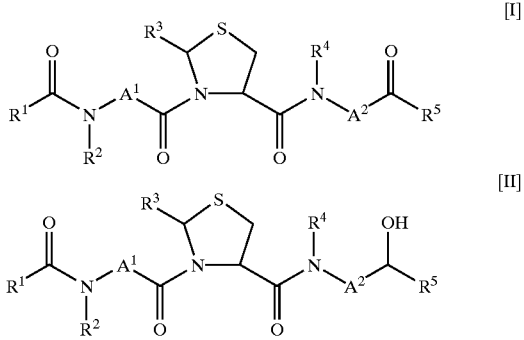

wherein $R^1$ is lower alkyl, hydroxy, lower alkoxy, lower alkoxy-lower alkyl, phenyl, phenyl-lower alkyl, phenyl-lower alkoxy, phenoxy, phenoxy-lower alkyl, amino, lower alkylamino or a nonaromatic heterocycle.

$R^2$ is hydrogen or lower alkyl, and $R^2$ can join with $A^1$ through carbon or sulfur to form a nonaromatic heterocycle.

$R^3$ is hydrogen, lower alkyl or phenyl, and $R^3$ can join with $A^1$ through carbon to form a nonaromatic heterocycle.

$R^4$ is hydrogen or lower alkyl.

$R^5$ is lower alkyl, halogeno-lower alkyl, hydroxy, lower alkoxy, phenyl, phenyl-lower alkoxy, phenoxy, carboxyl, lower alkoxy-carbonyl, phenyl-lower alkoxycarbonyl or an aromatic heterocycle.

$A^1$ is lower alkylene, wherein the lower alkylene can be substituted by hydroxy, lower alkoxy, phenyl, phenoxy, carboxyl, lower alkoxycarbonyl, phenyl-lower alkoxycarbonyl or an aromatic heterocycle.

$A^2$ is lower alkylene, wherein the lower alkylene can be substituted by phenyl.

Each nonaromatic heterocycle defined above can be substituted by lower alkyl, phenyl, phenyl-lower alkyl, amino, lower alkylamino or phenyl-lower alkylamino.

Each phenyl ring of phenyl, phenyl-lower alkyl, phenyl-lower alkoxy, phenoxy, phenoxy-lower alkyl and phenyl-lower alkoxycarbonyl defined above can be substituted by halogen, lower alkyl, hydroxy, lower alkoxy, phenyl, phenoxy, carboxyl, lower alkoxycarbonyl, amino, lower alkylamino, nitro or cyano.

Each lower alkyl moiety of lower alkylamino defined above can be substituted by phenyl, amino or lower alkylamino. The same definitions are applied hereinafter.

The groups defined above are hereinafter described in detail.

The halogen is fluorine, chlorine, bromine or iodine.

The lower alkyl is straight-chain or branched alkyl having one to six carbon atoms such as methyl, ethyl, propyl, butyl, pentyl, hexyl, isopropyl, isobutyl, sec-butyl or tert-butyl.

The lower alkoxy is straight-chain or branched alkoxy having one to six carbon atoms such as methoxy, ethoxy, propoxy, butoxy, hexyloxy, isopropoxy or tert-butoxy.

The lower alkylene is straight-chain or branched alkylene having one to six carbon atoms such as methylene, ethylene, trimethylene, tetramethylene, pentamethylene, hexamethylene, methylmethylene, dimethylmethylene, ethylmethylene, propylmethylene, isopropylmethylene, butylmethylene, isobutylmethylene, sec-butylmethylene, tert-butylmethylene, dimethylethylene, ethylethylene, propylethylene, isopropylethylene, methyltrimethylene or propylene.

The nonaromatic heterocycle is a nonaromatic heterocycle selected from pyrrolidine, piperidine, homopiperidine, octahydroazocine, pyrroline, piperazine, imidazolidine, imidazoline, pyrazolidine, pyrazoline, oxazolidine, thiazolidine and the like.

The aromatic heterocycle is an aromatic heterocycle selected from pyrrole, indole, isoindole, imidazole, pyrazole, oxazole, isoxazole, benzoxazole, thiazole, isothiazole, benzothiazole, pyridine, quinoline, pyrazine and the like.

The lower alkylamino is mono- or di-lower alkylamino.

Nitrogen atom of the above-mentioned amino, lower alkylamino, nonaromatic heterocycle or aromatic heterocycle can be protected with a protecting group. This protecting group can be a general protecting group of nitrogen atom of amino, lower alkylamino, a nonaromatic heterocycle or an aromatic heterocycle, such as acyl, substituted lower alkyl or substituted sulfonyl.

In detail, examples of the protecting group are acyl such as formyl, lower alkanoyl, halogeno-lower alkanoyl, lower alkoxycarbonyl, halogeno-lower alkoxycarbonyl, phenylcarbonyl, phenyl-lower alkoxycarbonyl or phenoxycarbonyl, substituted alkyl such as phenyl-lower alkyl, phenyl-lower alkoxy-lower alkyl or trityl, and substituted sulfonyl such as lower alkylsulfonyl or phenylsulfonyl. Each phenyl ring of the phenylcarbonyl, the phenyl-lower alkoxycarbonyl, the phenoxycarbonyl, the phenyl-lower alkyl, the phenyl-lower alkoxy-lower alkyl, the trityl and the phenylsulfonyl can be substituted by halogen, lower alkyl, lower alkoxy or nitro.

Specific examples of the protecting group are acyl such as formyl, acetyl, trichloroacetyl, trifluoroacetyl, methoxycarbonyl, isobutoxycarbonyl, tert-butoxycarbonyl, 2,2,2-trichloroethoxycarbonyl, benzoyl, benzyloxycarbonyl, 4-bromobenzyloxycarbonyl, 2,4,6-trimethylbenzyloxycarbonyl, 4-methoxybenzyloxycarbonyl, 4-nitrobenzyloxycarbonyl or phenoxycarbonyl, substituted alkyl such as benzyl, 2-nitrobenzyl, benzyloxymethyl or trityl, and substituted sulfonyl such as methanesulfonyl, benzenesulfonyl or toluenesulfonyl.

Salts in the present invention refer to any pharmaceutically acceptable salts. Examples thereof are salts with an inorganic acid such as hydrochloric acid, nitric acid or sulfuric acid, salts with an organic acid such as acetic acid, fumaric acid, maleic acid or tartaric acid, salts with an alkali metal or an alkaline-earth metal such as sodium, potassium or calcium, and the like. When the present compounds or the present intermediates have asymmetric carbon atoms and geometrical isomers or optical isomers are present in the present compounds or the present intermediates, these isomers are also included in the scope of the present invention. The present compounds or the present intermediates can be in the form of solvates such as hydrates.

Preferred examples of the present compound are compounds wherein the group(s) is (are) the followings in the compounds represented by the general formula [I] or salts thereof;

(1a) $R^1$ is a group selected from lower alkyl, hydroxy, lower alkoxy, lower alkoxy-lower alkyl, phenyl, phenyl-lower alkyl, phenyl-lower alkoxy, phenoxy, phenoxy-lower alkyl, amino, lower alkylamino, piperidine and piperazine, wherein each phenyl ring of phenyl, phenyl-lower alkyl, phenyl-lower alkoxy, phenoxy or phenoxy-lower alkyl defined above can be substituted by halogen or a group selected from lower alkyl, Lower alkoxy and nitro, the lower alkyl moiety of the lower alkylamino can be substituted by a group selected from phenyl and amino, and the piperidine or the piperazine can be substituted by a group selected from lower alkyl and lower alkylamino; and/or (2a) $R^2$ is hydrogen or lower alkyl; and/or (3a) $R^2$ is a group joining with $A^1$ through carbon or sulfur to form a ring selected from pyrrolidine and thiazolidine; and/or (4a) $R^3$ is hydrogen or phenyl, wherein the phenyl can be substituted by halogen or a group selected from lower alkyl, lower alkoxy and nitro; and/or (5a) $R^3$ is a group joining with $A^1$ through carbon to form a ring selected from pyrrolidine, piperidine, homopiperazine and octahydroazocine; and/or (6a) $R^4$ is hydrogen; and/or (7a) $R^5$ is a group selected from lower alkyl, halogeno-lower alkyl, lower alkoxycarbonyl, phenyl-lower alkoxycarbonyl, oxazole, benzoxazole, thiazole and benzothiazole; and/or (8a) $A^1$ is lower alkylene which can be substituted by a group selected from hydroxy, lower alkoxy, phenyl, carboxyl, lower alkoxycarbonyl, indole and imidazole; and/or (9a) $A^2$ is lower alkylene which can be substituted by phenyl.

Namely,
Compounds defined by above (1a) in the compounds represented by the general formula [I],
Compounds defined by above (2a) in the compounds represented by the general formula [I],
Compounds defined by above (3a) in the compounds represented by the general formula [I],
Compounds defined by above (4a) in the compounds represented by the general formula [I],
Compounds defined by above (5a) in the compounds represented by the general formula [I],
Compounds defined by above (6a) in the compounds represented by the general formula [I],
Compounds defined by above (7a) in the compounds represented by the general formula [I],
Compounds defined by above (8 a) in the compounds represented by the general formula [I],
Compounds defined by above (9a) in the compounds represented by the general formula [I], and
Compounds defined by any combinations of two or more of above (1a), (2a), (3a), (4a), (5a), (6a), (7a), (8a) and (9a) in the compounds represented by the general formula [I].

More preferred examples of the present compound are compounds wherein the group(s) is (are) the followings in the compounds represented by the general formula [I] or salts thereof; (1b) $R^1$ is a group selected from lower alkoxy, lower alkoxy-lower alkyl, phenyl-lower alkoxy, phenoxy-lower alkyl, lower alkylamino and piperidine, wherein the phenyl ring of the phenyl-lower alkoxy can be substituted by lower alkoxy, the lower alkyl moiety of the lower alkylamino can be substituted by phenyl or amino, and the piperidine can be substituted by lower alkylamino; and/or (2b) $R^2$ is hydrogen; and/or (3b) $R^2$ is a group joining with $A^1$ through carbon to form pyrrolidine; and/or (4b) $R^3$ is hydrogen or phenyl; and/or (5b) $R^3$ is a group joining with $A^1$ through carbon to form a ring selected from piperidine and homopiperazine; and/or (6b) $R^4$ is hydrogen; and/or
(7b) $R^5$ is lower alkoxycarbonyl or phenyl-lower alkoxycarbonyl; and/or
(8b) $A^1$ is lower alkylene which can be substituted by hydroxy or indole; and/or
(9b) $A^2$ is lower alkylene which can be substituted by phenyl.

Namely,
  Compounds defined by above (1b) in the compounds represented by the general formula [I] and salts thereof,
  Compounds defined by above (2b) in the compounds represented by the general formula [I] and salts thereof,
  Compounds defined by above (3b) in the compounds represented by the general formula [I] and salts thereof,
  Compounds defined by above (4b) in the compounds represented by the general formula [I] and salts thereof,
  Compounds defined by above (5b) in the compounds represented by the general formula [I] and salts thereof,
  Compounds defined by above (6b) in the compounds represented by the general formula [I] and salts thereof,
  Compounds defined by above (7b) in the compounds represented by the general formula [I] and salts thereof,
  Compounds defined by above (8b) in the compounds represented by the general formula [I] and salts thereof,
  Compounds defined by above (9b) in the compounds represented by the general formula [I] and salts thereof, and
  Compounds defined by any combinations of two or more of above (1b), (2b), (3b), (4b), (5b), (6b), (7b), (8b) and (9b) in the compounds represented by the general formula [I] and salts thereof.

Further preferred examples of the present compound are compounds wherein the group(s) is (are) the followings in the compounds represented by the general formula [I] or salts thereof;

(1c) $R^1$ is a group selected from methyl, tert-butoxy, methoxymethyl, phenylmethyl, phenylethyl, phenylmethoxy, (4-chlorophenyl)methoxy, (4-methylphenyl)methoxy, (4-methoxyphenyl) methoxy, (4-nitrophenyl)methoxy, phenoxy, phenoxymethyl, ethylmethylamino, N-methyl-N-phenylmethylamino, N-(2-aminoethyl)-N-methylamino, 4-(methylamino)piperidino and 4-methylpiperazino; and/or
(2c) $R^2$ is hydrogen or methyl; and/or
(3c) $R^2$ is a group joining with $A^1$ through carbon or sulfur to form a ring selected from pyrrolidine and thiazolidine; and/or
(4c) $R^3$ is a group selected from hydrogen, phenyl, 4-chlorophenyl, 4-methylphenyl,4-methoxyphenyl and 4-nitrophenyl; and/or
(5c) $R^3$ is a group joining with $A^1$ through carbon to form a ring selected from pyrrolidine, piperidine, homopiperazine and octahydroazocine; and/or
(6c) $R^4$ is hydrogen; and/or
(7c) $R^5$ is a group selected from trifluoromethyl, isopropoxycarbonyl, benzyloxycarbonyl, oxazolyl, benzoxazolyl, thiazolyl and benzothiazolyl; and/or
(8c) $A^1$ is a group selected from methylene, methylmethylene, ethylmethylene, isopropylmethylene, isobutylmethylene, Sec-butylmethylene, tert-butylmethylene, phenylmethylene, phenylmethylmethylene, (4-phenylbutyl)methylene, (4-hydroxyphenyl)methylmethylene, [(3-indolyl)methyl]methylene, [(5-imidazolyl)methyl]methylene, (hydroxymethyl) methylene, (tert-butoxymethyl)methylene and (carboxylmethyl)methylene; and/or
(9c) $A^2$ ismethylene or phenylmethylmethylene.

Namely,
  Compounds defined by above (1c) in the compounds represented by the general formula [I] and salts thereof,
  Compounds defined by above (2c) in the compounds represented by the general formula [I] and salts thereof,
  Compounds defined by above (3c) in the compounds represented by the general formula [I] and salts thereof,
  Compounds defined by above (4c) in the compounds represented by the general formula [I] and salts thereof,
  Compounds defined by above (5c) in the compounds represented by the general formula [I] and salts thereof,
  Compounds defined by above (6c) in the compounds represented by the general formula [I] and salts thereof,
  Compounds defined by above (7c) in the compounds represented by the general formula [I] and salts thereof,
  Compounds defined by above (8c) in the compounds represented by the general formula [I] and salts thereof,
  Compounds defined by above (9c) in the compounds represented by the general formula [I] and salts thereof, and
  Compounds defined by any combinations of two or more of above (1c), (2c), (3c), (4c), (5c), (6c), (7c), (8c) and (9c) in the compounds represented by the general formula [I] and salts thereof.

The most preferred examples of the present compound are compounds wherein the group(s) is (are) the followings in the compounds represented by the general formula [I] or salts thereof;

(1d) $R^1$ is a group selected from tert-butoxy, methoxymethyl, phenylmethoxy, (4-methoxyphenyl) methoxy, phenoxymethyl, ethylmethylamino, N-methyl-N-(phenylmethyl)amino, N-(2-ethylamino) N-methylamino and (4-methylamino)piperidino; and/or
(2d) $R^2$ is hydrogen; and/or
(3d) $R^2$ is a group joining with $A^1$ through carbon to form pyrrolidine; and/or
(4d) $R^3$ is hydrogen or phenyl; and/or
(5d) $R^3$ is a group joining with $A^1$ through carbon to form a ring selected from piperidine and homopiperazine; and/or
(6d) $R^4$ is hydrogen; and/or
(7d) $R^5$ is a group selected from isopropoxycarbonyl and (phenylmethoxy)carbonyl; and/or
(8d) $A^1$ is a group selected from methylene, methylmethylene, ethylmethylene, isopropylmethylene, isobutylmethylene, sec-butylmethylene, tert-butylmethylene, [(5-imidazolyl)methyl]methylene, (hydroxymethyl)methylene and (tert-butoxymethyl)methylene.

(9d) $A^2$ is phenylmethylmethylene.

Namely,

Compounds defined by above (1d) in the compounds represented by the general formula [I] and salts thereof, Compounds defined by above (2d) in the compounds represented by the general formula [I] and salts thereof, Compounds defined by above (3d) in the compounds represented by the general formula [I] and salts thereof, Compounds defined by above (4d) in the compounds represented by the general formula [I] and salts thereof, Compounds defined by above (5d) in the compounds represented by the general formula [I] and salts thereof, Compounds defined by above (6d) in the compounds represented by the general formula [I] and salts thereof, Compounds defined by above (7d) in the compounds represented by the general formula [I] and salts thereof, Compounds defined by above (8d) in the compounds represented by the general formula [I] and salts thereof, Compounds defined by above (9d) in the compounds represented by the general formula [I] and salts thereof, and Compounds defined by any combinations of two or more of above (1d), (2d), (3d), (4d), (5d), (6d), (7d), (8d) and (9d) in the compounds represented by the general formula [I] and salts thereof.

Since the present synthetic intermediate is selected corresponding to the chemical structure of the present compound, preferred examples of the present synthetic intermediate are also selected corresponding to the preferred examples of the present compound.

A typical synthesis route scheme of the present compound is shown below.

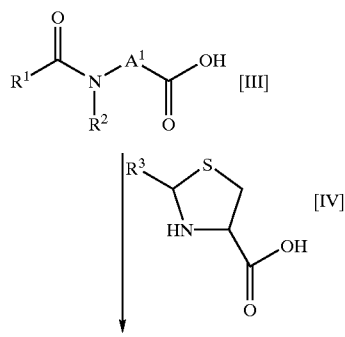

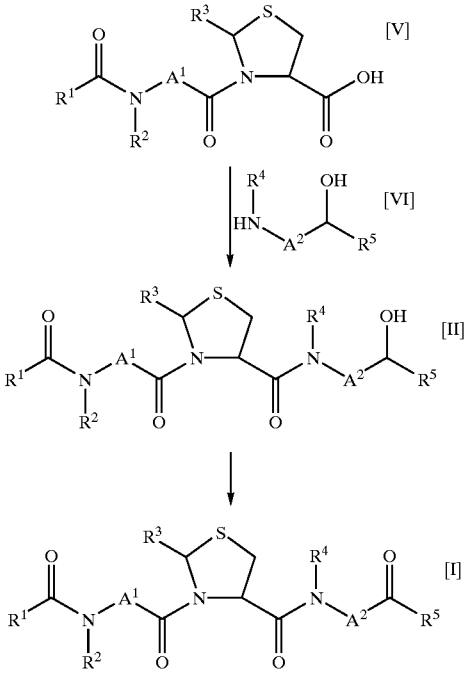

The present compound [I] can be synthesized, for example, through the synthesis route represented by the above reaction route scheme. However, this synthesis route exemplifies a typical route and does not show all methods.

This synthesis method is described in detail below.

Carboxyl group of the carboxylic acid derivative [III] is activated with a mixed acid anhydride-producing reagent (for example, isobutyl chloroformate). The acid derivative [III] is condensed with the 1,3-thiazolidinecarboxylic acid derivative [IV] in the presence of a base to convert it into the compound represented by the formula [V]. This compound [V] is reacted with the amino alcohol derivative [VI] using a condensing agent (for example, 1-ethyl-3-(3-dimethylaminopropyl)carbodiimide) to give the present synthetic intermediate represented by the formula [II]. Then, this synthetic intermediate [II] is reacted with dimethyl sulfoxide activated with acetic anhydride to oxidize hydroxy of the synthetic intermediate [II] to give the present compound [I].

In the above-mentioned synthesis method, when the reactant has a hydroxy or amino group in its molecule, these groups can be protected with suitable protecting groups, if necessary, and these protecting groups can also be removed by the conventional method after reaction. When the reactant has a carboxyl group in its molecule, the carboxyl group can be esterified, if necessary, and the ester can also be converted into a carboxylic acid by hydrolysis.

When $R^3$ joins with $A^1$ through carbon to form the nonaromatic heterocycle in the present compounds, the target products can be synthesized by a method similar to the above synthesis route by using the bicyclic carboxylic acid derivatives [VII] shown below instead of the compound [V]. These bicyclic carboxylic acid derivatives can be synthesized by Reference Examples described later.

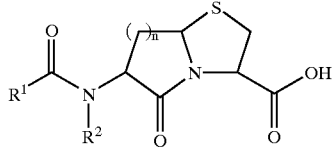

[VII]

[wherein "n" is 1 to 4.]

The compounds obtained by the above-mentioned method can be converted into the above-mentioned salts by the conventional method. The diastereo isomers and the optical isomers are present in the above-mentioned compounds represented by the general formula, and all of them are included in the present invention. When an optically active starting material is used, a single diastereo isomer and a single optical isomer are obtained. When racemate is used as a starting material, respective isomers can be separated by the conventional method, for example, by a method of using optical resolution or the like.

As described in the part of "Background Art", various compounds having a thiazolidine ring as a main skeleton are known to be used for drugs.

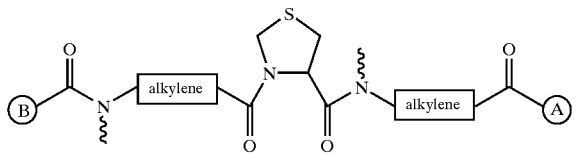

[VIII]

However, the present compounds are novel compounds being unknown in literatures. As shown in the above formula [VIII], features of their chemical structure composing a main skeleton are as follows. 1) First, the carboxyl group at the 4th-position of 4-thiazolidinecarboxylic acid is amidated, and the various substituents "A" having a carbonyl group such as lower alkoxycarbonyl and aromatic heterocycles are introduced into the amide moiety through the "alkylene", and 2) the various substituents [B—(CO)—N(~)-alkylene-] are introduced into the nitrogen atom at the 3rd-position of 4-thiazolidinecarboxylic acid through a carbonyl group. Focusing attention on these two points and studying precisely, the present inventors have succeeded in preparing the many novel compounds.

Administration methods of drugs can be a method of administering active compounds themselves or a method of administering the drugs in the form to be decomposed in vivo and to be converted into the active compounds, namely in the form of prodrugs. Both are widely used. The present compounds also have a carboxyl group in their molecule. The present compounds can be administered in the form of the carboxylic acid and also in the form of an ester which can be converted into the carboxylic acid by hydrolysis. When the present compounds have an amino group in their molecule, the present compounds can be administered with the amino group protected with a suitable protecting group.

Further, in order to find utility of the present compounds, chymase inhibitory effects of the present compounds were studied. Details will be described later in the part of "Pharmacological Test". The present compounds exhibited excellent chymase inhibitory effects. Chymase has been reported to exist in systemic tissues such as gut, skin and lung centering around tissues of cardiovascular system and to participate in outbreaks of physiologic functions such as cardiovascular lesion, inflammation, immune functions and tissue remodeling (Journal of Clinical and Experimental Medicine, 172 (9), 559 (1995)). Chymase has been reported to participate also in outbreaks of cardiac infarction, heart failure, blood-vessel restenosis after PTCA and the like (Blood Vessel & Endothelium,5 (5), 37 (1995)), hypertension (FEBS Lett., 406, 301(1997)), diabetes complication (Biol. Chem., Hoppe Seyler (GERMANY, WEST), 369 Suppl., p299), allergic diseases (Nobuhiko Katsunuma, "Intracellular Proteolysis", p. 101–106), asthma (J. Pharmacol. Exp. Ther., 244 (1), 133 (1987)) and the like. Chymase inhibitors are expected to be effective in treating these diseases.

The present compound can be administered orally or parenterally. Examples of dasage forms are tablets, capsules, granules, powders, injections, eyedrops and the like. The present compound can be formulated into preparations by the conventional methods. For example, oral preparations such as tablets, capsules, granules and powders can be produced by adding optionally diluents such as lactose, crystalline cellulose, starch and vegetable oil; lubricants such as magnesium stearate and talc; binders such as hydroxypropylcellulose and polyvinyl pyrrolidone; disintegrator such as calcium carboxymethylcellulose or low-substituted hydroxypropylmethylcellulose; coating agent such as hydroxypropylmethylcellulose, macrogol or silicone resin; or film forming agent such as gelatin film. Eyedrops can be produced, if necessary, by adding isotonic agents such as sodium chloride and concentrated glycerine; buffers such as sodium phosphate and sodium acetate; surfactants such as polyoxyethylenesorbitan monooleate, polyoxyl 40 stearate and polyoxyethylene hydrogenated castor oil; stabilizers such as sodium citrate and disodium edetate; preservatives such as benzalkonium chloride and paraben; and the like. pH can be in a range acceptable for ophthalmic preparations, and it is more preferably in a range of 4 to 8.

The dosage of the present compound can be selected suitably according to the symptom, age, dosage form and the like. In case of the oral preparation, the present compound can be administered once to several times per day with a daily dose of 0.1 to 5000 mg, preferably 1 to 1000 mg.

Examples of preparations and formulations and results of pharmacological test of the present invention are shown below. These examples do not limit the scope of the invention, but are intended to make the invention more clearly understandable.

BEST MODE FOR CARRYING OUT THE INVENTION

Reference Examples

Preparation of Compounds

The following Reference Examples 1 to 9 show examples of the synthesis of the carboxylic acid derivative [III] shown in the above synthesis route scheme.

Reference Example 1
Ethyl (2RS)-6-phenyl-2-[(phenylmethoxy)carbonyl]aminohexanoate (Reference compound No. 1-1)

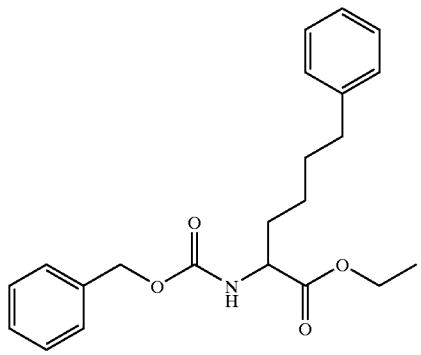

Triethylamine (0.4 ml) is added to a solution of ethyl (2RS)-2-amino-6-phenylhexanoate (0.52 g) in methylene chloride (10 ml). After ice cooling, benzyl chloroformate (0.4 ml) is added dropwise thereto, temperature is raised to room temperature, and the mixture is stirred overnight. Saturated brine is added to the reaction mixture, and the whole is extracted with ethyl acetate. The extract is washed with 0.1 N hydrochloric acid, a saturated aqueous sodium hydrogencarbonate solution and saturated brine successively and dried over anhydrous magnesium sulfate. The extract is concentrated under reduced pressure, and the concentrate is purified by silica gel column chromatography to give 0.33 g of the titled compound.

IR(Film,cm$^{-1}$): 3341,3062,3027,2935,2859,1724,1603, 1527,1453, 1371,1343,1211.

6-Phenyl-2-[(phenylmethoxy)carbonyl]aminohexanoic acid (Reference compound No. 1-2)

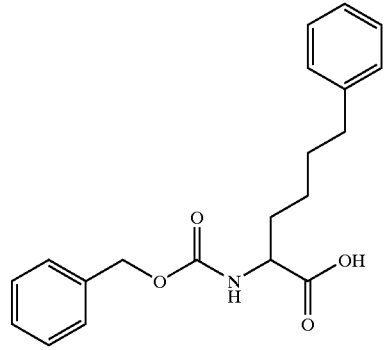

A 4 N aqueous lithium hydroxide solution (0.6 ml) is added to a solution of ethyl (2RS)-6-phenyl-2-[(phenylmethoxy)carbonyl]aminohexanoate (0.3 g) in methanol (10 ml), and the mixture is stirred for 30 minutes. Citric acid is added to the reaction mixture to acidify it, and the whole is concentrated under reduced pressure. Ether is added to the residue, and the whole is extracted with a saturated aqueous sodium hydrogencarbonate solution. Then, the extract is acidified with 1 N hydrochloric acid, and the whole is extracted with ethyl acetate. The extract is washed with saturated brine and dried over anhydrous magnesium sulfate. The extract is concentrated under reduced pressure to give 0.24 g of the titled compound.

IR(Film,cm$^{-1}$): 3343,3027,2856,1750,1711,1668,1555, 1496,1453, 1418,1336,1306,1256,1211.

Reference Example 2
(2S)-2-[(Phenylmethoxy)carbonyl]aminobutyric Acid (Reference compound No. 2-1)

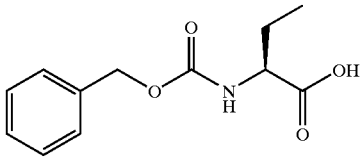

Sodium hydrogencarbonate (1.34 g) is dissolved in water (10 ml), (2S)-2-aminobutyric acid (0.50 g) is added to the solution, and the mixture is stirred for five minutes. Then, a solution of benzyl chloroformate (1.4 ml) in diethyl ether (4.0 ml) is added dropwise to the mixture, and the whole is stirred at room temperature for five hours. A 0.1 N aqueous sodium hydroxide solution is added to the reaction mixture to basify it, and the whole is washed with diethyl ether. Then, 2 N hydrochloric acid is added to the mixture to acidify it, and the whole is extracted with ethyl acetate. The extract is washed with water and saturated brine successively and dried over anhydrous magnesium sulfate. The extract is concentrated under reduced pressure to give the titled compound.

[α] D$^{20}$ −15.3° (c=0.98, methanol); IR(Film,cm$^{-1}$): 3325, 2972,1713,1531.

The following compounds are obtained by a method similar to Reference Example 2.

(2S)-3,3-Dimethyl-2-[(phenylmethoxy)carbonyl] aminobutyric acid (Reference compound No. 2-2)

(2S)-2-Phenyl-2-[(phenylmethoxy)carbonyl]aminobutyric acid (Reference compound No. 2-3)
mp 129.5–130.8° C.; [α] D$^{20}$ −110.6° (c=0.5, methanol); IR(KBr,cm$^{-1}$): 3402,1745,1667,1533,1248,1172,720,696.

(2S)-3-(4-Hydroxyphenyl)-2-[(phenylmethoxy)carbonyl] aminopropionic acid (Reference compound No. 2-4)

(2S)-3-Methyl-2-(methylcarbonyl)aminobutyric acid (Reference compound No. 2-5)

(2S)-3-Methyl-2-[(phenylmethyl)carbonyl]aminobutyric acid (Reference compound No. 2-6)

(2S)-3-Methyl-2-[(2-phenylethyl)carbonyl]aminobutyric acid (Reference compound No. 2-7)
mp 134.5–140.6° C.; [α] D$^{20}$ −12.4° (c=1.0, methanol); IR(KBr,cm$^{-1}$): 3317,1709,1610,1557.

(2S)-2-[(Methoxymethyl)carbonyl]amino-3-methylbutyric acid (Reference compound No. 2-8)
mp 86.0–90.5° C.; IR(Film,cm$^{-1}$): 3377,2977,1723,1631, 1539,1428,1245,1120,1004, 744,685.

(2S)-3-Methyl-2-[(phenoxymethyl)carbonyl]aminobutyric acid (Reference compound No. 2-9)
IR(Film,cm$^{-1}$): 3375,2973,2605,1714,1624,1551,1496, 1467,1446, 1429,1244.

(2S)-2-(tert-Butoxycarbonyl)amino-3-methylbutyric acid (Reference compound No. 2-10)

(2S)-3-Methyl-2-(phenoxycarbonyl)aminobutyric acid (Reference compound No. 2-11)

(2S)-2-[(Methoxymethyl)carbonyl]aminopropionic acid (Reference compound No. 2-12)
IR(KBr,cm$^{-1}$): 3385,1733,1628,1545,1245,1217,1149, 1124.

(2S)-2-[N-Methyl-N-[(phenylmethoxy)carbonyl]] aminopropionic acid (Reference compound No. 2-13)

(2S)-2-[N-Ethyl-N-[(phenylmethoxy)carbonyl]amino] propionic acid (Reference compound No. 2-14)

(2S)-1-[(Phenylmethoxy)carbonyl]pyrrolidine-2-carboxylic acid (Reference compound No. 2-15)

(4R)-3-(Phenylmethoxy)carbonyl-1,3-thiazolidine-4-carboxylic acid (Reference compound No. 2-16)

Reference Example 3

(2S)-2-[(Phenylmethoxy)carbonyl]amino-3-[1-(triphenylmethyl)imidazol-5-yl]propionic Acid (Reference compound No. 3-1)

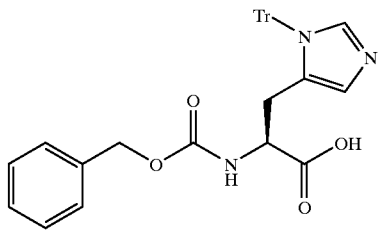

(2S)-3-(2-Imidazolyl)-2-[(phenylmethoxy)carbonyl] aminopropionic acid (2.89 g) is suspended in pyridine (40 ml), and the suspension is cooled with ice. Then, trityl chloride (3.62 g) is added to the suspension, and the mixture is stirred overnight. The reaction mixture is concentrated under reduced pressure, a 1 N aqueous sodium hydroxide solution is added to the concentrate, and the whole is washed with diethyl ether. Then, citric acid is added to the mixture to acidify it, and the whole is extracted with chloroform. The extract is washed with saturated brine and dried over anhydrous magnesium sulfate. The extract is concentrated under reduced pressure to give 4.85 g of the titled compound.

IR(KBr,cm$^{-1}$): 3411,3306,3151,3060,3030,2943,2477, 1959,1816, 1718,1597,1493,1445.

The following compound is obtained by a method similar to Reference Example 3.

(2S)-2-[(Phenylmethoxy)carbonyl]amino-3-[1-(triphenylmethyl)indol-3-yl]propionic acid (Reference compound No. 3-2)

Reference Example 4

(2S)-2-[[(4-Methoxyphenyl)methoxy]carbonyl]amino-3-methylbutyric Acid (Reference compound No. 4-1)

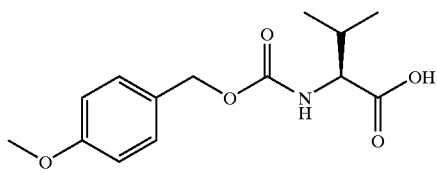

L-Valine (0.59 g) is dissolved in a 1 N aqueous sodium hydroxide solution (11 ml), and the mixture is cooled with ice and then stirred for 10 minutes. [(4-Methoxyphenyl) methoxy]carbonylazide (1.14 g) is added to the mixture, and the whole is stirred overnight. The reaction mixture is washed with ethyl acetate, a 10% aqueous citric acid solution is added to the reaction mixture to acidify it, and the whole is extracted with ethyl acetate. The extract is washed with saturated brine and dried over anhydrous magnesium sulfate. The extract is concentrated under reduced pressure to give 0.57 g of the titled compound.

IR(Film,cm$^{-1}$): 3326,2965,2837,1715,1613,1596,1515, 1466,1303, 1247,1176.

Reference Example 5

1-[(tert-Butoxycarbonyl)amino]-2-chloroethane (Reference compound No. 5-1)

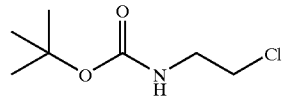

A solution of triethylamine (2.22 g) in methylene chloride (3 ml) is added dropwise to a solution of 2-chloroethylamine (1.27 g) in methylene chloride (9 ml). The mixture is stirred for 10 minutes, a solution of di-tert-butyl dicarbonate (2.00 g) in methylene chloride is added to the mixture, and the whole is stirred for 0.5 hour. Insoluble matters are filtered out, and the filtrate is concentrated under reduced pressure. Water is added to the residue, and the whole is extracted with ethyl acetate. The extract is washed with saturated brine and dried over anhydrous magnesium sulfate. The extract is concentrated under reduced pressure to give 1.53 g of the titled compound.

N-2-[(tert-Butoxycarbonyl)amino]ethyl-N-methylamine (Reference compound No. 5-2)

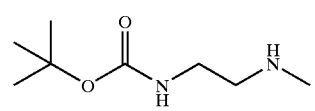

With ethanol (20 ml) are mixed 2-chloro-1-[(tert-butoxycarbonyl)amino]ethane (1.51 g) and a 40% aqueous aminomethane solution (19.6 g), and the mixture is stirred overnight. The reaction mixture is concentrated under reduced pressure. A 2 N aqueous sodium hydroxide solution is added to the resulting residue, and the whole is extracted with chloroform. The extract is dried over anhydrous sodium sulfate. The extract is concentrated under reduced pressure, and the resulting residue is purified by column chromatography to give 1.11 g of the titled compound.

Reference Example 6

4-Methylamino-1-(phenylmethyl)piperidine (Reference compound No. 6-1)

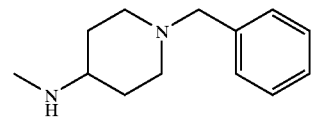

A solution of 1-phenylmethyl-4-piperidone (20.0 g) and methylamine hydrochloride (35.7 g) in isopropanol (270 ml) is cooled with ice. A solution of sodium methoxide (28.5 g) in methanol (120 ml) is added dropwise thereto, and the mixture is stirred for two hours. Then, sodium hydroxide (7.00 g) is added thereto, temperature is raised to room temperature, and the whole is stirred for one hour. The reaction mixture is cooled with ice again, sodium borohydride (5.40 g) is added thereto, and the whole is stirred for 1.5 hours. Insoluble matters are filtered out, and the filtrate is concentrated under reduced pressure. Water is added to the residue, and the whole is extracted with diethyl ether. The extract is washed with saturated brine and dried over anhydrous magnesium sulfate. The extract is concentrated under reduced pressure to give 11.8 g of the titled compound as an oily matter.

IR(Film,cm$^{-1}$): 3284,2936,2796,1994,791,739.

4-(N-tert-Butoxycarbonyl-N-methylamino)-1-(phenylmethyl)piperidine (Reference compound No. 6-2)

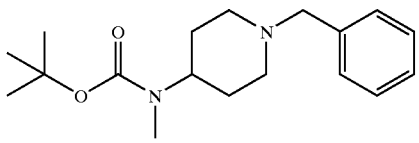

A solution of di-tert-butyl dicarbonate (14.1 g) in tetrahydrofuran (50 ml) is added dropwise to a solution of 4-methylamino-1-(phenylmethyl)piperidine (11.0 g) in tetrahydrofuran (110 ml) under ice cooling, and the mixture is stirred for 0.5 hour. Saturated brine is added to the reaction mixture, and the whole is extracted with ethyl acetate. The extract is washed with a saturated aqueous sodium hydrogencarbonate solution and saturated brine successively and dried over anhydrous sodium sulfate. The extract is concentrated under reduced pressure, and the resulting residue is purified by silica gel column chromatography to give 12.7 g of the titled compound.

IR(Film,cm$^{-1}$): 2938,2802,2760,1693,1601,1494,1364, 1324,1149.

4-(N-tert-Butoxycarbonyl-N-methylamino)piperidine (Reference compound No. 6-3)

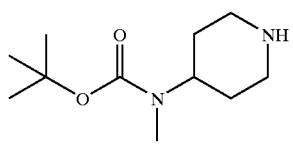

Palladium hydroxide/carbon (2.00 g) is added to a solution of 4-[(tert-butoxycarbonyl)methylamino]-1-(phenylmethyl)piperidine (12.0 g) in ethanol (138 ml) under a nitrogen stream. Then, the mixture is stirred under a hydrogen atmosphere for 2.5 days. The catalyst is filtered out, and the filtrate is concentrated under reduced pressure to give 0.46 g of the titled compound.

IR(Film,cm$^{-1}$): 3164,2975,2859,1691,1452,1406,1366, 1322,1154.

Reference Example 7

Phenylmethyl (2S)-2-[(N-ethyl-N-methylamino)carbonyl]amino-3-methylbutyrate (Reference compound No. 7-1)

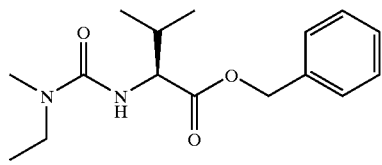

A solution of L-valine benzyl ester hydrogen p-toluenesulfonate (1.00 g), imidazole (0.18 g) and carbonyldiimidazole (0.43 g) in tetrahydrofuran (10 ml) is stirred at room temperature for 0.5 hour. Then, ethylmethylamine (0.24 ml) is added to the solution, temperature is raised to 60° C., and the mixture is stirred for two hours. After standing, 1 N hydrochloric acid is added to the reaction mixture, and the whole is extracted with ethyl acetate. The extract is washed with water and saturated brine successively and dried over anhydrous magnesium sulfate. The extract is concentrated under reduced pressure, and the resulting residue is purified by silica gel column chromatography to give the titled compound.

IR(Film,cm$^{-1}$): 3361,2964,2933,2874,1737,1643,1519.

The following compounds are obtained by a method similar to Reference Example 7.

Methyl (2S)-3-methyl-2-[[N-methyl-N-(phenylmethyl)amino]carbonyl]aminobutyrate (Reference compound No. 7-2)

IR(Film,cm$^{-1}$): 3367,2964,1739,1643,1530,1205,736, 701.

Phenylmethyl (2S)-2-[[N-[2-[(tert-butoxycarbonyl)amino]ethyl]N-methylamino]carbonyl]amino-3-methylbutyrate (Reference compound No. 7-3)

IR(Film,cm$^{-1}$): 3327,2968,1738,1694,1644,1519,1392, 1366,1252, 1173.

Phenylmethyl (2S)-2-[[4-[[N-(tert-butoxycarbonyl)-N-methylamino]piperidino]carbonyl]amino-3-methylbutyrate (Reference compound No. 7-4)

IR(Film,cm$^{-1}$): 3368,2965,2250,1738,1689,1525,1319, 1154.

Phenylmethyl (2S)-3-methyl-2-[(4-methylpiperazino)carbonyl]-aminobutyrate (Reference compound No. 7-5)

IR(Film,cm$^{-1}$): 3349,2964,2937,1738,1634,1524,1456, 1293,1267, 1159,1003.

Reference Example 8

(2S)-2-[(N-Ethyl-N-methylamino)carbonyl]amino-3-methylbutyric acid (Reference compound No. 8-1)

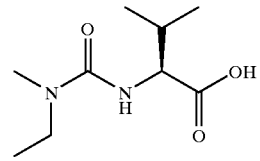

Palladium hydroxide/carbon (0.40 g) is added to a solution of phenylmethyl (2S)-2-[(ethylmethylamino)carbonyl]amino-3-methylbutyrate (0.70 g) in methanol under a nitrogen stream. Then, the mixture is stirred under a hydrogen atmosphere for 0.5 hour. The catalyst is filtered out, and the filtrate is concentrated under reduced pressure to give 0.46 g of the titled compound.

IR(Film,cm$^{-1}$): 3370,2965,1722,1615.

The following compounds are obtained by a method similar to Reference Example 8.

(2S)-2-[[N-[2-[(tert-Butoxycarbonyl)amino]ethyl]-N-methylamino]carbonyl]amino-3-methylbutyric acid (Reference compound No. 8-2)

IR(KBr,cm$^{-1}$): 3357,2976,1720,1636,1535,1394,1367, 1253,1171, 968,766.

(2S)-2-[[4-[N-(tert-Butoxycarbonyl)-N-methylamino]piperidino]carbonyl]amino-3-methylbutyric acid (Reference compound No. 8-3)

IR(KBr,cm$^{-1}$): 3368,2968,2591,1735,1696,1636,1534, 1368,1323, 1157.

(2S)-3-Methyl-2-[(4-methylpiperazino)carbonyl]amino butyric acid (Reference compound No. 8-4)

IR(KBr,cm$^{-1}$): 3359,2964,2604, 1641,1532,1466,1398, 1263,1227, 976,770.

Reference Example 9

(2S)-3-Methyl-2-[[N-methyl-N-(phenylmethyl)amino]carbonyl]aminobutyric Acid (Reference compound No. 9-1)

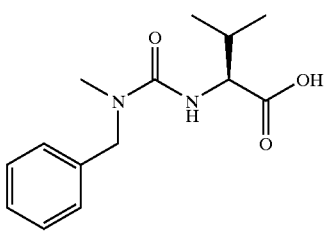

A 4 N aqueous lithium hydroxide solution (3.0 ml) is added to a solution of methyl (2S)-3-methyl-2-[[N-methyl-N-(phenylmethyl)-amino]carbonyl]aminobutyrate (1.21 g) in methanol/tetrahydrofuran (15 ml/25 ml) under ice cooling. Raising temperature to room temperature, the mixture is stirred for one hour. A saturated aqueous sodium hydrogencarbonate solution is added to the reaction mixture, and the whole is washed with ethyl acetate. Then, 1 N hydrochloric acid is added to the mixture to acidify it, and the whole is extracted with ethyl acetate. The extract is washed with saturated brine and dried over anhydrous magnesium sulfate. The extract is concentrated under reduced pressure, and the resulting residue is purified by silica gel column chromatography to give 0.75 g of the titled compound.

IR(Film,cm$^{-1}$): 3391,2965,1722,1615,1524,1214,1026, 737,700.

The following Reference Example 10 shows examples of the synthesis of the compound [V] shown in the above synthesis route scheme.

In this example, the compounds whose synthetic methods are shown in Reference Examples 1 to 9, commercially available compounds or compounds synthesized by usual synthetic methods are used as the carboxylic acid derivative [III] and the 1,3-thiazolidinecarboxylic acid derivative [IV], which are synthetic precursors of the present compounds.

Reference Example 10
(4R)-3-[(2S)-3-Methyl-1-oxo-2-[[(phenylmethoxy)carbonyl]amino]butyl]-1,3-thiazolidine-4-carboxylic Acid (Reference compound No. 10-1)

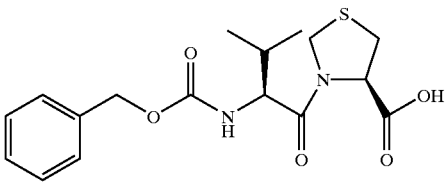

N-Methylmorpholine (2.43 g) is added dropwise to a solution of (2S)-3-methyl-2-[[(phenylmethoxy)carbonyl] aminobutyric acid (5.02 g) in tetrahydrofuran (40 ml) under ice cooling. The mixture is cooled with ice/sodium chloride, isobutyl chloroformate (2.73 g) is added dropwise to the mixture, and the whole is stirred for 30 minutes. A solution of (4R)-1,3-thiazolidine-4-carboxylic acid (2.66 g) in a 1 N aqueous sodium hydroxide solution (24 ml) cooled with ice is added dropwise to the reaction mixture, temperature is raised to room temperature, and the whole is stirred overnight. A 5% aqueous citric acid solution is added to the reaction mixture to acidify it, and the whole is extracted with ethyl acetate. The extract is washed with water and saturated brine successively and dried over anhydrous magnesium sulfate. The extract is concentrated under reduced pressure, and the residue is purified by silica gel column chromatography to give 1.32 g of the titled compound as an amorphous matter.

[α] D$^{20}$ −114.2° (c=0.5, methanol); IR(Film,cm$^{-1}$): 3303, 2966,1715,1649,1529,1429,1236,755.

The following compounds are obtained by a method similar to Reference Example 10.

(4R)-3-[1-Oxo-2-[[(phenylmethoxy)carbonyl]amino]ethyl]-1,3-thiazolidine-4-carboxylic acid (Reference compound No. 10-2)

[α] D$^{20}$ −91.2° (c=0.6, methanol); IR(Film,cm$^{-1}$): 3333, 1721,1658,1529,1453,1253,754,698.

(4R)-3-[(2S)-1-Oxo-2-[[(phenylmethoxy)carbonyl]amino] propyl]-1,3-thiazolidine-4-carboxylic acid (Reference compound No. 10-3)

[α] D$^{20}$ −125.3° (c=0.5, methanol); IR(KBr,cm$^{-1}$): 3384, 1743,1679,1637,1521,1453,1237,1220.

(4R)-3-[(2S)-1-Oxo-2-[[(phenylmethoxy)carbonyl]amino] butyl]-1,3-thiazolidine-4-carboxylic acid (Reference compound No. 10-4)

IR(Film,cm$^{-1}$): 3306,2969,1714,1650,1528.

(4R)-3-[(2S)-4-Methyl-1-oxo-2-[[(phenylmethoxy)carbonyl]amino]pentyl]-1,3-thiazolidine-4-carboxylic acid (Reference compound No. 10-5)

IR(Film,cm$^{-1}$): 3305,2958,1713,1649,1530,1434,1255, 1046,911, 734,698.

(4R)-3-[(2S,3RS)-3-Methyl-1-oxo-2-[[(phenylmethoxy)carbonyl]amino]pentyl]-1,3-thiazolidine-4-carboxylic acid (Reference compound No. 10-6)

IR(Film,cm$^{-1}$): 3297,2965,1715,1650,1529,1427,1252, 756,697.

(4R)-3-[(2S)-3,3-Dimethyl-1-oxo-2-[[(phenylmethoxy)carbonyl]amino]butyl]-1,3-thiazolidine-4-carboxylic acid (Reference compound No. 10-7)

(4R)-3-[(2S)-1-Oxo-2-phenyl-2-[[(phenylmethoxy)carbonyl]amino]ethyl]-1,3-thiazolidine-4-carboxylic acid (Reference compound No. 10-8)

mp 164.0–175.0° C.; [α] D$^{20}$ −119.0° (c=0.5, methanol); IR(KBr,cm$^{-1}$): 3381,1750,1685,1649,1498,1420,1215, 1170.

(4R)-3-[(2S)-1-Oxo-3-phenyl-2-[[(phenylmethoxy)carbonyl]amino]propyl]-1,3-thiazolidine-4-carboxylic acid (Reference compound No. 10-9)

IR(Film,cm$^{-1}$): 3304,3029,2956,1714,1649,1526,1429, 1249.

(4R)-3-[(2RS)-1-Oxo-6-phenyl-2-[[(phenylmethoxy)carbonyl]amino]hexyl]-1,3-thiazolidine-4-carboxylic acid (Reference compound No. 10-10)

(4R)-3-[(2S)-3-(4-Hydroxyphenyl)-1-oxo-2-[[(phenylmethoxy)carbonyl]amino]propyl]-1,3-thiazolidine-4-carboxylic acid (Reference compound No. 10-11)

IR(KBr,cm$^{-1}$): 3307,3030,2953,1699,1643,1614,1515, 1445,1225.

(4R)-3-[(2S)-1-Oxo-2-[(phenylmethoxy)carbonyl]amino-3-1-(triphenylmethyl)imidazol- 5-yl]propyl]-1,3-thiazolidine-4-carboxylic acid (Reference compound No. 10-12)

IR(KBr,cm$^{-1}$): 3400,3305,3151,3060,3031,2942,2468, 1960,1719, 1650, 1493,1444,1213,1129.

(4R)-3-[(2S)-1-Oxo -2-[(phenylmethoxy)carbonyl]amino-3-[1-(triphenylmethyl)indol-3--yl]propyl]-1,3-thiazolidine-4-carboxylic acid (Reference compound No. 10-13)

(4R)-3-[(2S)-3-(tert-Butoxy)-1-oxo-2-[[(phenylmethoxy)carbonyl]amino]propyl]-1,3-thiazolidine-4-carboxylic acid (Reference compound No. 10-14)

IR(Film,cm$^{-1}$): 3304,2973,1722,1652,1520,1436,1194, 754,698.

(4R)-3-[(2S)-3-(tert-Butoxycarbonyl)-1-oxo-2-[[(phenylmethoxy)carbonyl]amino]propyl]-1,3-thiazolidine-4-carboxylic acid (Reference compound No. 10-15)

(4R)-3-[(2S)-3-Methyl-2-(methylcarbonyl)amino-1-oxobutyl]-1,3-thiazolidine-4-carboxylic acid (Reference compound No. 10-16)
[α] D$^{20}$ −75.7° (c=0.5, methanol); IR(Film,cm$^{-1}$): 3304, 2967, 1732,1633,1548,1435,12 16,756.

(4R)-3-[(2S) -3-Methyl-1-oxo-2-[[(phenylmethyl)carbonyl]amino]butyl]-1,3-thiazolidine-4-carboxylic acid (Reference compound No. 10-17)

(4R)-3-[(2S)-3-Methyl-1-oxo-2-[[(2-phenylethyl)carbonyl]amino]butyl]-1,3-thiazolidine-4-carboxylic acid (Reference compound No. 10-18)
IR(Film,cm$^{-1}$): 3749,2963,1732,1617, 1542,1425.

(4R)-3-[(2S)-2-[(Methoxymethyl)carbonyl]amino-3-methyl-1-oxobutyl]-1,3-thiazolidine-4-carboxylic acid (Reference compound No. 10-19)
IR(KBr,cm$^{-1}$): 3362,2967,1738,1653,1623,1542,1433, 1250,1202, 1124,656.

(4R)-3-[(2S)-3-Methyl-1-oxo-2-[(phenoxymethyl)carbonyl]amino]butyl]-1,3-thiazolidine-4-carboxylic acid (Reference compound No. 10-20)
IR(Film,cm$^{-1}$): 3408,3304,2966,1731,1642,1535,1494, 1438,1371, 1240,1082.

(4R)-3-[(2S)-2-(tert-Butoxycarbonyl)amino-3-methyl-1-oxobutyl]-1,3-thiazolidine-4-carboxylic acid (Reference compound No. 10-21)
[α] D$^{20}$ −130.0° (c=0.6, methanol); IR(Film,cm$^{-1}$): 3319, 2974,1701,1653,1424,1368,1168,756.

(4R)-3-[(2S)-3-Methyl-1-oxo-2-[(phenoxycarbonyl)amino]butyl]-1,3-thiazolidine-4-carboxylic acid (Reference compound No. 10-22)

(4R)-3-[(2S)-2-[[(4-Methoxyphenyl)methoxy]carbonyl]amino-3-methyl-1-oxobutyl]-1,3-thiazolidine-4-carboxylic acid (Reference compound No. 10-23)
IR(Film,cm$^{-1}$): 3306,2964,2837,1713,1649,1613,1515, 1425,1302, 1247,1176.

(4R)-3-[(2S)-2-[(N-Ethyl-N-methylamino)carbonyl]amino-3-methyl-1-oxobutyl]-1,3-thiazolidine-4-carboxylic acid (Reference compound No. 10-24)

(4R)-3-[(2S)-3-Methyl-2-[[N-methyl-N-(phenylmethyl)amino]carbonyl]amino-1-oxobutyl]- 1,3-thiazolidine-4-carboxylic acid (Reference compound No. 10-25)
IR(KBr,cm$^{-1}$): 3343,2964,1737,1611,1532,1423,1218, 736,700.

(4R)-3-[(2S)-2-[[N-[2-[(tert-Butoxycarbonyl)amino]ethyl]-N-methylamino]carbonyl]amino-3-methyl-1-oxobutyl]-1,3-thiazolidine-4-carboxylic acid (Reference compound No. 10-26)
IR(KBr,cm$^{-1}$): 3355,2975,1729,1609,1529,1439,1367, 1169,1074, 1044.

(4R)-3-[(2S)-2-[[4-[N-(tert-Butoxycarbonyl)-N-methylamino]piperidino]carbonyl]amino-3-methyl-1-oxobutyl]-1,3-thiazolidine4-carboxylic acid (Reference compound No. 10-27)

(4R)-3-[(2S)-3-Methyl-2-[(4-methylpiperazino)carbonyl]amino-1-oxobutyl]-1,3-thiazolidine-4-carboxylic acid (Reference compound No. 10-28)

(4R)-3-[(2S)-2-[(Methoxymethyl)carbonyl]amino-1-oxopropyl]-1,3-thiazolidine-4-carboxylic acid (Reference compound No. 10-29)
mp 172.3–173.5° C.; [α] D$^{20}$ −142.8° (c=0.6, methanol); IR(Film,cm$^{-1}$): 3368,1736,1632,1539,1424,1221,1183, 1119.

(4R)-3-[(2S)-2-[N-Methyl-N-[(phenylmethoxy)carbonyl]amino]-1-oxopropyl]-1,3-thiazolidine-4-carboxylic acid (Reference compound No. 10-30)

(4R)-3-[(2S)-2-[N-Ethyl-N-[(phenylmethoxy)carbonyl]amino]-1-oxopropyl]-1,3-thiazolidine-4-carboxylic acid (Reference compound No. 10-31)

(4R)-3-[(2S)-1-[(Phenylmethoxy)carbonyl]pyrrolidin-2-yl]carbonyl-1,3-thiazolidine-4-carboxylic acid (Reference compound No. 10-32)
IR(Film,cm$^{-1}$): 3453,2962,1692,1426,1386,1360,1186, 1121,1011.

(4R)-3-[(4R)-3-(Phenylmethoxy)carbonyl-1,3-thiazolidin-4-yl]carbonyl-1,3-thiazolidine-4-carboxylic acid (Reference compound No. 10-33)

(2RS,4R)-3-[(2S)-3-Methyl-1-oxo-2-[[(phenylmethoxy)carbonyl]amino]butyl]-2-phenyl-1,3-thiazolidine-4-carboxylic acid (Reference compound No. 10-34)

(2RS,4R)-3-[1-Oxo-2-[[(phenylmethoxy)carbonyl]amino]ethyl]-2-phenyl-1,3-thiazolidine-4-carboxylic acid (Reference compound No. 10-35)

(2RS,4R)-3-[(2S)-1-Oxo-2-[[(phenylmethoxy)carbonyl]amino]-propyl]-2-phenyl-1,3-thiazolidine-4-carboxylic acid (Reference compound No.10-36)

(2RS,4R)-3-[(2S)-1-Oxo-2-[[(phenylmethoxy)carbonyl]amino]butyl]-2-phenyl-1,3-thiazolidine-4-carboxylic acid (Reference compound No. 10-37)

(2RS,4R)-3-[(2S)-4-Methyl-1-oxo-2-[[(phenylmethoxy)carbonyl]amino]pentyl]-2-phenyl-1,3-thiazolidine-4-carboxylic acid (Reference compound No. 10-38)

(2RS,4R)-3-[(2S,3RS)-3-Methyl-1-oxo2-[[(phenylmethoxy)carbonyl]amino]pentyl]-2-phenyl-1,3-thiazolidine -4-carboxylic acid (Reference compound No. 10-39)

(2RS,4R)-3-[(2S)-3,3-Dimethyl-1-oxo-2-[[(phenylmethoxy)carbonyl]amino]butyl]-2-phenyl-1,3-thiazolidine-4-carboxylic acid (Reference compound No. 10-40)

(2RS,4R)-3-[(2S)-1-Oxo-2-phenyl-2-[[(phenylmethoxy)carbonyl]amino]ethyl]-2-phenyl-1,3-thiazolidine-4-carboxylic acid (Reference compound No. 10-41)

(2RS,4R)-3-[(2S)-1-Oxo-3-phenyl-2-[[(phenylmethoxy)carbonyl]amino]propyl]-2-phenyl-1,3-thiazolidine-4-carboxylic acid (Reference compound No. 10-42)

(2RS,4R)-3-[(2RS)-1-Oxo-6-phenyl-2-[[(phenylmethoxy)carbonyl]amino]hexyl]-2-phenyl-1,3-thiazolidine-4-carboxylic acid (Reference compound No. 10-43)

(2RS,4R)-3-[(2S)-3-(4-Hydroxyphenyl)-1-oxo-2-[[(phenylmethoxy)carbonyl]amino]propyl]-2-phenyl-1,3-thiazolidine-4 carboxylic acid (Reference compound No. 10-44)

(2RS,4R)-3-[(2S)-1-Oxo-2-[(phenylmethoxy)carbonyl]amino-3-[1-(triphenylmethyl)imidazol-5-yl]propyl]-2-phenyl-1,3-thiazolidine4-carboxylic acid (Reference compound No. 10-45)

(2RS,4R)-3-[(2S)-1-Oxo-2-[(phenylmethoxy)carbonyl]amino-3-[1-(triphenylmethyl)indol-3-yl]propyl]-2-phenyl-1,3-thiazolidine-4 carboxylic acid (Reference compound No. 10-46)

(2RS,4R)-3-[(2S)-3-(tert-Butoxy)-1-oxo-2-[[(phenylmethoxy)carbonyl]amino]propyl]-2-phenyl-1,3-thiazolidine-4-carboxylic acid (Reference compound No. 10-47)

(2RS,4R)-3-[(2S)-3-(tert-Butoxycarbonyl)-1-oxo-2-[[(phenylmethoxy)carbonyl]amino]propyl]-2-phenyl-1,3-thiazolidine-4 carboxylic acid (Reference compound No. 10-48)

(2RS,4R)-3-[(2S)-3-Methyl-2-(methylcarbonyl)amino-1-oxobutyl]-2-phenyl-1,3-thiazolidine-4-carboxylic acid (Reference compound No. 10-49)

(2RS,4R)-3-[(2S)-3-Methyl-1-oxo-2-[[(phenylmethyl)carbonyl]amino]butyl]-2-phenyl-1,3-thiazolidine-4-carboxylic acid (Reference compound No. 10-50)

(2RS,4R)-3-[(2S)-3-Methyl-1-oxo-2-[[(2-phenylethyl)carbonyl]amino]butyl]-2-phenyl-1,3-thiazolidine-4-carboxylic acid (Reference compound No. 10-51)

(2RS,4R)-3-[(2S)-2-[(Methoxymethyl)carbonyl]amino-3-methyl-1-oxobutyl]-2-phenyl-1,3-thiazolidine-4-carboxylic acid (Reference compound No. 10-52)

(2RS,4R)-3-[(2S)-3-Methyl-1-oxo-2-[[(phenoxymethyl)carbonyl]amino]butyl]-2-phenyl-1,3-thiazolidine-4-carboxylic acid (Reference compound No. 10-53)

(2RS,4R)-3-[(2S)-2-(tert-Butoxycarbonyl)amino-3-methyl-1-oxobutyl]-2-phenyl-1,3-thiazolidine-4-carboxylic acid (Reference compound No. 10-54)

(2RS,4R)-3-[(2S)-3-Methyl-1-oxo-2-[(phenoxycarbonyl)amino]butyl]-2-phenyl-1,3-thiazolidine-4-carboxylic acid (Reference compound No. 10-55)

(2RS,4R)-3-[(2S)-2-[[(4-Methoxyphenyl)methoxy]carbonyl]amino-3-methyl-1-oxobutyl]-2-phenyl-1,3-thiazolidine-4-carboxylic acid (Reference compound No. 10-56)

(2RS,4R)-3-[(2S)-2-[(N-Ethyl-N-methylamino)carbonyl]amino-3-methyl-1-oxobutyl]-2-phenyl-1,3-thiazolidine-4-carboxylic acid (Reference compound No. 10-57)
IR(Film,cm$^{-1}$): 3343,2927,1732,1651,1524.

(2RS,4R)-3-[(2S)-3-Methyl-2-[[(N-methyl-N-(phenylmethyl)amino)carbonyl]amino-1-oxobutyl]-2-phenyl-1,3-thiazolidine-4-carboxylic acid (Reference compound No. 10-58)

(2RS,4R)-3-[(2S)-2-[[N-[2-[(tert-Butoxycarbonyl)amino]ethyl]-N-methylamino]carbonyl]amino-1-oxobutyl]-2-phenyl-1,3-thiazolidine-4-carboxylic acid (Reference compound No. 10-59)
IR(KBr,cm$^{-1}$): 3358,2973,1645,1525,1170,755,722.

(2RS,4R)-3-[(2S)-2-[[4-[N-(tert-Butoxycarbonyl)-N-methylamino]piperidino]carbonyl]amino-1-oxobutyl]-2-phenyl-1,3-thiazolidine-4-carboxylic acid (Reference compound No. 10-60)
IR(Film,cm$^{-1}$): 3365,2966,1711,1666,1644,1529,1411,1323,1156.

(2RS,4R)-3-[(2S)-3-Methyl-2-[(4-methylpiperazino)carbonyl]-amino-1-oxobutyl]-2-phenyl-1,3-thiazolidine-4-carboxylic acid (Reference compound No. 10-61)
IR(KBr,cm$^{-1}$): 3414,2964,2688,1737,1643,1531,1461,1413,1267, 1183,753.

(2RS,4R)-3-[(2S)-2-[(Methoxymethyl)carbonyl]amino-1-oxopropyl]-2-phenyl-1,3-thiazolidine-4-carboxylic acid (Reference compound No. 10-62)

(2RS,4R)-3-[(2S)-2-[N-Methyl-N-[(phenylmethoxy)carbonyl]amino]- 1-oxopropyl]-2-phenyl-1,3-thiazolidine-4-carboxylic acid (Reference compound No. 10-63)

(2RS,4R)-3-[(2S)-2-[N-Ethyl-N-[(phenylmethoxy)carbonyl]amino]-1-oxopropyl]-2-phenyl-1,3-thiazolidine-4-carboxylic acid (Reference compound No. 10-64)

(2RS,4R)-2-Phenyl-3-[(2S)-1-[(phenylmethoxy)carbonyl]pyrrolidin-2-yl]carbonyl-1,3-thiazolidine-4-carboxylic acid (Reference compound No. 10-65)

(2RS,4R)-2-Phenyl-3-[(4R)-3-(phenylmethoxy)carbonyl-1,3-thiazolidin-4-yl]carbonyl-1,3-thiazolidine-4-carboxylic acid (Reference compound No. 10-66)

The following Reference Example 11 shows examples of the synthesis of the above-mentioned bicyclic carboxylic acid derivative [VII].

Reference Example 11
(2S)-2-[(Phenylmethoxy)carbonyl]aminoadipic acid (Reference compound No. 11-1a)

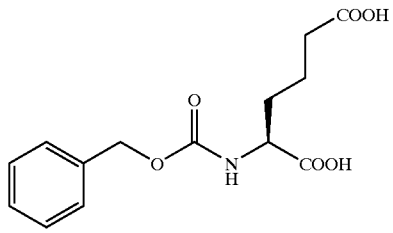

Benzyl chloroformate (5.3 ml) is added dropwise to a solution of (2S)-2-aminoadipic acid (5.00 g) in a 2 N aqueous sodium hydroxide solution (37.0 ml) under ice cooling, and the mixture is stirred for two hours. The reaction mixture is washed with diethyl ether, a 10% aqueous citric acid solution is added to the reaction mixture to acidify it, and the whole is extracted with ethyl acetate. The extract is washed with saturated brine and dried over anhydrous magnesium sulfate. The extract is concentrated under reduced pressure, and the resulting residue is washed with n-hexane to give 4.55 g of the titled compound.
mp 135.7–136.4° C.; IR(KBr,cm$^{-1}$): 3324,2966,1698, 1535,1462,1428,1353,1298,1249, 1203.

The following compounds are obtained by a method similar to the above-mentioned method.
(2S)-2-[(Phenylmethoxy)carbonyl]aminoglutaric acid (Reference compound No. 11-1b)
(2R)-2-[(Phenylmethoxy)carbonyl]aminoglutaric acid (Reference compound No. 11-1c)
mp 114.0–117.0° C.; [α] D$^{20}$ +7.4° (c=10.0, acetic acid); IR(KBr,cm$^{-1}$): 3307,3031,1704,1689,1586,1549,1527, 1499,1419, 1264,1214.
(2S)-2-[(Phenylmethoxy)carbonyl]aminosuccinic acid (Reference compound No. 11-1d)
(2R)-2-[(Phenylmethoxy)carbonyl]aminoadipic acid (Reference compound No. 11-1e)
mp 134.5–135.5° C.; [α] D$^{20}$ +9.3° (c=1.0, methanol); IR(KBr,cm$^{-1}$): 3324,2966,1693,1535,1461,1429,1353, 1278,1248, 1202,1175,1092,1055.
(2S)-2-[(Phenylmethoxy)carbonyl]aminoheptanedioic acid (Reference compound No. 11-1f)
(4S)-4-(3-Carboxypropyl)-3-[(phenylmethoxy)carbonyl]oxazolidin-5-one (Reference compound No. 11-2a)

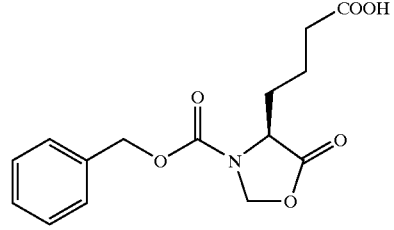

In toluene (50 ml) are suspended (2S)-2-[(phenylmethoxy)carbonyl]aminoadipic acid (2.95 g), paraformaldehyde (2.00 g) and p-toluenesulfonic acid monohydrate (0.01 g). Water is separated from this suspension by azeotropic distillation using a Dean-Stark apparatus over 35 minutes. After standing, the mixture is concentrated under reduced pressure to give 3.11 g of the titled compound as an oily matter.
IR(Film,cm$^{-1}$): 3033,2929,1801,1712,1498,1417,1359, 1317,1243, 1168,1050.

The following compounds are obtained by a method similar to the above-mentioned method.

(4S)-4-(2-Carboxyethyl)-3-[(phenylmethoxy)carbonyl] oxazolidin5-one (Reference compound No. 11-2b)
IR(Film,cm$^{-1}$): 3033,1800,1714,1498,1416,1359,1214, 1168,1132, 1054,1036.

(4R)-4-(2-Carboxyethyl)-3-[(phenylmethoxy)carbonyl] oxazolidin-5-one (Reference compound No. 11-2c)
IR(Film,cm$^{-1}$): 3033,1799,1714,1499,1417,1359,1214, 1168,1054.

(4S)-4-Carboxymethyl-3-[(phenylmethoxy)carbonyl] oxazolidin-5-one (Reference compound No. 11-2d)

(4R)-4-(3-Carboxypropyl)-3-[(phenylmethoxy)carbonyl] oxazolidin-5-one (Reference compound No. 11-2e)
IR(Film,cm$^{-1}$): 3032,2924,1802,1712,1498,1416,1359, 1316,1242, 1132,1050.

(4S)-4-(4-Carboxybutyl)-3-[(phenylmethoxy)carbonyl] oxazolidine-5-one (Reference compound No. 11-2f)

(4S)-4-[3-(Chloroformyl)propyl]-3-[(phenylmethoxy) carbonyl]oxazolidin-5-one (Reference compound No. 11-3a)

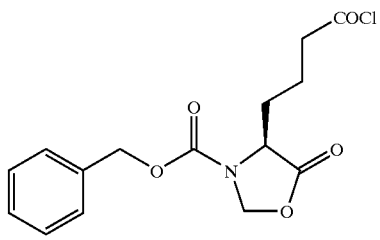

Thionyl chloride (20 ml) is added to (4S)-4-(3-carboxypropyl)- 3-[(phenylmethoxy)carbonyl]oxazolidin-5-one (2.90 g), and the mixture is refluxed for 45 minutes. After standing, the reaction mixture is concentrated under reduced pressure to give 2.70 g of the titled compound.
IR(Film,cm$^{-1}$): 2926,1799,1714,1587,1499,1453,1414, 1358,1243, 1170.

The following compounds are obtained by a method similar to the above-mentioned method.

(4S)-4-[2-(Chloroformyl)ethyl]-3-[(phenylmethoxy) carbonyl]oxazolidin-5-one (Reference compound No. 11-3b)
IR(Film,cm$^{-1}$): 3033,2924,1858,1797,1715,1498,1409, 1358,1174.

(4R)-4-[2-(Chloroformyl)ethyl]-3-[(phenylmethoxy) carbonyl]oxazolidin-5-one (Reference compound No. 11-3c)
IR(Film,cm$^{-1}$): 3033,2924,1857,1797,1716,1498,1410, 1357,1246, 1173,1130,1054.

(4S)-4-(Chloroformyl)methyl-3-[(phenylmethoxy) carbonyl]oxazolidin-5-one (Reference compound No. 11-3d)

(4R)-4-[3-(Chloroformyl)propyl]-3-[(phenylmethoxy) carbonyl]oxazolidin-5-one (Reference compound No. 11-3e)
IR(Film,cm$^{-1}$): 3033,2926,1858,1800,1716,1498,1454, 1415,1358, 1321,1243,1215,1170,1129,1049.

(4S)-4-[4-(Chloroformyl)butyl]-3-[(phenylmethoxy) carbonyl]oxazolidin-5-one (Reference compound No. 11-3f)

(4S)-4-(3-Formylpropyl)-3-[(phenylmethoxy)carbonyl] oxazolidin-5-one (Reference compound No. 11-4a)

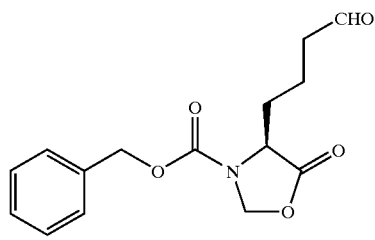

A solution of (4S)-4-[3-(chloroformyl)propyl]-3-[(phenylmethoxy)carbonyl]oxazolidin-5-one (2.65 g) in tetrahydrofuran (70 ml) is cooled with dry ice/methanol. A solution of lithium tri-tert-butoxyaluminohydride (2.07 g) in tetrahydrofuran (30 ml) is added dropwise thereto over one hour, and the mixture is stirred for 30 minutes. Raising temperature to room temperature, the mixture is stirred for one hour and then cooled with dry ice/methanol again. Water and ethyl acetate are added to the reaction mixture, insoluble matters are filtered out, and the filtrate is extracted with ethyl acetate. The extract is washed with saturated brine and dried over anhydrous magnesium sulfate. The extract is concentrated under reduced pressure, and the resulting residue is purified by silica gel column chromatography to give the titled compound.
IR(Film,cm$^{-1}$): 3032,2928,2726,1800,1717,1558,1498, 1455,1417, 1359,1318,1242.

The following compounds are obtained by a method similar to the above-mentioned method.

(4S)-4-(2-Formylethyl)-3-[(phenylmethoxy)carbonyl] oxazolidin-5 one (Reference compound No. 11-4b)
IR(Film,cm$^{-1}$): 3033,2927,1799,1713,1499,1415,1358, 12 14,1169, 1131,1051.

(4R)-4-(2-Formylethyl)-3-[(phenylmethoxy)carbonyl] oxazolidin-5-one (Reference compound No. 11-4c)
IR(Film,cm$^{-1}$): 3033,2923,2838,1798,1716,1652,1635, 1498,1455, 1417,1358,1307,1244.

(4S)-4-Formylmethyl-3-[(phenylmethoxy)carbonyl] oxazolidin-5-one (Reference compound No. 11-4d)

(4R)-4-(3-Formylpropyl)-3-[(phenylmethoxy)carbonyl] oxazolidin-5-one (Reference compound No. 11-4e)
IR(Film,cm$^{-1}$): 3467,3033,2925,2730,1798,1716,1499, 1417,1359, 1321,1243,1215,1167.

(4S)-4-(4-Formylbutyl)-3-[(phenylmethoxy)carbonyl] oxazolidin-5-one (Reference compound No. 11-4f)

(4S)-4-[3-[(2RS,4R)-(4-Methoxycarbonyl)thiazolidin-2-yl] propyl]-3-[(phenylmethoxy)carbonyl]oxazolidin-5-one (Reference compound No. 11-5a)

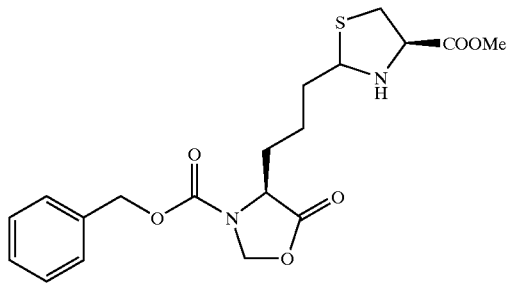

Sodium hydrogencarbonate (0.29 g) and water (5.0 ml) are added to a solution of (4S)-4-(3-formylpropyl)-3-[(phenylmethoxy)carbonyl]oxazolidin-5-one (0.93 g) and L-cysteine methyl ester hydrochloride (0.60 g) in tetrahydrofuran (30 ml), and the mixture is stirred at room temperature overnight. The reaction mixture is concentrated under reduced pressure, water is added to the resulting residue, and the whole is extracted with chloroform. The extract is washed with saturated brine and dried over anhydrous magnesium sulfate. The extract is concentrated under reduced pressure to give 1.21 g of the titled compound.

IR(Film,cm$^{-1}$): 3306,2950,1799,1716,1498,1415,1357, 1321,1213, 1167,1129.

The following compounds are obtained by a method similar to the above-mentioned method.

(4S)-4-[2-[(2RS,4R)-(4-Methoxycarbonyl)thiazolidin-2-yl] ethyl]-3-[(phenylmethoxy)carbonyl]oxazolidin-5-one (Reference compound No. 11-5b)

(4R)-4-[2-[(2RS,4R) -(4-Methoxycarbonyl)thiazolidin-2-yl] ethyl]-3-[(phenylmethoxy)carbonyl]oxazolidin-5-one (Reference compound No. 11-5c)

(4S)-4-[(2RS,4R)-(4-Methoxycarbonyl)thiazolidin-2-yl] methyl-3[(phenylmethoxy)carbonyl]oxazolidin-5-one (Reference compound No. 11-5d)

(4R)-4-[3-[(2RS,4R)-(4-Methoxycarbonyl)thiazolidin-2-yl] propyl]-3-[(phenylmethoxy)carbonyl]oxazolidin-5-one (Reference compound No. 11-5e)

IR(Film,cm$^{-1}$): 3305,3026,2952,1800,1715,1498,1416, 1358,1324, 1215,1168,1130,1051.

(4S)-4-[4-[(2RS,4R)-(4-Methoxycarbonyl)thiazolidin-2-yl] butyl]-3-[(phenylmethoxy)carbonyl]oxazolidin-5-one (Reference compound No. 11-5f)

Methyl (3S,7RS,10R)-1-aza-2-oxo-3-[(phenylmethoxy) carbonyl]amino-8-thiabicyclo[5.3.0]decane-10-carboxylate (Reference compound No. 11-6a)

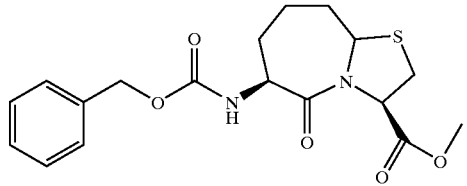

A solution of (4S)-4-[3-[(2RS,4R)-(4-methoxycarbonyl) thiazolidin-2-yl]propyl]-3-[(phenylmethoxy)carbonyl] oxazolidin-5-one (1.1 g) in dioxane (20 ml) is refluxed overnight. After standing, ethyl acetate is added to the reaction mixture, and the whole is washed with a 1 N aqueous sodium hydroxide solution, a 10% aqueous citric acid solution and saturated brine successively. The washed liquid is dried over magnesium sulfate and concentrated under reduced pressure. The resulting residue is purified by silica gel column chromatography to give 0.37 g of the titled compound.

IR(Film,cm$^{-1}$): 3298,2952,1800,1712,1498,1415,1359, 1221,1169, 1130,1050.

The following compounds are obtained by a method similar to the above-mentioned method.

Methyl (3S,6RS,9R)-1-aza-2-oxo-3-[(phenylmethoxy) carbonyl]amino-7-thiabicyclo[4.3.0]nonane-9-carboxylate (Reference compound No. 11-6b)

Methyl (3R,6RS,9R)-1-aza-2-oxo-3-[(phenylmethoxy) carbonyl]amino-7-thiabicyclo[4.3.0]nonane-9-carboxylate (Reference compound No. 11-6c)

Methyl (3S,5RS,8R)-1-aza-2-oxo-3-[(phenylmethoxy) carbonyl]amino-6-thiabicyclo[3.3.0]octane-8-carboxylate (Reference compound No. 11-6d)

Methyl (3R,7RS,10R)-1-aza-2-oxo-3-[(phenylmethoxy) carbonyl]amino-8-thiabicyclo[5.3.0]decane-10-carboxylate (Reference compound No. 11-6e)

IR(Film,cm$^{-1}$): 3296,2951,1800,1715,1498,1416,1358, 1324,1214, 1169,1129,1050.

Methyl (3S,8RS,11R)-1-aza-2-oxo-3-[(phenylmethoxy) carbonyl]amino-9-thiabicyclo[6.3.0]undecane-11-carboxylate (Reference compound No. 11-6f)

(3S,7RS,10R)-1-Aza-2-oxo-3-[(phenylmethoxy)carbonyl] amino-8-thiabicyclo[5.3.0]decane-10-carboxylic acid (Reference compound No. 11-7a)

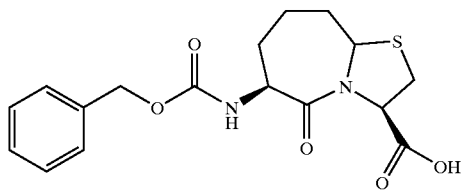

A 4 N aqueous lithium hydroxide solution (0.63 ml) is added dropwise to a solution of methyl (3S,7RS,10R)-1-aza-2-oxo-3-[(phenylmethoxy)carbonyl]amino-8-thiabicyclo[5.3.0]decane-10-carboxylate (0.32 g) in methanol (10 ml)/tetrahydrofuran (5.0 ml), and the mixture is stirred for 10 minutes. Under ice cooling,2 N hydrochloric acid is added to the reaction mixture to acidify it. The whole is concentrated under reduced pressure, and the residue is extracted with ethyl acetate. The extract is washed with saturated brine and dried over anhydrous magnesium sulfate. The extract is concentrated under reduced pressure to give 0.28 g of the titled compound.

IR(KBr,cm$^{-1}$): 3366,2956,1716,1527,1455,1411,1305, 1231,1140, 1119,1044.

The following compounds are obtained by a method similar to the above-mentioned method.

(3S,6RS,9R)-1-Aza-2-oxo-3-[(phenylmethoxy)carbonyl] amino-7-thiabicyclo[4.3.0]nonane-9-carboxylic acid (Reference compound No. 11-7b)

IR(KBr,cm$^{-1}$): 3324,2950,1958,1724,1659,1529,1438, 1344,1312, 1251,1083,1059.

(3R,6RS,9R)-1-Aza-2-oxo-3-[(phenylmethoxy)carbonyl] amino-7-thiabicyclo[4.3.0]nonane-9-carboxylic acid (Reference compound No. 11-7c)

IR(KBr,cm$^{-1}$): 3480,2939,2584,1740,1718,1607,1462, 1441,1348, 1313,1259,1196,1149.

(3S,5RS,8R)-1-Aza-2-oxo-3-[(phenylmethoxy)carbonyl] amino-6-thiabicyclo[3.3.0]octane-8-carboxylic acid (Reference compound No. 11-7d)

(3R,7RS,10R)-1-Aza-2-oxo-3-[(phenylmethoxy)carbonyl] amino-8-thiabicyclo[5.3.0]decane-10-carboxylic acid (Reference compound No. 11-7e)

IR(Film,cm$^{-1}$): 2934,1711,1531,1412,1345,1231,1119, 1067.

(3S,8RS,11R)-1-Aza-2-oxo-3-[(phenylmethoxy)carbonyl] amino-9-thiabicyclo[6.3.0]undecane-11-carboxylic acid (Reference compound No. 11-7f)

The following Reference Examples 12 to 15 show examples of the synthesis of the amino alcohol derivative [VI] shown in the above synthesis route scheme.

Reference Example 12

(2S)-2-(tert-Butoxycarbonyl)amino-3-phenyl-1-propanol (Reference compound No. 12-1)

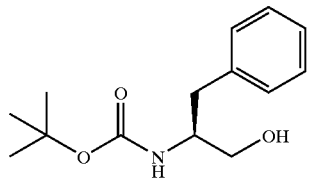

A solution of di-tert-butyl dicarbonate (1.44 g) in tetrahydrofuran is added dropwise to a solution of (S)-2-amino-3-phenyl-1-propanol (1.00 g) in tetrahydrofuran (15 ml), and the mixture is stirred for 30 minutes. Then, the reaction mixture is concentrated under reduced pressure, and the resulting residue is purified by silica gel column chromatography to give 1.70 g of the titled reference compound.

mp 95.2–96.7° C.; [α] $D^{20}$ −26.9° (c=1.0, methanol); IR(KBr,cm$^{-1}$): 3355,1688,1529,1444,1367,1316,1270, 1252,1169, 1006,702.

(2S)-2-(tert-Butoxycarbonyl)amino-3-phenyl-1-propanal (Reference compound No. 12-2)

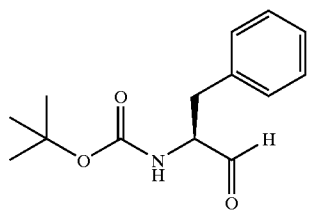

Triethylamine (17 ml) is added to a solution of (2S)-2-(tert-butoxycarbonyl)amino-3-phenyl-1-propanol (5.00 g) in dimethyl sulfoxide (100 ml). A sulfur trioxide-pyridine complex (11.1 g) is added to the mixture, and the whole is stirred for 40 minutes. Then, water is added to the reaction mixture, and the whole is extracted with diethyl ether. The extract is washed with a saturated aqueous ammonium chloride solution, water, a saturated aqueous sodium hydrogencarbonate solution and saturated brine successively and dried over anhydrous magnesium sulfate. The extract is concentrated under reduced pressure, and the resulting residue is purified by silica gel column chromatography to give 4.48 g of the titled compound.

IR(KBr,cm$^{-1}$): 1731,1672,1561.

(2RS,3S)-3-(tert-Butoxycarbonyl)amino-2-hydroxy-4-phenylbutanenitrile (Reference compound No. 12-3)

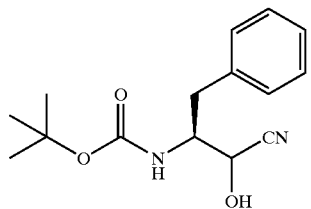

A solution of sodium hydrogensulfite (0.92 g) in water (5 ml) is added dropwise to a suspension of (2S)-2-(tert-butoxycarbonyl)amino-3-phenyl-1-propanal (2.00 g) in water (20 ml) under ice cooling. Raising temperature to room temperature, the mixture is stirred overnight. Ethyl acetate (100 ml) is added to this suspension, and the whole is stirred at room temperature for one hour. Then, a solution of potassium cyanide (0.58 g) in water (5 ml) is added thereto, and the whole is stirred at room temperature for four hours. The reaction mixture is extracted with ethyl acetate, and the extract is washed with saturated brine. The extract is dried over anhydrous magnesium sulfate and concentrated under reduced pressure, and the resulting residue is recrystallized to give 1.18 g of the titled compound.

Isopropyl (2RS,3S)-3-amino-2-hydroxy-4-phenylbutyrate (Reference compound No. 12-4)

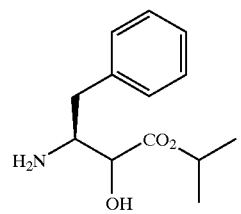

A solution of (2RS,3S)-3-(tert-butoxycarbonyl)amino-2-hydroxy-4-phenylbutanenitrile (1.00 g) in isopropanol (40 ml) is saturated with hydrogen chloride under ice cooling. Raising temperature to room temperature, the mixture is stirred overnight. This reaction mixture is concentrated under reduced pressure,0.1 N hydrochloric acid is added to the resulting residue, and the whole is stirred at room temperature for 20 minutes. The reaction mixture is washed with diethyl ether, a saturated aqueous sodium hydrogencarbonate solution is added to the reaction mixture to basify it, and the whole is extracted with ethyl acetate. The extract is washed with water and saturated brine successively, dried over anhydrous magnesium sulfate and concentrated under reduced pressure to give 0.54 g of the titled compound.

Reference Example 13

Phenylmethyl (2RS,3S)-3-amino-2-hydroxy-4-phenylbutyrate hydrogen p-toluenesulfonate (Reference compound No. 13-1)

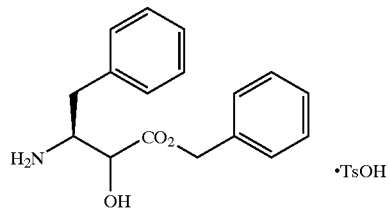

Water and isopropanol are separated from a solution of isopropyl (2RS,3S)-3-amino-2-hydroxy-4-phenylbutyrate (1.42 g), p-toluenesulfonic acid monohydrate (1.37 g) and benzyl alcohol (6 ml) in benzene (20 ml) by azeotropic distillation overnight using a Dean-Stark apparatus. Diethyl ether is added to the reaction mixture, and precipitated crystals are filtered off to give 1.68 g of the titled compound.

mp 135.0–150.0° C.; IR(KBr,cm$^{-1}$): 3335,2923,1742, 1631,1499,1172,1125,1037,1012, 815,699,679.

Reference Example 14
(4RS)-2-Phenyl-4-phenylmethyl-5(4 H)-oxazolone (Reference compound No. 14-1)

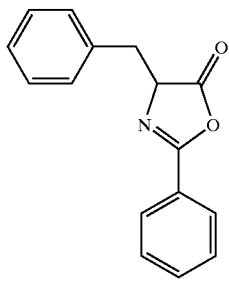

A suspension of N-benzoyl-DL-phenylalanine (5.9 g) in acetic anhydride (12.3 g) is stirred at 80° C. under a nitrogen atmosphere for 40 minutes. Then, the reaction mixture is concentrated under reduced pressure, and the resulting residue is recrystallized to give 4.30 g of the titled compound.

mp 70.0–72.0° C.; IR(KBr,cm$^{-1}$): 1826,181,1647,1297, 1079,1048,902,695.

(3RS)-2-Oxo-4-phenyl-3-(phenylcarbonyl)amino-1,1,1-trifluorobutane (Reference compound No. 14-2)

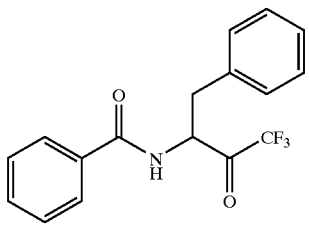

A solution of (4RS)-2-phenyl-4-phenylmethyl-5(4 H)-oxazolone (3.65 g) in trifluoroacetic anhydride (6.13 g) is stirred under a nitrogen atmosphere for one day. The reaction mixture is concentrated under reduced pressure, and oxalic acid (1.97 g) is added to the resulting residue. The whole is heated up to 120° C. gradually and stirred for 30 minutes. After ice cooling, water is added to the reaction mixture, and the whole is extracted with ethyl acetate. The extract is washed with water, a saturated aqueous sodium hydrogencarbonate solution and saturated brine successively and dried over anhydrous magnesium sulfate. The extract is concentrated under reduced pressure, and the resulting residue is recrystallized to give 3.23 g of the titled compound.

mp 148.5–157.0° C.; IR(KBr,cm$^{-1}$): 3344,1763,1654, 1624,1554,1166,1110,695.

(2RS,3RS)-2-Hydroxy-4-phenyl-3-(phenylcarbonyl)amino-1,1,1-trifluorobutane (Reference compound No. 14-3)

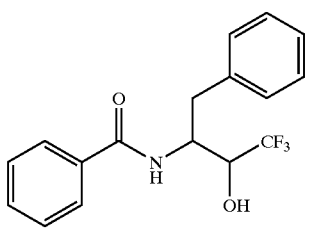

Sodium borohydride (0.37 g) is added to a solution of (3RS)-2-oxo-4-phenyl-3-(phenylcarbonyl)amino-1,1,1-trifluorobutane (3.12 g) in ethanol (25 ml), and the mixture is stirred at 35° C. for four hours. Under ice cooling, 6 N hydrochloric acid is added dropwise to the reaction mixture, and the whole is extracted with ethyl acetate. The extract is washed with water, a saturated aqueous sodium hydrogencarbonate solution and saturated brine successively and dried over anhydrous magnesium sulfate. The extract is concentrated under reduced pressure to give 3.00 g of the titled compound.

mp 176.0–183.0° C.; IR(KBr,cm$^{-1}$): 3309,1646,1538, 1237,1261,1190,1133,699.

(2RS,3RS)-3-Amino-2-hydroxy-4-phenyl-1,1,1-trifluorobutane hydrochloride (Reference compound No. 14-4)

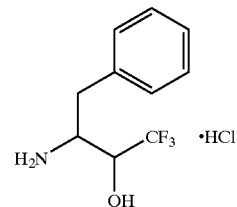

12 N hydrochloric acid (120 ml) is added to a suspension of (2RS,3RS)-2-hydroxy-4-phenyl-3-(phenylcarbonyl)amino-1,1,1-trifluorobutane (3.00 g) in ethanol (60 ml) and water (60 ml), and the mixture is refluxed for one day. After standing, the reaction mixture is concentrated under reduced pressure, diethyl ether is added to the resulting residue, and the whole is extracted with water. The extract is concentrated under reduced pressure, and the resulting residue is crystallized with ethyl acetate/hexane to give 1.58 g of the titled compound.

mp 218.0–226.0° C.; IR(KBr,cm$^{-1}$): 3318,3128,2924, 1601,1513,1285,1181,1156.

Reference Example 15
(1RS,2S)-1-(2-Benzothiazolyl)-2-(tert-butoxycarbonyl)amino-3-phenyl-1-propanol (Reference compound No. 15-1a)

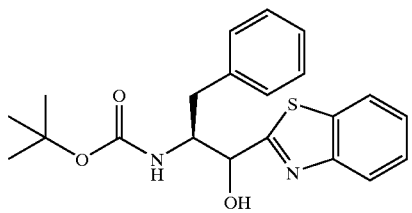

A solution of benzothiazole (0.74 g) in tetrahydrofuran (10 ml) is cooled with dry ice/methanol under a nitrogen atmosphere. A 1.6 M n-butyllithium/hexane solution (3.5 ml) is added dropwise thereto, and the mixture is stirred for 30 minutes. To this mixture is added dropwise a solution of (2S)-2-(tert-butoxycarbonyl)amino-3-phenyl-1-propanal (1.25 g) in tetrahydrofuran (10 ml), and the whole is further stirred for four hours. A saturated aqueous ammonium chloride solution is added dropwise to the reaction mixture, temperature is raised to room temperature, and the whole is stirred for 30 minutes. This reaction mixture is extracted with ethyl acetate, and the extract is washed with water and saturated brine successively and dried over anhydrous magnesium sulfate. The extract is concentrated under reduced pressure, and the resulting residue is purified by silica gel column chromatography to give 0.93 g of the titled compound.

IR(KBr,cm$^{-1}$): 3338,1691,1497,1392,1367,1168,759, 700.

The following compounds are obtained by a method similar to the above-mentioned method.

(1RS,2S)-2-(tert-Butoxycarbonyl)amino-3-phenyl-1-(2-thiazolyl)-1-propanol (Reference compound No. 15-1b)
(1RS,2S)-1-(2-Benzoxazolyl)-2-(tert-butoxycarbonylamino)-3-phenyl-1-propanol (Reference compound No. 15-1c)
(1RS,2S)-2-(tert-Butoxycarbonylamino)-1-(2-oxazolyl)-3-phenyl-1-propanol (Reference compound No. 15-1d)
(1RS,2S)-2-Amino-1-(2-benzothiazolyl)-3-phenyl-1-propanol Hydrochloride (Reference compound No. 15-2a)

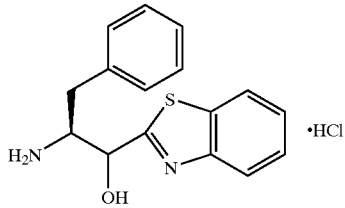

A 4 M hydrogen chloride/dioxane solution (6.3 ml) is added dropwise to (1RS,2S)-1-(2-benzothiazolyl)-2-(tert-butoxycarbonyl)amino-3-phenyl-1-propanol (0.64 g) under ice cooling, temperature is raised to room temperature, and the mixture is stirred for 30 minutes. The reaction mixture is concentrated under reduced pressure, and the residue is washed with ether to give 0.56 g of the titled compound.

IR(KBr,cm$^{-1}$): 2857,1600,1495,1454,1117,1067,759, 700.

The following compounds are obtained by a method similar to the above-mentioned method.
(1RS,2S)-2-Amino-3-phenyl-1-(2-thiazolyl)-1-propanol hydrochloride (Reference compound No. 15-2b)
(1RS,2S)-2-Amino-1-(2-benzoxazolyl)-3-phenyl-1-propanol hydrochloride (Reference compound No. 15-2c)
(1RS,2S)-2-Amino-1-(2-oxazolyl)-3-phenyl-1-propanol hydrochloride (Reference compound No. 15-2d)

EXAMPLES

Preparation of Compounds

Example 1

Isopropyl (2RS,3S)-2-hydroxy-3-[(4R)-3-[(2S)-3-methyl-1-oxo-2-[[(phenylmethoxy)carbonyl]amino]butyl]-1,3-thiazolidin-4-ylcarboxamido]-4-phenylbutyrate (Compound No.1-1)

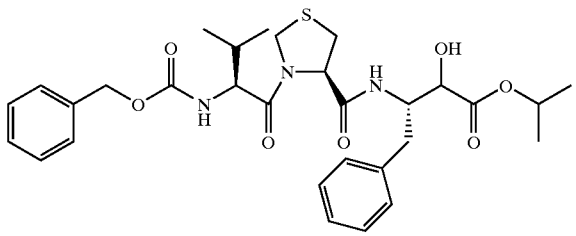

1-Hydroxybenzotriazole (0.27 g) is added to a solution of (4R)-3-[(2S)-3-methyl-1-oxo-2-[[(phenylmethoxy)carbonyl]amino]butyl]-1,3-thiazolidine-4-carboxylic acid (0.50 g) and isopropyl (2RS,3S)-3-amino-2-hydroxy-4-phenylbutyrate (0.32 g) in methylene chloride. 1-Ethyl-3-(3-dimethylaminopropyl)carbodiimide hydrochloride (0.33 g) is added thereto under ice cooling, temperature is raised to room temperature, and the mixture is stirred overnight. The reaction mixture is concentrated under reduced pressure, a 5% aqueous citric acid solution is added to the concentrate, and the whole is extracted with ethyl acetate. The extract is washed with a saturated aqueous sodium hydrogencarbonate solution, water and saturated brine successively. The extract is dried over anhydrous magnesium sulfate and concentrated under reduced pressure. The residue is purified by silica gel column chromatography to give 0.82 g of the titled compound.

$[\alpha]_D^{20}$ −100.7° (c=0.5, methanol); IR(Film,cm$^{-1}$): 3325, 1721,1642,1526,1427,1220,1105,754.

The following compounds are obtained by a method similar to Example 1.
Isopropyl (2RS,3S)-2-hydroxy-3-[(4R)-3-[1-oxo-2-[[(phenylmethoxy)carbonyl]amino]ethyl]-1,3-thiazolidin-4-ylcarboxamido]-4-phenylbutyrate (Compound No. 1-2)

$[\alpha]_D^{20}$ −83.7° (c=0.5, methanol) IR(Film,cm$^{-1}$): 3324, 1724,1663,1528,1259,1105,754,700.
Isopropyl (2RS,3S)-2-hydroxy-3-[(4R)-3-[(2S)-1-oxo-2-[[(phenylmethoxy)carbonyl]amino]propyl]- 1,3-thiazolidin-4-ylcarboxamido]-4-phenylbutyrate (Compound No. 1-3)

$[\alpha]_D^{20}$ −114.0° (c=0.5, methanol); IR(Film,cm$^{-1}$): 3323, 1722,1657,1527,1454,1259,1105,753.
Isopropyl (2RS,3S)-2-hydroxy-3-[(4R)-3-[(2S)-1-oxo-2-[[(phenylmethoxy)carbonyl]amino]butyl]-1,3-thiazolidin-4-ylcarboxamido]-4-phenylbutyrate (Compound No. 1-4)
Isopropyl (2RS,3S)-2-hydroxy-3-[(4R)-3-[(2S)-4-methyl-1-oxo-2-[[(phenylmethoxy)carbonyl]amino]pentyl]-1,3-thiazolidin-4-ylcarboxamido]-4-phenylbutyrate (Compound No. 1-5)

IR(Film,cm$^{-1}$): Rf (large) 3402,2958,1651,1532,1455, 1259,1105,753,700, Rf (small) 3323,2958,1724,1529,1426, 1260,1106,754,699.
Isopropyl (2RS,3S)-2-hydroxy-3-[(4R)-3-[(2S,3RS)-3-methyl-1-oxo-2-[[(phenylmethoxy)carbonyl]amino]pentyl]-1,3-thiazolidin-4-ylcarboxamido]-4-phenylbutyrate (Compound No. 1-6)

IR(Film,cm$^{-1}$): 3325,2968,1714,1519,1428,1219,1105, 754,700.
Isopropyl (2RS,3S)-3-[(4R)-3-[(2S)-3,3-dimethyl-1-oxo-2-[[(phenylmethoxy)carbonyl]amino]butyl]-1,3--thiazolidin-4-ylcarboxamido]-2-hydroxy-4-phenylbutyrate (Compound No. 1-7)
Isopropyl (2RS,3S)-2-hydroxy-3-[(4R)-3-[(2S)-1-oxo-2-phenyl-2-[[(phenylmethoxy)carbonyl]amino]ethyl]-1,3-thiazolidin-4-ylcarboxamido]-4-phenylbutyrate (Compound No. 1-8)

mp 121.0–136.0° C.; $[\alpha]_D^{20}$ −81.7° (c=0.5, methanol); IR(KBr,cm$^{-1}$); Rf (large) 3397,3360,3271,1728,1648, 1491,1408,702, Rf (small) 3398,1739,1661,1522,1403, 1264,1105,698.
Isopropyl (2RS,3S)-2-hydroxy-3-[(4R)-3-[(2S)-1-oxo-3-phenyl-2-[[(phenylmethoxy)carbonyl]amino]propyl]-1,3-thiazolidin-4-ylcarboxamido]-4-phenylbutyrate (Compound No. 1-9)

IR(Film,cm$^{-1}$): 3315,3028,2979,1723,1689,1528,1453, 1374,1259, 1105.
Isopropyl (2RS,3S)-2-hydroxy-3-[(4R)-3-[(2RS)-1-oxo-6-phenyl-2[[(phenylmethoxy)carbonyl]amino]hexyl]-1,3-thiazolidin-4-ylcarboxamido]-4-phenylbutyrate (Compound No. 1-10)
Isopropyl (2RS,3S)-2-hydroxy-3-[(4R)-3-[(2S)-3-(4-hydroxyphenyl)-1-oxo-2-[[(phenylmethoxy)carbonyl]amino]propyl]-1,3-thiazolidin-4-ylcarboxamido]-4-phenylbutyrate (Compound No. 1-11)

IR(KBr,cm$^{-1}$); Rf (large) 3308,3063,3029,2980,2935, 1727,1652,1614,1595,1516, 1454,1374,1261,1179, Rf (small) 3306,3063,3029,2979,2937,1720,1651,1515,1427, 1374,1250,1163,1049,1027.

Isopropyl (2RS,3S)-2-hydroxy-3-[(4R)-3-[(2S)-1-oxo-2-[(phenylmethoxy)carbonyl]amino-3-[-1-(triphenylmethyl)imidazol-5-yl]propyl]-1,3-thiazolidin-4-ylcarboxamido]-4-phenylbutyrate (Compound No. 1-12)

IR(KBr,cm$^{-1}$): 3291,3060,3029,2979,1727,1660,1494, 1444,1374, 1214,1128,1105.

Isopropyl (2RS,3S)-2-hydroxy-3-[(4R)-3-[(2S)-1-oxo-2-[(phenylmethoxy)carbonyl]amino-3-[1-(triphenylmethyl)indol-3-yl]propyl]-1,3-thiazolidin-4-ylcarboxamido]-4-phenylbutyrate (Compound No. 1-13)

Isopropyl (2RS,3S)-3-[(4R)-3-[(2S)-3-(tert-butoxy)-1-oxo-2-[[(phenylmethoxy)carbonyl]amino]propyl]-1,3-thiazolidin-4-ylcarboxamido]-2-hydroxy-4-phenylbutyrate (Compound No. 1-14)

IR(Film,cm$^{-1}$): 3322,2976,1728,1660,1529,1263,1217, 1108,754, 700.

Isopropyl (2RS,3S)-3-[(4R)-3-[(2S)-3-(tert-butoxycarbonyl)-1-oxo-2-[[(phenylmethoxy)carbonyl]amino]propyl]-1,3-thiazolidin-4-ylcarboxamido]-2-hydroxy-4-phenylbutyrate (Compound No. 1-15)

Isopropyl (2RS,3S)-2-hydroxy-3-[(4R)-3-[(2S)-3-methyl-2-(methylcarbonyl)amino-1-oxobutyl]-1,3-thiazolidin-4-ylcarboxamido]-4-phenylbutyrate (Compound No. 1-16) mp 108.0–118.0° C.; $[\alpha]_D^{20}$ −49.9° (c=0.5, methanol);

IR(KBr,cm$^{-1}$): Rf (large) 3339,1736,1663,1633,1547, 1414,1292,1105, Rf (small) 3293,1745,1679,1531,1408, 1286,1176,1109.

Isopropyl (2RS,3S)-2-hydroxy-3-[(4R)-3-[(2S)-3-methyl-1-oxo-2-[[(phenylmethyl)carbonyl]amino]butyl]-1,3-thiazolidin-4-ylcarboxamido]-4-phenylbutyrate (Compound No. 1-17)

Isopropyl (2RS,3S)-2-hydroxy-3-[(4R)-3-[(2S)-3-methyl-1-oxo-2-[[(2-phenylethyl)carbonyl]amino]butyl]- 1,3-thiazolidin-4-ylcarboxamido]-4-phenylbutyrate (Compound No.1-18)

Isopropyl (2RS,3S)-2-hydroxy-3-[(4R)-3-[(2S)-2-[(methoxymethyl)carbonyl]amino-3-methyl-1-oxobutyl]-1,3-thiazolidin-4-ylcarboxamido]-4-phenylbutyrate (Compound No. 1-19)

IR(Film,cm$^{-1}$): 3323,2970,1734,1649,1524,1429,1204, 1108,753, 702.

Isopropyl (2RS,3S)-2-hydroxy-3-[(4R)-3-[(2S)-3-methyl-1-oxo-2-[[(phenoxymethyl)carbonyl]amino]butyl]-1,3-thiazolidin-4-ylcarboxamido]-4-phenylbutyrate (Compound No. 1-20)

IR(Film,cm$^{-1}$): 3323,3063,3013,2970,2935,2874,1730, 1660,1599, 1527,1495,1440,1217,1105.

Isopropyl (2RS,3S)-3-[(4R)-3-[(2S)-2-(tert-butoxycarbonyl)amino-3-methyl-1-oxobutyl]-1,3-thiazolidin-4-ylcarboxamido]-2-hydroxy-4-phenylbutyrate (Compound No. 1-21)

$[\alpha]_D^{20}$ −123.7° (c=0.6, methanol); IR(KBr,cm$^{-1}$): 3350, 1697,1519,1426,1368,1255,1170,1105.

Isopropyl (2RS,3S)-2-hydroxy-3-[(4R)-3-[(2S)-3-methyl-1-oxo-2-[(phenoxycarbonyl)amino]butyl]-1,3-thiazolidin-4-ylcarboxamido]-4-phenylbutyrate (Compound No. 1-22)

Isopropyl (2RS,3S)-2-hydroxy-3-[(4R)-3-[(2S)-2-[[(4-methoxyphenyl)methoxy]carbonyl]amino-3-methyl-1-oxobutyl]-1,3-thiazolidin-4-ylcarboxamido]-4-phenylbutyrate (Compound No. 1-23)

IR(Film,cm$^{-1}$): 3321,2964,2935,1716,1694,1639,1586, 1515,1465, 1454,1429,1248.

Isopropyl (2RS,3S)-3-[(4R)-3-[(2S)-2-[(N-ethyl-N-methylamino)carbonyl]amino-3-methyl-1-oxobutyl]-1,3-thiazolidin-4-ylcarboxamido]-2-hydroxy-4-phenylbutyrate (Compound No. 1-24)

Isopropyl (2RS,3S)-2-hydroxy-3-[(4R)-3-[(2S)-3-methyl-2-[[N-methyl-N-(phenymethyl)amino]carbonyl]amino-1-oxobutyl]-1,3-thiazolidin-4-ylcarboxamido]-4-phenylbutyrate (Compound No. 1-25)

IR(Film,cm$^{-1}$): Rf (large) 3337,2969,1733,1631,1524, 1424,1217,1106,752,700, Rf (small) 3222,2978,1737,1634, 1519,1423,1217,1106,752.

Isopropyl (2RS,3S)-3-[(4R)-3-[(2S)-2-[[N-[2-[(tert-butoxycarbonyl)amino]ethyl]-N-methylamino]carbonyl]amino-3-methyl-1-oxobutyl]-1,3-thiazolidin-4-ylcarboxamido]-2-hydroxy-4-phenylbutyrate (Compound No. 1-26)

IR(Film,cm$^{-1}$): 3339,2978,1735,1691,1635,1525,1427, 1366,1251, 1172,1105.

Isopropyl (2RS,3S)-3-[(4R)-3-[(2S)-2-[[4-[N-(tert-butoxycarbonyl)-N-methylamino]piperidino]carbonyl]amino-3-methyl-1-oxobutyl]-1,3-thiazolidin-4-ylcarboxamido]-2-hydroxy-4-phenylbutyrate (Compound No. 1-27)

IR(Film,cm$^{-1}$): 3339,2973,2874,1828,1733,1691,1628, 1531.

Isopropyl (2RS,3S)-2-hydroxy-3-[(4R)-3-[(2S)-3-methyl-2-[(4-methylpiperazino)carbonyl]amino-1-oxobutyl]-1,3-thiazolidin-4-ylcarboxamido]-4-phenylbutyrate hydrochloride (Compound No. 1-28)

Isopropyl (2RS,3S)-2-hydroxy-3-[(4R)-3-[(2S)-2-[(methoxymethyl)carbonyl]amino-1-oxopropyl]-1,3-thiazolidin-4-ylcarboxamido]-4-phenylbutyrate (Compound No. 1-29)

$[\alpha]_D^{20}$ −149.4° (c=0.5, methanol); IR(Film,cm$^{-1}$): 3324, 1732,1649,1529,1454,1426,1107,754.

Isopropyl (2RS,3S)-2-hydroxy-3-[(4R)-3-[(2S)-2-[N-methyl-N-[(phenylmethoxy)carbonyl]amino]-1-oxopropyl]-1,3-thiazolidin-4-ylcarboxamido]-4-phenylbutyrate (Compound No. 1-30)

Isopropyl (2RS,3S)-3-[(4R)-3-[(2S)-2-[N-ethyl-N-[(phenylmethoxy)carbonyl]amino]-1-oxopropyl]-1,3-thiazolidin-4-ylcarboxamido]-2-hydroxy-4-phenylbutyrate (Compound No. 1-31)

Isopropyl (2RS)-2-hydroxy-3-[(4R)-3-[(2RS)-1-oxo-6-phenyl-2-[[(phenylmethoxy)carbonyl]amino]hexyl]-1,3-thiazolidin-4-ylcarboxamido]propionate (Compound No. 1-32)

IR(Film,cm$^{-1}$): 3323,3027,2935,1653,1536,1420,1384, 1258,1104.

Isopropyl (2RS,3S)-2-hydroxy-4-phenyl-3-[(4R)-3-[(4R)-3-(phenylmethoxy)carbonyl-1,3-thiazolidin-4-yl]carbonyl-1,3-thiazolidin-4-ylcarboxamido]butyrate (Compound No. 1-33)

IR(Film,cm$^{-1}$): 3322,3062,3029,2979,1689,1526,1416, 1356,1106.

Isopropyl (2RS,3S)-2-hydroxy-4-phenyl-3-[(4R)-3-[(4R)-3-(phenylmethoxy)carbonyl-1,3-thiazolidin-4-yl]carbonyl-1,3-thiazolidin-4-ylcarboxamido]butyrate (Compound No. 1-34)

(2RS,3RS)-2-Hydroxy-3-[(4R)-3-[(2S)-3-methyl-1-oxo-2-[[(phenylmethoxy)carbonyl]amino]butyl]-1,3-thiazolidin-4-ylcarboxamido]-4-phenyl-1,1,1-trifluorobutane (Compound No. 1-35)

(2RS,3RS)-3-[(4R)-3-[(2S)-2-(tert-Butoxycarbonyl)amino-3-methyl-1-oxobutyl]-1,3-thiazolidin-4-ylcarboxamido]-2-hydroxy-4-phenyl-1,1,1-trifluorobutane (Compound No. 1-36)

Phenylmethyl (2RS,3S)-2-hydroxy-3-[(4R)-3-[(2S)-3-methyl-1-oxo-2-[[(phenylmethoxy)carbonyl]amino]

butyl]-1,3-thiazolidin-4-ylcarboxamido]-4-phenylbutyrate (Compound No. 1-37)
IR(Film,cm$^{-1}$): 3787,3324,2964,1722,1691,1642,1519.

Phenylmethyl (2RS,3S)-3-[(4R)-3-[(2S)-2-(tert-butoxycarbonyl)amino-3-methyl-1-oxobutyl]-1,3-thiazolidin-4-ylcarboxamido]-2-hydroxy-4-phenylbutyrate (Compound No. 1-38)

(1RS,2S)-1-Hydroxy-2-[(4R)-3-[(2S)-3-methyl-1-oxo-2-[[(phenylmethoxy)carbonyl]amino]butyl]-1,3-thiazolidin-4-ylcarboxamido]-1-(2-oxazolyl)-3-phenylpropane (Compound No. 1-39)

(1RS,2S)-2-[(4R)-3-[(2S)-2-(tert-Butoxycarbonyl)amino-3-methyl-1-oxobutyl]-1,3-thiazolidin-4-ylcarboxamido]-1-hydroxy-1-(2-oxazolyl)-3-phenylpropane (Compound No. 1-40)

(1RS,2S)-1-(2-Benzoxazolyl)-1-hydroxy-2-[(4R)-3-[(2S)-3-methyl-1-oxo-2-[[(phenylmethoxy)carbonyl]amino]butyl]-1,3-thiazolidin-4-ylcarboxamido]-3-phenylpropane (Compound No. 1-41)

(1RS,2S)-1-(2-Benzoxazolyl)-2-[(4R)-3-[(2S)-2-(tert-butoxycarbonyl)amino-3-methyl-1-oxobutyl]-1,3-thiazolidin-4-ylcarboxamido]-1-hydroxy-3-phenylpropane (Compound No. 1-42)

(1RS,2S)-1-Hydroxy-2-[(4R)-3-[(2S)-3-methyl-1-oxo-2-[[(phenylmethoxy)carbonyl]amino]butyl]-1,3-thiazolidin-4-ylcarboxamido]-3-phenyl-1-(2-thiazolyl)propane (Compound No. 1-43)

(1RS,2S)-2-[(4R)-3-[(2S)-2-(tert-Butoxycarbonyl)amino-3-methyl-1-oxobutyl]-1,3-thiazolidin-4-ylcarboxamido]-1-hydroxy-3-phenyl-1-(2-thiazolyl)propane (Compound No. 1-44)

(1RS,2S)-1-(2-Benzothiazolyl)-1-hydroxy-2-[(4R)-3-[(2S)-3-methyl-1-oxo-2-[[(phenylmethoxy)carbonyl]amino]butyl]-1,3-thiazolidin-4-ylcarboxamido]-3-phenylpropane (Compound No. 1-45)
$[\alpha]_D^{20}$ −87.7° (c=0.5, methanol); IR(KBr,cm$^{-1}$): Rf (large) 3306,2962,1717,1658,1515,1423,1237,698, Rf (small) 3306,1656,1513,1422,1238,1027,759,698.

(1RS,2S)-1-(2-Benzothiazolyl)-2-[(4R)-3-[(2S)-2-(tert-butoxycarbonyl)amino-3-methyl-1-oxobutyl]-1,3-thiazolidin-4-ylcarboxamido]-1-hydroxy-3-phenylpropane (Compound No. 1-46)

Isopropyl (2RS,3S)-2-hydroxy-3-[(2RS,4R)-3-[(2S)-3-methyl-1-oxo-2-[[(phenylmethoxy)carbonyl]amino]butyl]-2-phenyl-1,3-thiazolidin-4-ylcarboxamido]-4-phenylbutyrate (Compound No. 1-47)
IR(Film,cm$^{-1}$): 3330,2965,2874,1694,1519.

Isopropyl (2RS,3S)-2-hydroxy-3-[(2RS,4R)-3-[1-oxo-2-[[(phenylmethoxy)carbonyl]amino]ethyl]-2-phenyl-1,3-thiazolidin-4-ylcarboxamido]-4-phenylbutyrate (Compound No. 1-48)

Isopropyl (2RS,3S)-2-hydroxy-3-[(2RS,4R)-3-[(2S)-1-oxo-2-[[(phenylmethoxy)carbonyl]amino]propyl]-2-phenyl-1,3-thiazolidin-4-ylcarboxamido]-4-phenylbutyrate (Compound No. 1-49)

Isopropyl (2RS,3S)-2-hydroxy-3-[(2RS,4R)-3-[(2S)-1-oxo-2-[[(phenylmethoxy)carbonyl]amino]butyl]-2-phenyl-1,3-thiazolidin-4-ylcarboxamido]-4-phenylbutyrate (Compound No. 1-50)

Isopropyl (2RS,3S)-2-hydroxy-3-[(2RS,4R)-3-[(2S)-4-methyl-1-oxo-2-[[(phenylmethoxy)carbonyl]amino]butyl]-2-phenyl-1,3-thiazolidin-4-ylcarboxamido]-4-phenylbutyrate (Compound No. 1-51)

Isopropyl (2RS,3S)-2-hydroxy-3-[(2RS,4R)-3-[(2S,3RS)-3-methyl-1-oxo-2-[[(phenylmethoxy)carbonyl]amino]pentyl]-2-phenyl-1,3-thiazolidin-4-ylcarboxamido]-4-phenylbutyrate (Compound No. 1-52)

Isopropyl (2RS,3S)-3-[(2RS,4R)-3-[(2S)-3,3-dimethyl-1-oxo-2-[[(phenylmethoxy)carbonyl]amino]butyl]-2-phenyl-1,3-thiazolidin-4-ylcarboxamido]-2-hydroxy-4-phenylbutyrate (Compound No. 1-53)

Isopropyl (2RS,3S)-2-hydroxy-3-[(2RS,4R)-3-[(2S)-1-oxo-2-phenyl-2-[[(phenylmethoxy)carbonyl]amino]ethyl]-2-phenyl-1,3-thiazolidin-4-ylcarboxamido]-4-phenylbutyrate (Compound No. 1-54)

Isopropyl (2RS,3S)-2-hydroxy-3-[(2RS,4R)-3-[(2S)-1-oxo-3-phenyl-2-[[(phenylmethoxy)carbonyl]amino]propyl]-2-phenyl-1,3-thiazolidin-4-ylcarboxamido]-4-phenylbutyrate (Compound No. 1-55)

Isopropyl (2RS,3S)-2-hydroxy-3-[(2RS,4R)-3-[(2RS)-1-oxo-6-phenyl-2-[[(phenylmethoxy)carbonyl]amino]hexyl]-2-phenyl-1,3-thiazolidin-4-ylcarboxamido]-4-phenylbutyrate (Compound No. 1-56)

Isopropyl (2RS,3S)-2-hydroxy-3-[(2RS,4R)-3-[(2S)-3-(4-hydroxyphenyl)-1-oxo-2-[[(phenylmethoxy)carbonyl]amino]propyl]-2-phenyl-1,3-thiazolidin-4-ylcarboxamido]-4-phenylbutyrate (Compound No. 1-57)

Isopropyl (2RS,3S)-2-hydroxy-3-[(2RS,4R)-3-[(2S)-1-oxo-2-[(phenylmethoxy)carbonyl]amino-3-[-1-(triphenylmethyl)imidazol-5-yl]propyl]-2-phenyl-1,3-thiazolidin-4-ylcarboxamido]-4-phenylbutyrate (Compound No. 1-58)

Isopropyl (2RS,3S)-2-hydroxy-3-[(2RS,4R)-3-[(2S)-1-oxo-2-[(phenylmethoxy)carbonyl]amino-3-[1-(triphenylmethyl)indol-3-yl]propyl]-2-phenyl-1,3-thiazolidin-4-ylcarboxamido]-4-phenylbutyrate (Compound No. 1-59)

Isopropyl (2RS,3S)-3-[(2RS,4R)-3-[(2S)-3-(tert-butoxy)-1-oxo-2-[[(phenylmethoxy)carbonyl]amino]propyl]-2-phenyl-1,3-thiazolidin-4-ylcarboxamido]-2-hydroxy-4-phenylbutyrate (Compound No. 1-60)

Isopropyl (2RS,3S)-3-[(2RS,4R)-3-[(2S)-3-(tert-butoxycarbonyl)-1-oxo-2-[[(phenylmethoxy)carbonyl]amino]propyl]-2-phenyl-1,3-thiazolidin-4-ylcarboxamido]-2-hydroxy-4-phenylbutyrate (Compound No. 1-61)

Isopropyl (2RS,3S)-2-hydroxy-3-[(2RS,4R)-3-[(2S)-3-methyl-2-(methylcarbonyl)amino-1-oxobutyl]-2-phenyl-1,3-thiazolidin-4-ylcarboxamido]-4-phenylbutyrate (Compound No. 1-62)

Isopropyl (2RS,3S)-2-hydroxy-3-[(2RS,4R)-3-[(2S)-3-methyl-1-oxo-2-[[(phenylmethoxy)carbonyl]amino]butyl]-2-phenyl-1,3-thiazolidin-4-ylcarboxamido]-4-phenylbutyrate (Compound No. 1-63)

Isopropyl (2RS,3S)-2-hydroxy-3-[(2RS,4R)-3-[(2S)-3-methyl-1-oxo-2-[[(phenylmethoxy)carbonyl]amino]butyl]-2-phenyl-1,3-thiazolidin-4-ylcarboxamido]-4-phenylbutyrate (Compound No. 1-64)

Isopropyl (2RS,3S)-2-hydroxy-3-[(2RS,4R)-3-[(2S)-2-[(methoxymethyl)carbonyl]amino-3-methyl-1-oxobutyl]-2-phenyl-1,3-thiazolidin-4-ylcarboxamido]-4-phenylbutyrate (Compound No. 1-65)

Isopropyl (2RS,3S)-2-hydroxy-3-[(2RS,4R)-3-[(2S)-3-methyl-1-oxo-2-[[(phenylmethoxy)carbonyl]amino]butyl]-2-phenyl-1,3-thiazolidin-4-ylcarboxamido]-4-phenylbutyrate (Compound No. 1-66)

Isopropyl (2RS,3S)-3-[(2RS,4R)-3-[(2S)-2-(tert-butoxycarbonyl)amino-3-methyl-1-oxobutyl]-2-phenyl-1,3-thiazolidin-4-ylcarboxamido]-2-hydroxy-4-phenylbutyrate (Compound No. 1-67)

Isopropyl (2RS,3S)-2-hydroxy-3-[(2RS,4R)-3-[(2S)-3-methyl-1-oxo-2-[(phenylmethoxy)carbonyl]amino]butyl]-2-phenyl-1,3-thiazolidin-4-ylcarboxamido]-4-phenylbutyrate (Compound No. 1-68)

Isopropyl (2RS,3S)-2-hydroxy-3-[(2RS,4R)-3-[(2S)-2-[[(4-methoxyphenyl)methoxy]carbonyl]amino-3-methy-1-oxobutyl]-2-phenyl-1,3-thiazolidin-4-ylcarboxamido]-4-phenylbutyrate (Compound No. 1-69)

Isopropyl (2RS,3S)-3-[(2RS,4R)-3-[(2S)-2-[(N-ethyl-N-methylamino)carbonyl]amino-3-methyl-1-oxobutyl]-2-phenyl-1,3-thiazolidin-4-ylcarboxamido]-2-hydroxy-4-phenylbutyrate (Compound No. 1-70)
IR(Film,cm$^{-1}$): 3350,2964,1727,1696,1632,1520,1244, 752.

Isopropyl (2RS,3S)-2-hydroxy-3-[(2RS,4R)-3-[(2S)-3-methyl-2-[[N-methyl-N-(phenylmethyl)amino]carbonyl]amino-1-oxobutyl]-2-2-phenyl-1,3-thiazolidin-4-ylcarboxamido]-4-phenylbutyrate (Compound No. 1-71)

Isopropyl (2RS,3S)-3-[(2RS,4R)-3-[(2S)-2-[[N-[2-[(tert-butoxycarbonyl)amino]ethyl]-N-methylamino]carbonyl]amino-3-methyl-1-oxobutyl]-2-phenyl-1,3-thiazolidin-4-ylcarboxamido]-2-hydroxy-4-phenylbutyrate (Compound No. 1-72)

Isopropyl (2RS,3S)-3-[(2RS,4R)-3-[(2S)-2-[[4-[N-(tert-butoxycarbonyl)-N-methylamino]piperidino]carbonyl]amino-3-methyl-1-oxobutyl]-2-phenyl-1,3-thiazolidin-4-ylcarboxamido]-2-hydroxy-4-phenylbutyrate (Compound No. 1-73)
IR(KBr,cm$^{-1}$): 3350,2978,1737,1658,1531.

Isopropyl (2RS,3S)-2-hydroxy-3-[(2RS,4R)-3-[(2S)-3-methyl-2-[(4-methylpiperazino)carbonyl]amino-1-oxobutyl]-2-phenyl-1,3-thiazolidin-4-ylcarboxamido]-4-phenylbutyrate (Compound No. 1-74)
IR(KBr,cm$^{-1}$): 3345,2972,2797,1736,1638,1521,1455, 1416,1263, 1105.

Isopropyl (2RS,3S)-2-hydroxy-3-[(2RS,4R)-3-[(2S)-2-[(methoxymethyl)carbonyl]amino-1-oxopropyl]-2-phenyl-1,3-thiazolidin-4-ylcarboxamido]-4-phenylbutyrate (Compound No. 1-75)

Isopropyl (2RS,3S)-2-hydroxy-3-[(2RS,4R)-3-[(2S)-2-[N-methyl-N-[(phenylmethoxy)carbonyl]amino]-1-oxopropyl]-2-phenyl-1,3-thiazolidin-4-ylcarboxamido]-4-phenylbutyrate (Compound No. 1-76)

Isopropyl (2RS,3S)-3-[(2RS,4R)-3-[(2S)-2-[N-ethyl-N-[(phenylmethoxy)carbonyl]amino]-1-oxopropyl]-2-phenyl-1,3-thiazolidin-4-ylcarboxamido]-2-hydroxy-4-phenylbutyrate (Compound No. 1-77)

Isopropyl (2RS)-2-hydroxy-3-[(2RS,4R)-3-[(2RS)-1-oxo-6-phenyl-2-[[(phenylmethoxy)carbonyl]amino]hexyl]-2-phenyl-1,3-thiazolidin-4-ylcarboxamido]propionate (Compound No. 1-78)

Isopropyl (2RS,3S)-2-hydroxy-4-phenyl-3-[(2RS,4R)-2-phenyl-3-[(2S)-1-[(phenylmethoxy)carbonyl]pyrrolidin-2-yl]carbonyl-1,3-thiazolidin-4-ylcarboxamido]butyrate (Compound No. 1-79)

Isopropyl (2RS,3S)-2-hydroxy-4-phenyl-3-[(2RS,4R)-2-phenyl-3-[(4R)-3-(phenylmethoxy)carbonyl-1,3-thiazolidin-4-yl]carbonyl-1,3-thiazolidin-4-ylcarboxamido]butyrate (Compound No. 1-80)

(2RS,3RS)-2-Hydroxy-3-[(2RS,4R)-3-[(2S)-3-methyl-1-oxo-2-[[(phenylmethoxy)carbonyl]amino]butyl]-2-phenyl-1,3-thiazolidin-4-ylcarboxamido]-4-phenyl-1,1,1-trifluorobutane (Compound No. 1-81)
IR(Film,cm$^{-1}$); Rf (large) 3326,1667,1532,1273,1170, 1139,756,699, Rf (small) 3322,1663,1530,1272,1170,1137, 754,699.

(2RS,3RS)-3-[(2RS,4R)-3-[(2S)-2-(tert-Butoxycarbonyl)amino-3-methyl-1-oxobutyl]-2-phenyl-1,3-thiazolidin-4-ylcarboxamido]-2-hydroxy-4-phenyl-1,1,1-trifluorobutane (Compound No. 1-82)

Phenylmethyl (2RS,3S)-2-hydroxy-3-[(2RS,4R)-3-[(2S)-3-methyl-1-oxo-2-[[(phenylmethoxy)carbonyl]amino]butyl]-2-phenyl-1,3-thiazolidin-4-ylcarboxamido]-4-phenylbutyrate (Compound No. 1-83)

Phenylmethyl (2RS,3S)-3-[(2RS,4R)-3-[(2S)-2-(tert-butoxycarbonyl)amino-3-methyl-1-oxobutyl]-2-phenyl-1,3-thiazolidin-4-ylcarboxamido]-2-hydroxy-4-phenylbutyrate (Compound No. 1-84)

(1RS,2S)-1-Hydroxy-2-[(2RS,4R)-3-[(2S)-3-methyl-1-oxo-2-[[(phenylmethoxy)carbonyl]amino]butyl]-2-phenyl-1,3-thiazolidin-4-ylcarboxamido]-1-(2-oxazolyl)-3-phenylpropane (Compound No. 1-85)

(1RS,2S)-2-[(2RS,4R)-3-[(2S)-2-(tert-Butoxycarbonyl)amino-3-methyl-1-oxobutyl]-2-phenyl-1,3-thiazolidin-4-ylcarboxamido]-1-hydroxy-1-(2-oxazolyl)-3-phenylpropane (Compound No. 1-86)

(1RS,2S)-1-(2-Benzoxazolyl)-1-hydroxy-2-[(2RS,4R)-3-[(2S)-3-methyl- 1-oxo-2-[[(phenylmethoxy)carbonyl]amino]butyl]-2-phenyl-1,3-thiazolidin-4-ylcarboxamido]-3-phenylpropane (Compound No. 1-87)

(1RS,2S)-1-(2-Benzoxazolyl)-2-[(2RS,4R)-3-[(2S)-2-(tert-butoxycarbonyl)amino-3-methyl-1-oxobutyl]-2-phenyl-1,3-thiazolidin-4-ylcarboxamido]-1-hydroxy-3-phenylpropane (Compound No. 1-88)

(1RS,2S)-1-Hydroxy-2-[(2RS,4R)-3-[(2S)-3-methyl-1-oxo-2-[[(phenylmethoxy)carbonyl]amino]butyl]-2-phenyl-1,3-thiazolidin-4-ylcarboxamido]-3-phenyl-1-(2-thiazolyl)propane (Compound No. 1-89)

(1RS,2S)-2-[(2RS,4R)-3-[(2S)-2-(tert-Butoxycarbonyl)amino-3-methyl-1-oxobutyl]-2-phenyl-1,3-thiazolidin-4-ylcarboxamido]-1-hydroxy-3-phenyl-1-(2-thiazolyl)propane (Compound No. 1-90)

(1RS,2S)-1-(2-Benzothiazolyl)-1-hydroxy-2-[(2RS,4R)-3-[(2S)-3-methyl-1-oxo-2-[[(phenylmethoxy)carbonyl]amino]butyl]-2-phenyl-1,3-thiazolidin-4-ylcarboxamido]-3-phenylpropane (Compound No. 1-91)

(1RS,2S)-1-(2-Benzothiazolyl)-2-[(2RS,4R)-3-[(2S)-2-(tert-butoxycarbonyl)amino-3-methyl-1-oxobutyl]-2-phenyl-1,3-thiazolidin-4-ylcarboxamido]-1-hydroxy-3-phenylpropane (Compound No. 1-92)

Isopropyl (2RS,3S)-3-[(3S,6RS,9R)-1-aza-2-oxo-3-[(phenylmethoxy)carbonyl]amino-7-thiabicyclo[4.3.0]nonan-9-yl-carboxamido]-2-hydroxy-4-phenylbutyrate (Compound No. 1-93)
IR(KBr,cm$^{-1}$): Rf (large) 3339,3062,3030,2939,1732, 1668,1532,1426,1374, 1261,1104,1016, Rf (small) 3334, 3062,3031,2980,2938,1735,1673,1532,1497, 1455,1427, 1387,1375.

Isopropyl (2RS,3S)-3-[(3R,6RS,9R)-1-aza-2-oxo-3-[(phenylmethoxy)carbonyl]amino-7-thiabicyclo[4.3.0]nonan-9-yl-carboxamido]-2-hydroxy-4-phenylbutyrate (Compound No. 1-94)
IR(Film,cm$^{-1}$): 3400,2980,1722,1530,1496,1434,1374, 1314,1254, 1104,1028.

Isopropyl (2RS,3S)-3-[(3S,5RS,8R)-1-aza-2-oxo-3-[(phenylmethoxy)carbonyl]amino-6-thiabicyclo[3.3.0]octan-8-ylcarboxamido]-2-hydroxy-4-phenylbutyrate (Compound No. 1-95)

Isopropyl (2RS,3S)-3-[(3S,7RS,10R)-1-aza-2-oxo-3-[(phenylmethoxy)carbonyl]amino-8-thiabicyclo[5.3.0]decan-10-yl-carboxamido]-2-hydroxy-4-phenylbutyrate (Compound No. 1-96)
IR(Film,cm$^{-1}$): 3413,3344,3029,2979,1714,1518,1450, 1407,1343, 1229,1108.

Isopropyl (2RS,3S)-3-[(3R,7RS,10R)-1-aza-2-oxo-3-[(phenylmethoxy)carbonyl]amino-8-thiabicyclo[5.3.0]decan-10-ylcarboxamido]-2-hydroxy-4-phenylbutyrate (Compound No. 1-97)
IR(Film,cm$^{-1}$): 3330,3062,3028,2927,1716,1518,1453, 1406,1343, 1265,1229,1106.

Isopropyl (2RS,3S)-3-[(3S,8RS,11R)-1-aza-2-oxo-3-[(phenylmethoxy)carbonyl]amino-9-thiabicyclo[6.3.0]undecan-11-ylcarboxamido]-2-hydroxy-4-phenylbutyrate (Compound No. 1-98)

Phenylmethyl (2RS,3S)-3-[(3S,6RS,9R)-1-aza-2-oxo-3-[(phenylmethoxy)carbonyl]amino-7-thiabicyclo[4.3.0]nonan-9-ylcarboxamido]-2-hydroxy-4-phenylbutyrate (Compound No. 1-99)

Phenylmethyl (2RS,3S)-3-[(3S,7RS,10R)-1-aza-2-oxo-3-[(phenylmethoxy)carbonyl]amino-8-thiabicyclo[5.3.0]-10-ylcarboxamido]-2-hydroxy-4-phenylbutyrate (Compound No. 1-100)

Example 2

Isopropyl (3S)-3-[(4R)-3-[(2S)-3-methyl-1-oxo-2-[[(phenylmethoxy)carbonyl]amino]butyl]-1,3-thiazolidin-4-ylcarboxamido]-2-oxo-4-phenylbutyrate (Compound No. 2-1)

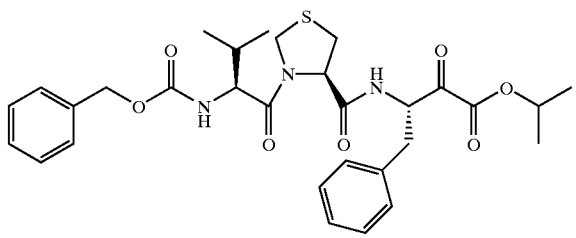

Acetic anhydride (5.0 ml) is added to a solution of isopropyl (2RS,3S)-2-hydroxy-3-[(4R)-3-[(2S)-3-methyl-1-oxo-2-[[(phenylmethoxy)carbonyl]amino]butyl]-1,3-thiazolidin-4-ylcarboxamido]-4-phenylbutyrate (0.49 g) in dimethyl sulfoxide (5.0 ml), and the mixture is stirred overnight. Water (45 ml) is added to the reaction mixture, the whole is stirred for one hour, and sodium hydrogencarbonate is added to the reaction mixture to basify it. The reaction mixture is extracted with ethyl acetate, and the extract is washed with a saturated aqueous sodium hydrogencarbonate solution, water and saturated brine successively. The extract is dried over anhydrous magnesium sulfate and concentrated under reduced pressure. The residue is purified by silica gel column chromatography to give 0.28 g of the titled compound.

$[\alpha]_D^{20}$ −91.0° (c=0.5, methanol); IR(Film,cm$^{-1}$): 3308, 1722,1644,1520,1424,1259,1102,753.

The following compounds are obtained by a method similar to Example 2.

Isopropyl (3S)-2-oxo-3-[(4R)-3-[1-oxo-2-[[(phenylmethoxy)carbonyl]amino]ethyl]-1,3-thiazolidin-4-ylcarboxamido]-4-phenylbutyrate (Compound No. 2-2)
IR(Film,cm$^{-1}$): 3322,1723,1667,1526,1453,1254,753, 699.

Isopropyl (3S)-2-oxo-3-[(4R)-3-[(2S)-1-oxo-2-[[(phenylmethoxy)carbonyl]amino]propyl]-1,3-thiazolidin-4-ylcarboxamido]-4-phenylbutyrate (Compound No. 2-3)
$[\alpha]_D^{20}$ −98.0° (c=0.5, methanol); IR(Film,cm$^{-1}$): 3316, 1723,1658,1526,1455,1257,1068,753.

Isopropyl (3S)-2-oxo-3-[(4R)-3-[(2S)-1-oxo-2-[[(phenylmethoxy)carbonyl]amino]butyl]-1,3-thiazolidin-4-ylcarboxamido]-4-phenylbutyrate (Compound No. 2-4)

Isopropyl (3S)-3-[(4R)-3-[(2S)-4-methyl-1-oxo-2-[[(phenylmethoxy)carbonyl]amino]pentyl]-1,3-thiazolidin-4-ylcarboxamido]-2-oxo-4-phenylbutyrate (Compound No. 2-5)
IR(Film,cm$^{-1}$): 3315,2958,1723,1651,1527,1258,1104, 1051,754, Isopropyl (3S)-3-[(4R)-3-[(2S,3RS)-3-methyl-1-oxo-2-[[(phenylmethoxy)carbonyl]amino]pentyl]-1,3-thiazolidin-4-ylcarboxamido]-2-oxo-4-phenylbutyrate (Compound No. 2-6)
IR(Film,cm$^{-1}$): 3309,2968,1724,1642,1519,1251,1104, 1045,754, Isopropyl (3S)-3-[(4R)-3-[(2S)-3,3-dimethyl-1-oxo-2-[[(phenylmethoxy)carbonyl]amino]butyl]-1,3-thiazolidin-4-ylcarboxamido]-2-oxo-4-phenylbutyrate (Compound No. 2-7)

Isopropyl (3S)-2-oxo-3-[(4R)-3-[(2S)-1-oxo-2-phenyl-2-[[(phenylmethoxy)carbonyl]amino]ethyl]-1,3-thiazolidin-4-ylcarboxamido]-4-phenylbutyrate (Compound No. 2-8)
$[\alpha]_D^{20}$ −83.7° (c=0.5, methanol); IR(KBr,cm$^{-1}$): 3319, 1726,1660,1497,1455,1265,1053,699.

Isopropyl (3S)-2-oxo-3-[(4R)-3-[(2S)-1-oxo-3-phenyl-2-[[(phenylmethoxy)carbonyl]amino]propyl]-1,3-thiazolidin-4-ylcarboxamido]-4-phenylbutyrate (Compound No. 2-9)
IR(Film,cm$^{-1}$): 3305,3062,3028,2980,1723,1661,1603, 1584,1529, 1454,1420,1259.

Isopropyl (3S)-2-oxo-3-[(4R)-3-[(2RS)-1-oxo-6-phenyl-2-[[(phenylmethoxy)carbonyl]amino]hexyl]-1,3-thiazolidin-4-ylcarboxamido]-4-phenylbutyrate (Compound No. 2-10)

Isopropyl (3S)-3-[(4R)-3-[(2S)-3-(4-hydroxyphenyl)-1-oxo-2-[[(phenylmethoxy)carbonyl]amino]propyl]- 1,3-thiazolidin-4-ylcarboxamido]-2-oxo-4-phenylbutyrate (Compound No. 2-11)
IR(Film,cm$^{-1}$): 3306,2981,2919,1721,1650,1510,1423, 1375,1251, 1102,1051.

Isopropyl (3S)-2-oxo-3-[(4R)-3-[(2S)-1-oxo-2-[(phenylmethoxy)carbonyl]amino]-3-[1-(triphenylmethyl)imidazol-5-yl]propyl]-1,3-thiazolidin-4-ylcarboxamido]-4-phenylbutyrate (Compound No. 2-12)
IR(KBr,cm$^{-1}$): 3291,2980,2288,1721,1662,1494,1445, 1374,1248, 1100,1038,1001.

Isopropyl (3S)-2-oxo-3-[(4R)-3-[(2S)-1-oxo-2-[(phenylmethoxy)carbonyl]amino]-3-[1-(triphenylmethyl)indol-3-yl]propyl]-1,3-thiazolidin-4-ylcarboxamido]-4-phenylbutyrate (Compound No. 2-13)

Isopropyl (3S)-3-[(4R)-3-[(2S)-3-(tert-butoxy)-1-oxo-2-[[(phenylmethoxy)carbonyl]amino]propyl]-1,3-thiazolidin-4-ylcarboxamido]-2-oxo-4-phenylbutyrate (Compound No. 2-14)
IR(Film,cm$^{-1}$): 3306,2977,1724,1661,1531,1258,1192, 110, 3,1051,754,699.

Isopropyl (3S)-3-[(4R)-3-[(2S)-3-(tert-butoxycarbonyl)-1-oxo-2-[[(phenylmethoxy)carbonyl]amino]propyl]-1,3-thiazolidin-4-ylcarboxamido]-2-oxo-4-phenylbutyrate (Compound No. 2-15)

Isopropyl (3S)-3-[(4R)-3-[(2S)-3-methyl-2-(methylcarbonyl)amino-1-oxobutyl]-1,3-thiazolidin-4-ylcarboxamido]-2-oxo-4-phenylbutyrate (Compound No. 2-16)
IR(Film,cm$^{-1}$): 3304,1728,1651,1537,1422,1260,1104, 754.

Isopropyl (3S)-3-[(4R)-3-[(2S)-3-methyl-1-oxo-2-[[(phenylmethoxy)carbonyl]amino]butyl]-1,3-thiazolidin-4-ylcarboxamido]-2-oxo-4-phenylbutyrate (Compound No. 2-17)

Isopropyl (3S)-3-[(4R)-3-[(2S)-3-methyl-1-oxo-2-[[(2-phenylethyl)carbonyl]amino]butyl]-1,3-thiazolidin-4-ylcarboxamido]-2-oxo-4-phenylbutyrate (Compound No. 2-18)

Isopropyl (3S)-3-[(4R)-3-[(2S)-2-[(methoxymethyl)carbonyl]amino-3-methyl-1-oxobutyl]-1,3-thiazolidin-4-ylcarboxamido]-2-oxo-4-phenylbutyrate (Compound No. 2-19)

IR(Film,cm$^{-1}$): 3306,2969,1729,1644,1527,1429,1258, 1107,753, 701.

Isopropyl (3S)-3-[(4R)-3-[(2S)-3-methyl-1-oxo-2-[[(phenoxymethyl)carbonyl]amino]butyl]-1,3-thiazolidin-4-ylcarboxamido]-2-oxo-4-phenylbutyrate (Compound No. 2-20)

IR(Film,cm$^{-1}$): 3305,3067,2967,2934,1726,1653,1599, 1522,1498, 1429,1388,1374,1242,1174.

Isopropyl (3S)-3-[(4R)-3-[(2S)-2-(tert-butoxycarbonyl)amino-3-methyl-1-oxobutyl]-1,3-thiazolidin-4-ylcarboxamido]-2-oxo-4-phenylbutyrate (Compound No. 2-21)

$[\alpha]_D^{20}$ −105.9° (c=0.5, methanol); IR(KBr,cm$^{-1}$): 3326, 1701,1519,1427,1256,1165,1103,1368.

Isopropyl (3S)-3-[(4R)-3-[(2S)-3-methyl-1-oxo-2-[(phenoxycarbonyl)amino]butyl]-1,3-thiazolidin-4-ylcarboxamido]-2-oxo-4-phenylbutyrate (Compound No. 2-22)

Isopropyl (3S)-3-[(4R)-3-[(2S)-2-[[(4-methoxyphenyl)methoxy]carbonyl]amino-3-methyl-1-oxobutyl]-1,3-thiazolidin-4-ylcarboxamido]-2-oxo-4-phenylbutyrate (Compound No. 2-23)

IR(Film,cm$^{-1}$): 3307,2965,2359,2340,1723,1613,1586, 1515,1453, 1424,1247.

Isopropyl (3S)-3-[(4R)-3-[(2S)-2-[(N-ethyl-N-methylamino)carbonyl]amino-3-methyl-1-oxobutyl]-1,3-thiazolidin-4-ylcarboxamido]-2-oxo-4-phenylbutyrate (Compound No. 2-24)

Isopropyl (3S)-3-[(4R)-3-[(2S)-3-methyl-2-[[N-methyl-N-(phenylmethyl)amino]carbonyl]amino-1-oxobutyl]-1,3-thiazolidin-4-ylcarboxamido]-2-oxo-4-phenylbutyrate (Compound No. 2-25)

IR(Film,cm$^{-1}$): 3321,2977,1727,1634,1520,1423,1258, 754,700.

Isopropyl (3S)-3-[(4R)-3-[(2S)-2-[[N-[2-[(tert-butoxycarbonyl)amino]ethyl]-N-methylamino]carbonyl]amino-3-methyl-1-oxobutyl]-1,3-thiazolidin-4-ylcarboxamido]-2-oxo-4-phenylbutyrate (Compound No. 2-26)

IR(KBr,cm$^{-1}$): 3338,2978,1725,1691,1634,1523,1427, 1366,1250, 1171,1102.

Isopropyl (3S)-3-[(4R)-3-[(2S)-2-[[4-[N-(tert-butoxycarbonyl)-N-methylamino]piperidino]carbonyl]amino-3-methyl-1-oxobutyl]-1,3-thiazolidin-4-ylcarboxamido]-2-oxo-4-phenylbutyrate (Compound No. 2-27)

Isopropyl (3S)-3-[(4R)-3-[(2S)-3-methyl-2-[(4-methylpiperazino)carbonyl]amino-1-oxobutyl]-1,3-thiazolidin-4-ylcarboxamido]-2-oxo-4-phenylbutyrate hydrochloride (Compound No. 2-28)

Isopropyl (3S)-3-[(4R)-3-[(2S)-2-[(methoxymethyl)carbonyl]amino-1-oxopropyl]-1,3-thiazolidin-4-ylcarboxamido]-2-oxo-4-phenylbutyrate (Compound No. 2-29)

$[\alpha]_D^{20}$ −81.3° (c=0.6, methanol); IR(Film,cm$^{-1}$): 3305, 1726,1650,1525,1454,1426,1115,752.

Isopropyl (3S)-3-[(4R)-3-[(2S)-2-[N-methyl-N-[(phenylmethoxy)carbonyl]amino]-1-oxopropyl]-1,3-thiazolidin-4-ylcarboxamido]-2-oxo-4-phenylbutyrate (Compound No. 2-30)

Isopropyl (3S)-3-[(4R)-3-[(2S)-2-[N-ethyl-N-[(phenylmethoxy)carbonyl]amino]-1-oxopropyl]-1,3-thiazolidin-4-ylcarboxamido]-2-oxo-4-phenylbutyrate (Compound No. 2-31)

Isopropyl 2-oxo-3-[(4R)-3-[(2RS)-1-oxo-6-phenyl-2-[[(phenylmethoxy)carbonyl]amino]hexyl]-1,3-thiazolidin-4-ylcarboxamido]propionate (Compound No. 2-32)

IR(Film,cm$^{-1}$): 3306,3025,2933,1825,1713,1669,1517, 1455,1423, 1374,1338,1218,1100.

Isopropyl (3S)-2-oxo-4-phenyl-3-[(4R)-3-[(2S)-1-[(phenylmethoxy)carbonyl]pyrrolidin-2-yl]carbonyl]-1,3-thiazolidin-4-ylcarboxamido]butyrate (Compound No. 2-33)

IR(Film,cm$^{-1}$): 3307,3063,3030,2981,2881,1706,1526, 1498,1415, 1356.

Isopropyl (3S)-2-oxo-4-phenyl-3-[(4R)-3-[(4R)-3-(phenylmethoxy)carbonyl-1,3-thiazolidin-4-yl]carbonyl-1,3-thiazolidin-4-ylcarboxamido]butyrate (Compound No. 2-34)

(3RS)-3-[(4R)-3-[(2S)-3-Methyl-1-oxo-2-[[(phenylmethoxy)carbonyl]amino]butyl]- 1,3-thiazolidin-4-ylcarboxamido]-2-oxo-4-phenyl-1,1,1-trifluorobutane (Compound No. 2-35)

(3RS)-3-[(4R)-3-[(2S)-2-(tert-Butoxycarbonyl)amino-3-methyl-1-oxobutyl]-1,3-thiazolidin-4-ylcarboxamido]-2-oxo-4-phenyl-1,1,1-trifluorobutane (Compound No. 2-36)

Phenylmethyl (3S)-3-[(4R)-3-[(2S)-3-methyl-1-oxo-2-[[(phenylmethoxy)carbonyl]amino]butyl]-1,3-thiazolidin-4-ylcarboxamido]-2-oxo-4-phenylbutyrate (Compound No. 2-37)

Phenylmethyl (3S)-3-[(4R)-3-[(2S)-2-(tert-butoxycarbonyl)amino-3-methyl-1-oxobutyl]-1,3-thiazolidin-4-ylcarboxamido]-2-oxo-4-phenylbutyrate (Compound No. 2-38)

(2S)-2-[(4R)-3-[(2S)-3-Methyl-1-oxo-2-[[(phenylmethoxy)carbonyl]amino]butyl]-1,3-thiazolidin-4-ylcarboxamido]-1-(2-oxazolyl)-1-oxo-3-phenylpropane (Compound No. 2-39)

(2S)-2-[(4R)-3-[(2S)-2-(tert-Butoxycarbonyl)amino-3-methyl-1-oxobutyl]-1,3-thiazolidin-4-ylcarboxamido]-1-(2-oxazolyl)-1-oxo-3-phenylpropane (Compound No. 2-40)

(2S)-1-(2-Benzoxazolyl)-2-[(4R)-3-[(2S)-3-methyl-1-oxo-2-[[(phenylmethoxy)carbonyl]amino]butyl]-1,3-thiazolidin-4-ylcarboxamido]-1-oxo-3-phenylpropane (Compound No. 2-41)

(2S)-1-(2-Benzoxazolyl)-2-[(4R)-3-[(2S)-2-(tert-butoxycarbonyl)amino-3-methyl-1-oxobutyl]-1,3-thiazolidin-4-ylcarboxamido]-1-oxo-3-phenylpropane (Compound No. 2-42)

(2S)-2-[(4R)-3-[(2S)-3-Methyl-1-oxo-2-[[(phenylmethoxy)carbonyl]amino]butyl]-1,3-thiazolidin-4-ylcarboxamido]-1-oxo-3-phenyl-1-(2-thiazolyl)propane (Compound No. 2-43)

(2S)-2-[(4R)-3-[(2S)-2-(tert-Butoxycarbonyl)amino-3-methyl-1-oxobutyl]-1,3-thiazolidin-4-ylcarboxamido]-1-oxo-3-phenyl-1-(2-thiazolyl)propane (Compound No. 2-44)

(2S)-1-(2-Benzothiazolyl)-2-[(4R)-3-[(2S)-3-methyl-1-oxo-2-[[(phenylmethoxy)carbonyl]amino]butyl]-1,3-thiazolidin-4-ylcarboxamido]-1-oxo-3-phenylpropane (Compound No. 2-45)

(2S)-1-(2-Benzothiazolyl)-2-[(4R)-3-[(2S)-2-(tert-butoxycarbonyl)amino-3-methyl-1-oxobutyl]-1,3-thiazolidin-4-ylcarboxamido]-1-oxo-3-phenylpropane (Compound No. 2-46)

Isopropyl (3S)-2-oxo-3-[(2RS,4R)-3-[(2S)-3-methyl-1-oxo-2-[[(phenylmethoxy)carbonyl]amino]butyl]-1,3-thiazolidin-4-ylcarboxamido]-4-phenylbutyrate (Compound No. 2-47)

IR(KBr,cm⁻¹): 3315,3275,2959,1720,1691,1655,1539.

Isopropyl (3S)-2-oxo-3-[(2RS,4R)-3-[1-oxo-2-[[(phenylmethoxy)carbonyl]amino]ethyl]-2-phenyl-1,3-thiazolidin-4-ylcarboxamido]-4-phenylbutyrate (Compound No. 2-48)

Isopropyl (3S)-2-oxo-3-[(2RS,4R)-3-[(2S)-1-oxo-2-[[(phenylmethoxy)carbonyl]amino]propyl]-2-phenyl-1,3-thiazolidin-4-ylcarboxamido]-4-phenylbutyrate (Compound No. 2-49)

Isopropyl (3S)-2-oxo-3-[(2RS,4R)-3-[(2S)-1-oxo-2-[[(phenylmethoxy)carbonyl]amino]butyl]-2-phenyl-1,3-thiazolidin-4-ylcarboxamido]-4-phenylbutyrate (Compound No. 2-50)

Isopropyl (3S)-3-[(2RS,4R)-3-[(2S)-4-methyl-1-oxo-2-[[(phenylmethoxy)carbonyl]amino]pentyl]-2-phenyl-1,3-thiazolidin-4-ylcarboxamido]-2-oxo-4-phenylbutyrate (Compound No. 2-51)
IR(Film,cm⁻¹): 3308,3063,2959,1722,1518,752.

Isopropyl (3S)-3-[(2RS,4R)-3-[(2S,3RS)-3-methyl-1-oxo-2-[[(phenylmethoxy)carbonyl]amino]pentyl]-2-phenyl-1,3-thiazolidin-4-ylcarboxamido]-2-oxo-4-phenylbutyrate (Compound No. 2-52)
IR(KBr,cm⁻¹): 3310,2964,2876,1747,1719,1691,1652,1535.

Isopropyl (3S)-3-[(2RS,4R)-3-[(2S)-3,3-dimethyl-1-oxo-2-[[(phenylmethoxy)carbonyl]amino]butyl]-2-phenyl-1,3-thiazolidin-4-ylcarboxamido]-2-oxo-4-phenylbutyrate (Compound No. 2-53)

Isopropyl (3S)-2-oxo-3-[(2RS,4R)-3-[(2S)-1-oxo-2-phenyl-2-[[(phenylmethoxy)carbonyl]amino]ethyl]-2-phenyl-1,3-thiazolidin-4-ylcarboxamido]-4-phenylbutyrate (Compound No. 2-54)

Isopropyl (3S)-2-oxo-3-[(2RS,4R)-3-[(2S)-1-oxo-3-phenyl-2-[[(phenylmethoxy)carbonyl]amino]propyl]-2-phenyl-1,3-thiazolidin-4-ylcarboxamido]-4-phenylbutyrate (Compound No. 2-55)

Isopropyl (3S)-2-oxo-3-[(2RS,4R)-3-[(2RS)-1-oxo-6-phenyl-2-[[(phenylmethoxy)carbonyl]amino]hexyl]-2-phenyl-1,3-thiazolidin-4-ylcarboxamido]-4-phenylbutyrate (Compound No. 2-56)

Isopropyl (3S)-3-[(2RS,4R)-3-[(2S)-3-(4-hydroxyphenyl)-1-oxo-2-[[(phenylmethoxy)carbonyl]amino]propyl]-2-phenyl-1,3-thiazolidin-4-ylcarboxamido]-2-oxo-4-phenylbutyrate (Compound No. 2-57)

Isopropyl (3S)-2-oxo-3-[(2RS,4R)-3-[(2S)-1-oxo-2-[(phenylmethoxy)carbonyl]amino-3-[1-(triphenylmethyl)imidazol-5-yl]propyl]-2-phenyl-1,3-thiazolidin-4-ylcarboxamido]-4-phenylbutyrate (Compound No. 2-58)
$[\alpha]_D^{20}$ −91.0° (c=0.5, methanol);

Isopropyl (3S)-2-oxo-3-[(2RS,4R)-3-[(2S)-1-oxo-2-[(phenylmethoxy)carbonyl]amino-3-[1-(triphenylmethyl)indol-3-yl]propyl]-2-phenyl-1,3-thiazolidin-4-ylcarboxamido]-4-phenylbutyrate (Compound No. 2-59)

Isopropyl (3S)-3-[(2RS,4R)-3-[(2S)-3-(tert-butoxy)-1-oxo-2-[[(phenylmethoxy)carbonyl]amino]propyl]-2-phenyl-1,3-thiazolidin-4-ylcarboxamido]-2-oxo-4-phenylbutyrate (Compound No. 2-60)

Isopropyl (3S)-3-[(2RS,4R)-3-[(2S)-3-[(tert-butoxycarbonyl)-1-oxo-2-[[(phenylmethoxy)carbonyl]amino]propyl]-2-phenyl-1,3-thiazolidin-4-ylcarboxamido]-2-oxo-4-phenylbutyrate (Compound No. 2-61)

Isopropyl (3S)-3-[(2RS,4R)-3-[(2S)-3-methyl-2-(methylcarbonyl)amino-1-oxobutyl]-2-phenyl-1,3-thiazolidin-4-ylcarboxamido]-2-oxo-4-phenylbutyrate (Compound No. 2-62)

Isopropyl (3S)-3-[(2RS,4R)-3-[(2S)-3-methyl-1-oxo-2-[[(phenylmethoxy)carbonyl]amino]butyl]-2-phenyl-1,3-thiazolidin-4-ylcarboxamido]-2-oxo-4-phenylbutyrate (Compound No. 2-63)

Isopropyl (3S)-3-[(2RS,4R)-3-[(2S)-3-methyl-1-oxo-2-[[(2-phenylethyl)carbonyl]amino]butyl]-2-phenyl-1,3-thiazolidin-4-ylcarboxamido]-2-oxo-4-phenylbutyrate (Compound No. 2-64)

Isopropyl (3S)-3-[(2RS,4R)-3-[(2S)-2-[(methoxymethyl)carbonyl]amino-3-methyl-1-oxobutyl]-2-phenyl-1,3-thiazolidin-4-ylcarboxamido]-2-oxo-4-phenylbutyrate (Compound No. 2-65)

Isopropyl (3S)-3-[(2RS,4R)-3-[(2S)-3-methyl-1-oxo-2-[[(phenoxylmethyl)carbonyl]amino]butyl]-2-phenyl-1,3-thiazolidin-4-ylcarboxamido]-2-oxo-4-phenylbutyrate (Compound No. 2-66)

Isopropyl (3S)-3-[(2RS,4R)-3-[(2S)-2-(tert-butoxycarbonyl)amino-3-methyl-1-oxobutyl]-2-phenyl-1,3-thiazolidin-4-ylcarboxamido]-2-oxo-4-phenylbutyrate (Compound No. 2-67)

Isopropyl (3S)-3-[(2RS,4R)-3-[(2S)-3-methyl-1-oxo-2-[(phenylmethyl)carbonyl]amino]butyl]-2-phenyl-1,3-thiazolidin-4-ylcarboxamido]-2-oxo-4-phenylbutyrate (Compound No. 2-68)

Isopropyl (3S)-3-[(2RS,4R)-3-[(2S)-2-[[(4-methoxyphenyl)methoxy]carbonyl]amino-3-methyl-1-oxobutyl]-2-phenyl-1,3-thiazolidin-4-ylcarboxamido]-2-oxo-4-phenylbutyrate (Compound No. 2-69)

Isopropyl (3S)-3-[(2RS,4R)-3-[(2S)-2-[(N-ethyl-N-methylamino)carbonyl]amino-3-methyl-1-oxobutyl]-2-phenyl-1,3-thiazolidin-4-ylcarboxamido]-2-oxo-4-phenylbutyrate (Compound No. 2-70)

Isopropyl (3S)-3-[(2RS,4R)-3-[(2S)-3-methyl-2-[[(N-methyl-N-(phenylmethyl)amino)carbonyl]amino]-1-oxybutyl]2-phenyl-1,3-thiazolidin-4-ylcarboxamido]-2-oxo-4-phenylbutyrate (Compound No. 2-71)

Isopropyl (3S)-3-[(2RS,4R)-3-[(2S)-2-[[N-[2-[(tert-butoxycarbonyl)amino]ethyl]-N-methylamino]carbonyl]amino-3-methyl-1-oxobutyl]-2-phenyl-1,3-thiazolidin-4-ylcarboxamido]-2-oxo-4-phenylbutyrate (Compound No. 2-72) IR(KBr,cm⁻¹): 3338,2979,1638,1519,1691,1725, 1249,1169,700.

Isopropyl (3S)-3-[(2RS,4R)-3-[(2S)-2-[[4-[N-(tert-butoxycarbonyl)-N-methylamino]piperidino]carbonyl]amino-3-methyl-1-oxobutyl]-2-phenyl-1,3-thiazolidin-4-ylcarboxamido]-2-oxo-4-phenylbutyrate (Compound No. 2-73)
IR(KBr,cm⁻¹): 3326,3062,3029,2977,1728,1691,1638, 1529,1455, 1407,1320,1149,750,723,699.

Isopropyl (3S)-3-[(2RS,4R)-3-[(2S)-3-methyl-2-[(4-methylpiperazino)carbonyl]amino-1-oxobutyl]-2-phenyl-1,3-thiazolidin-4-ylcarboxamido]-2-oxo-4-phenylbutyrate hydrochloride (Compound No. 2-74)
mp.104.0–110.0° C. IR(KBr,cm⁻³): 3271,2970, 1751, 1722,1644,1527, 1374,1265,1206, 721.

Isopropyl (3S)-3-[(2RS,4R)-3-[(2S)-2-[(methoxymethyl)carbonyl]amino-1-oxopropyl]-2-phenyl-1,3-thiazolidin-4-ylcarboxamido]-2-oxo-4-phenylbutyrate (Compound No. 2-75)

Isopropyl (3S)-3-[(2RS,4R)-3-[(2S)-2-[N-methyl-N-[(phenylmethoxy)carbonyl]amino]-1-oxopropyl]-2-phenyl-1,3-thiazolidin-4-ylcarboxamido]-2-oxo-4-phenylbutyrate (Compound No. 2-76)

Isopropyl (3S)-3-[(2RS,4R)-3-[(2S)-2-[N-ethyl-N-[(phenylmethoxy)carbonyl]amino]-1-oxopropyl]-2-phenyl-1,3-thiazolidin-4-ylcarboxamido]-2-oxo-4-phenylbutyrate (Compound No. 2-77)

Isopropyl 2-oxo-3-[(2RS,4R)-3-[(2RS)-1-oxo-6-phenyl-2-[[(phenylmethoxy)carbonyl]amino]hexyl]-2-phenyl-1,3-thiazolidin-4-ylcarboxamido]propionate (Compound No. 2-78)

Isopropyl (3S)-2-oxo-4-phenyl-3-[(2RS,4R)-2-phenyl-3-[(2S)-1-[(phenylmethoxy)carbonyl]pyrrolidin-2-yl]carbonyl-1,3-thiazolidin-4-ylcarboxamido]butyrate (Compound No. 2-79)

Isopropyl (3S)-2-oxo-4-phenyl-3-[(2RS,4R)-2-phenyl-3-[(4R)-3(phenylmethoxy)carbonyl-1,3-thiazolidin-4-yl]carbonyl-1,3-thiazolidin-4-ylcarboxamido]butyrate (Compound No. 2-80)

(3RS)-3-[(2RS,4R)-3-[(2S)-3-Methyl-1-oxo-2-[[(phenylmethoxy)carbonyl]amino]butyl]-2-phenyl-1,3-thiazolidin-4-ylcarboxamido]-2-oxo-4-phenyl-1,1,1-trifluorobutane (Compound No. 2-81)

IR(Film,cm$^{-1}$): 3306,1783,1713,1523,1322,1175,1126, 754.

(3RS)-3-[(2RS,4R)-3-[(2S)-2-(tert-Butoxycarbonyl)amino-3-methyl-1-oxobutyl]-2-phenyl-1,3-thiazolidin-4-ylcarboxamido]-2-oxo-4-phenyl-1,1,1-trifluorobutane (Compound No. 2-82)

Phenylmethyl (3S)-3-[(2RS,4R)-3-[(2S)-3-methyl-1-oxo-2-[[(phenylmethoxy)carbonyl]amino]butyl]-2-phenyl-1,3-thiazolidin-4-ylcarboxamido]-2-oxo-4-phenylbutyrate (Compound No. 2-83)

Phenylmethyl (3S)-3-[(2RS,4R)-3-[(2S)-2-(tert-butoxycarbonyl)amino-3-methyl-1-oxobutyl]-2-phenyl-1,3-thiazolidin-4-ylcarboxamido]-2-oxo-4-phenylbutyrate (Compound No. 2-84)

(2S)-2-[(2RS,4R)-3-[(2S)-3-Methyl-1-oxo-2-[[(phenylmethoxy)carbonyl]amino]butyl]-2-phenyl-1,3-thiazolidin-4-ylcarboxamido]-1-(2-oxazolyl)-1-oxo-3-phenylpropane (Compound No. 2-85)

(2S)-2-[(2RS,4R)-3-[(2S)-2-(tert-Butoxycarbonyl)amino-3-methyl-1-oxobutyl]-2-phenyl-1,3-thiazolidin-4-ylcarboxamido]-1-(2-oxazolyl)-1-oxo-3-phenylpropane (Compound No. 2-86)

(2S)-1-(2-Benzoxazolyl)-2-[(2RS,4R)-3-[(2S)-3-methyl-1-oxo-2-[[(phenylmethoxy)carbonyl]amino]butyl]-2-phenyl-1,3-thiazolidin-4-ylcarboxamido]-1-oxo-3-phenylpropane (Compound No. 2-87)

(2S)-1-(2-Benzoxazolyl)-2-[(2RS,4R)-3-[(2S)-2-(tert-butoxycarbonyl)amino-3-methyl-1-oxobutyl]-2-phenyl-1,3-thiazolidin-4-ylcarboxamido]-1-oxo-3-phenylpropane (Compound No. 2-88)

(2S)-2-[(2RS,4R)-3-[(2S)-3-Methyl-1-oxo-2-[[(phenylmethoxy)carbonyl]amino]butyl]-2-phenyl-1,3-thiazolidin-4-ylcarboxamido]-1-oxo-3-phenyl-1-(2-thiazolyl)propane (Compound No. 2-89)

(2S)-2-[(2RS,4R)-3-[(2S)-2-(tert-Butoxycarbonyl)amino-3-methyl-1-oxobutyl]-2-phenyl-1,3-thiazolidin-4-ylcarboxamido]-1-oxo-3-phenyl-1-(2-thiazolyl)propane (Compound No. 2-90)

(2S)-1-(2-Benzothiazolyl)-2-[(2RS,4R)-3-[(2S)-3-methyl-1-oxo-2-[[(phenylmethoxy)carbonyl]amino]butyl]-2-phenyl-1,3-thiazolidin-4-ylcarboxamido]-1-oxo-3-phenylpropane (Compound No. 2-91)

(2S)-1-(2-Benzothiazolyl)-2-[(2RS,4R)-3-[(2S)-2-(tert-butoxycarbonyl)amino-3-methyl-1-oxybutyl]-2-phenyl-1,3-thiazolidin-4-ylcarboxamido]-1-oxo-3-phenylpropane (Compound No. 2-92)

Isopropyl (3S)-3-[(3S,6RS,9R)-1-aza-2-oxo-3-[(phenylmethoxy)carbonyl]amino-7-thiabicyclo[4.3.0]nonan-9-ylcarboxamido]-2-oxo-4-phenylbutyrate (Compound No. 2-93)

IR(KBr,cm$^{-1}$): 3317,3031,2982,2936,2355,1664,1532, 1454,1375, 1250,1104.

Isopropyl (3S)-3-[(3R,6RS,9R)-1-aza-2-oxo-3-[(phenylmethoxy)carbonyl]amino-7-thiabicyclo[4.3.0]nonan-9-ylcarboxamido]-2-oxo-4-phenylbutyrate (Compound No. 2-94)

IR(Film,cm$^{-1}$): 3336,2928,1719,1520,1455,1420,1372, 1314,1266, 1210,1103,1016.

Isopropyl (3S)-3-[(3S,5RS,8R)-1-aza-2-oxo-3-[(phenylmethoxy)carbonyl]amino-6-thiabicyclo[3.3.0]nonan-8-ylcarboxamido]-2-oxo-4-phenylbutyrate (Compound No. 2-95)

Isopropyl (3S)-3-[(3S,7RS,10R)-1-aza-2-oxo-3-[(phenylmethoxy)carbonyl]amino-8-thiabicyclo[5.3.0]decan-10-ylcarboxamido]-2-oxo-4-phenylbutyrate (Compound No. 2-96)

IR(Film,cm$^{-1}$): 3338,3063,3029,2981,1720,1518,1453, 1408,1345, 1229,1181,1105.

Isopropyl (3S)-3-[(3R,7RS,10R)-1-aza-2-oxo-3-[(phenylmethoxy)carbonyl]amino-8-thiabicyclo[5.3.0]decan-10-ylcarboxamido]-2-oxo-4-phenylbutyrate (Compound No. 2-97)

$[\alpha]_D^{20}$ −81.3° (c=0.6, methanol); IR(KBr,cm$^{-1}$): 3317, 3030,2929,2853,1955,1722,1522,1453,1467, 1344,1105, 1064.

Isopropyl (3S)-3-[(3S,8RS,11R)-1-aza-2-oxo-3-[(phenylmethoxy)carbonyl]amino-9-thiabicyclo[6.3.0]undecan-11-ylcarboxamido]-2-oxo-4-phenylbutyrate (Compound No. 2-98)

Phenylmethyl (3S)-3-[(3S,6RS,9R)-1-aza-2-oxo-3-[(phenylmethoxy)carbonyl]amino-7-thiabicyclo[4.3.0]nonan-9-ylcarboxamido]-2-oxo-4-phenylbutyrate (Compound No. 2-99)

Phenylmethyl (3S)-3-[(3S,7RS,10R)-1-aza-2-oxo-3-[(phenylmethoxy)carbonyl]amino-8-thiabicyclo[5.3.0]decan-10-ylcarboxamido]-2-oxo-4-phenylbutyrate (Compound No. 2-100)

Example 3

Isopropyl (3S)-3-[(4R)-3-[(2S)-3-(5-imidazolyl)-1-oxo-2-[[(phenylmethoxy)carbonyl]amino]propyl]-1,3-Thiazolidin-4-ylcarboxamido]-2-oxo-4-phenylbutyrate (Compound No. 3-1)

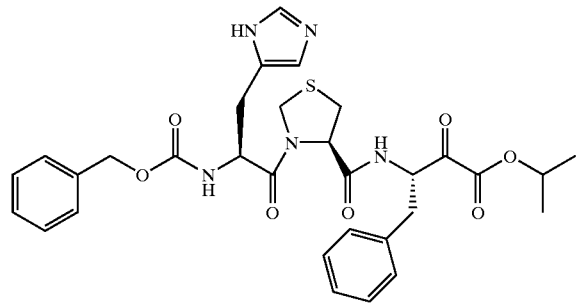

Trifluoroacetic acid (3.0 ml) is added to isopropyl (3S)-2-oxo-3-[(4R)-3-[(2S)-1-oxo-2-[(phenylmethoxy)carbonyl]amino-3-[1-(triphenylmethyl)imidazol-5-yl]propyl]-1,3-thiazolidin-4-ylcarboxamido]-4-phenylbutyrate (0.10 g), and the mixture is stirred for 2.5 hours. The reaction mixture is concentrated under reduced pressure, and the residue is dissolved in 0.1 N hydrochloric acid. This solution is washed with diethyl ether, and sodium hydrogencarbonate is added to the solution to basify it. The whole is extracted with ethyl acetate, and the extract is washed with saturated brine. The extract is dried over anhydrous magnesium sulfate and concentrated under reduced pressure to give 0.05 g of the titled compound.

IR(KBr,cm$^{-1}$): 3304,2982,1723,1654,1529,1435,1375, 1258,1144, 1102.

The following compounds are obtained by a method similar to Example 3.

Isopropyl (3S)-3-[(4R)-3-[(2S)-3-(3-indolyl)-1-oxo-2-[[(phenylmethoxy)carbonyl]amino]propyl]-1,3-thiazolidin-4-ylcarboxamido]-2-oxo-4-phenylbutyrate (Compound No. 3-2)

Isopropyl (3S)-3-[(2RS,4R)-3-[(2S)-3-(5-imidazolyl)-1-oxo-2-[[(phenylmethoxy)carbonyl]amino]propyl]-2-phenyl-1,3-thiazolidin-4-ylcarboxamido]-2-oxo-4-phenylbutyrate (Compound No. 3-3)

Isopropyl (3S)-3-[(2RS,4R)-3-[(2S)-3-(3-indolyl)-1-oxo-2-[[(phenylmethoxy)carbonyl]amino]propyl]-2-phenyl-1,3-thiazolidin-4-ylcarboxamido]-2-oxo-4-phenylbutyrate (Compound No. 3-4)

Example 4

Isopropyl (3S)-3-[(4R)-3-[(2S)-3-hydroxy-1-oxo-2-[[(phenylmethoxy)carbonyl]amino]propyl]-1,3-Thiazolidin-4-ylcarboxamido]-2-oxo- 4-phenylbutyrate (Compound No. 4-1)

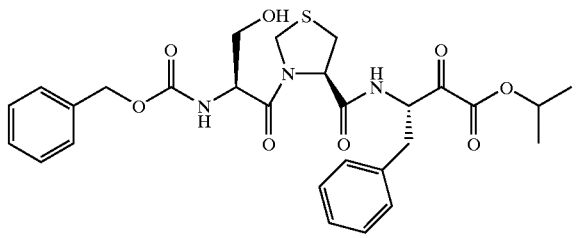

Trifluoroacetic acid (2.0 ml) is added to isopropyl (3S)-3-[(4R)-3-[(2S)-3-(tert-butoxy)-1-oxo-2-[[(phenylmethoxy)carbonyl]amino]propyl]-1,3-thiazolidin-4-ylcarboxamido]-2-oxo-4-phenylbutyrate (0.14 g) under ice cooling, and the mixture is stirred for 1.5 hours. The reaction mixture is concentrated under reduced pressure, an aqueous sodium hydrogencarbonate solution is added to the residue, and the whole is extracted with chloroform The extract is washed with saturated brine and dried over anhydrous magnesium sulfate. The extract is concentrated under reduced pressure, and the residue is purified by silica gel column chromatography to give 0.11 g of the titled compound.

IR(Film,cm$^{-1}$): 3309,1724,1654,1531,1428,1258,1102, 1059,1027, 752,699.

The following compound is obtained by a method similar to Example 4.

Isopropyl (3S)-3-[(2RS,4R)-3-[(2S)-3-hydroxy-1-oxo-2-[[(phenylmethoxy)carbonyl]amino]propyl]-2-phenyl-1,3-thiazolidin-4-ylcarboxamido]-2-oxo-4-phenylbutyrate (Compound No. 4-14)

Example 5

Isopropyl (3S)-3-[(4R)-3-[(2S)-3-carboxyl-1-oxo-2-[[(phenylmethoxy)carbonyl]amino]propyl]-1,3-Thiazolidin-4-ylcarboxymido]-2-oxo-4-phenylbutyrate (Compound No. 5-1)

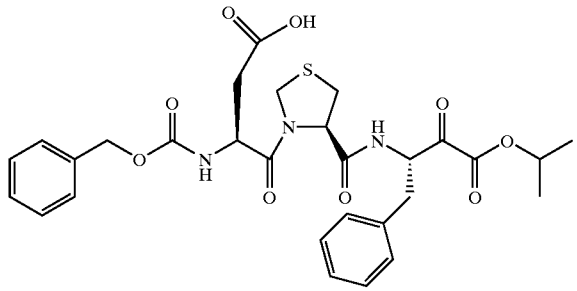

Trifluoroacetic acid (2.0 ml) is added to isopropyl (3S)-3-[(4R)-3-[(2S)-3-(tert-butoxycarbonyl)-1-oxo-2-[[(phenylmethoxy)carbonyl]amino]propyl]-1,3-thiazolidin-4-ylcarboxamido]-2-oxo-4-phenylbutyrate (0.14 g), and the is stirred for 1.5 hours. The reaction mixture is concentrated under reduced pressure, an aqueous sodium hydrogencarbonate solution is added to the residue, and the whole is washed with water. To this mixture is added 1 N hydrochloric acid to acidify it, and the whole is extracted with ethyl acetate. The extract is dried over anhydrous magnesium sulfate and concentrated under reduced pressure. The residue is purified by silica gel column chromatography to give the titled compound.

The following compound is obtained by a method similar to Example 5.

Isopropyl (3S)-3-[(2RS,4R)-3-[(2S)-3-carboxyl-1-oxo-2-[[(phenylmethoxy)carbonyl]amino]propyl]-1,3-thiazolidin-4-ylcarboxamido]-2-oxo-4-phenylbutyrate (Compound No. 5-2)

Example 6

Isopropyl (3S)-3-[(4R)-3-[(2S)-2-[[N-(2-aminoethyl)-N-methylamino]carbonyl]amino-3-methyl-1-oxobutyl]-1,3-Thiazolidin 4-ylcarboxamido]-2-oxo-4-phenylbutyrate hydrochloride (Compound No. 6-1)

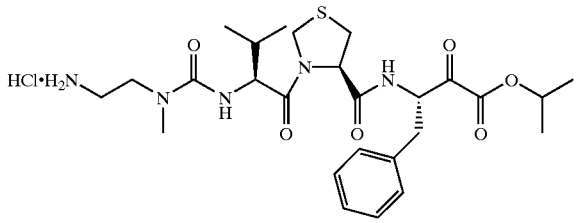

A 4.6 N hydrogen chloride/ethyl acetate solution (0.5 ml) is added to isopropyl (3S)-3-[(4R)-3-[(2S)-2-[[N-[2-[(tert-butoxycarbonyl)amino]ethyl]-N-methylamino]carbonyl]amino-3-methyl-1-oxobutyl]-1,3-thiazolidin-4-ylcarboxamido]-2-oxo-4-phenylbutyrate (25 mg), and the mixture is stirred for two hours. The reaction mixture is concentrated under reduced pressure to give 21 mg of the titled compound.

IR(Film,cm$^{-1}$): 3300,2979,2360,1692,1627,1529,1467, 1373,1269, 1201,1092,1028.

The following compound is obtained by a method similar to Example 6.

Isopropyl (3S)-3-[(2RS,4R)-3-[(2S)-2-[[N-(2-aminoethyl)-N-methylamino]carbonyl]amino]-3-methyl-1-oxobutyl]-2-phenyl-1,3-thiazolidin-4-ylcarboxamido]-2-oxo-4-phenylbutyrate hydrochloride (Compound No. 6-2)
mp 90.0° C.

Example 7
Isopropyl (3S)-3-[(4R)-3-[(2S)-3-methyl-2-[[4-(methylamino)piperidino]carbonyl]amino-1-oxobutyl]-1,3-Thiazolidin-4-ylcarboxamido]-2-oxo-4-phenylbutyrate hydrochloride (Compound No. 7-1)

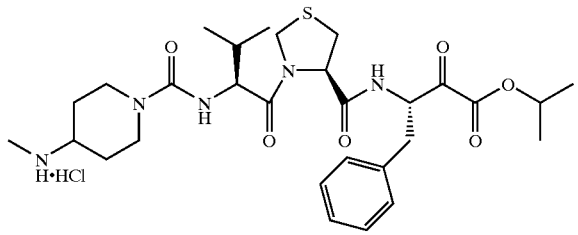

Trifluoroacetic acid (2.0 ml) is added to isopropyl (3S)-3-[(4R)- 3-[(2S)-2-[[4-[N-(tert-butoxycarbonyl)-N-methylamino]-piperidino]carbonyl]amino-3-1-oxobutyl]-1,3-thiazolidin-4-ylcarboxamido]-2-oxo-4-phenylbutyrate (0.10 g), and the mixture is stirred for 20 minutes. The reaction mixture is concentrated under reduced pressure, the residue is dissolved in 2-propanol (3.0 ml), and 1 N hydrochloric acid is added to the solution. The reaction mixture is concentrated under reduced pressure, and the residue is dried in a desiccator. Diethyl ether is added to the residue to crystallize it to give 0.09 g of the titled compound.

The following compound is obtained by a method similar to Example 7.
Isopropyl (3S)-3-[(2RS,4R)-3-[(2S)-3-methyl-2-[[4-(methylamino)piperidino]carbonyl]amino-1-oxobutyl]-2-phenyl-1,3-thiazolidin-4-ylcarboxamido]-2-oxo-4-phenylbutyrate hydrochloride (Compound No. 7-2)
mp 106.0–115.0° C. IR(KBr,cm$^{-1}$): 3306,2967,2467, 1729,1631,1528,1376,1255,1181, 1102.

Formulation

General formulation examples of oral preparations and eyedrops using the present compounds are shown below.

| 1) Tablet | |
|---|---|
| Formulation 1 in 100 mg | |
| Present compound | 1 mg |
| Lactose | 66.4 mg |
| Cornstarch | 20 mg |
| Calcium carboxymethylcellulose | 6 mg |
| Hydroxypropylcellulose | 4 mg |
| Magnesium stearate | 0.6 mg |

Tablets according to the formulation as above are coated with 2 mg/tablet of a coating agent (this is a conventional coating agent such as hydroxypropylmethylcellulose, macrogol or silicone resin) to obtain desired coated tablets. (The same is applied to tablets mentioned below.) Desired tablets can be obtained by changing the amounts of the present compound and the additives appropriately.

| 2) Capsule | |
|---|---|
| Formulation 1 in 150 mg | |
| Present compound | 5 mg |
| Lactose | 145 mg |

Desired capsules can be obtained by changing the mixing ratio of the present compound to lactose appropriately.

| 3) Eyedrops | |
|---|---|
| Formulation 1 in 10 ml | |
| Present compound | 1 mg |
| Concentrated glycerin | 250 mg |
| Polysorbate 80 | 200 mg |
| Sodium dihydrogenphosphate dihydrate | 20 mg |
| 1 N Sodium hydroxide | q.s. |
| 1 N Hydrochloric acid | q.s. |
| Sterile purified water | q.s. |

Desired eyedrops can be obtained by changing the amounts of the present compound and the additives appropriately.

Pharmacological Test
1) Chymase Inhibitory Effect

Chymase (enzyme) causes angiotensin I (substrate) to liberate a dipeptide (His-Leu) by the enzyme reaction with the substrate. It was reported that an enzymatic activity of chymase can be measured by measuring fluorescence intensity of the resulting peptide (Biochem. Biophys. Res. Com., 149 (3) 1186 (1987)). Since drugs having chymase inhibitory activities suppress this liberation of the dipeptide, the chymase inhibitory activities of the drugs can be measured by measuring fluorescence intensity. In the present pharmacological test, chymase inhibitory effects of the present compounds were studied by using chymase extracted from a dog cardiac tissue (J. Biol. Chem., 265 (36), 22348 (1990)).

Experimental Method
[1. Preparation of Chymase Enzyme Solution]
1. A beagle is killed by drawing blood under Nembutal anesthesia, a heart is enucleated, and left ventricle is separated.
2. This left ventricle is finely minced, and the tissue weight is measured.
3. A 0.02 M Tris-HCl buffer (pH 7.4) is added to the tissue in an amount of 10 times by volume the tissue weight. This mixture is homogenized at 8,000 rpm for 20 seconds and then centrifuged at 4° C. and 21,000 rpm for 30 minutes, and the resulting supernatant is discarded.
4. The same procedure as the above 3 is repeated twice for the residue. Then, a 0.02 M Tris-HCl buffer (pH 7.4) containing 1% Triton X-100 and 0.01 M potassium chloride is added to the residue in an amount of 10 times by volume the amount of the residue. This mixture is homogenized at 8,000 rpm for 20 seconds, then incubated at 4° C. for one hour and centrifuged at 21,000 rpm for 30 minutes, and the supernatant is discarded.
5. A 0.02 M Tris-HCl buffer (pH 7.4) containing 1% Triton X-100 and 0.5 M potassium chloride is added to the residue in an amount of 10 times by volume the amount of the residue. This mixture is homogenized at 8,000 rpm for 20 seconds, then incubated at 4° C. for one hour and centrifuged at 21,000 rpm for 30 minutes, and the supernatant is discarded.

6. A 0.02 M Tris-HCl buffer (pH 7.4) containing 1% Triton X-100 and 2.0 M potassium chloride is added to the residue in an amount of 10 times the amount of the residue. This mixture is homogenized at 8,000 rpm for 20 seconds, then incubated at 4° C. for one hour and centrifuged at 21,000 rpm for 30 minutes. The obtained supernatant is used as a chymase enzyme solution.

[2. Preparation of Reaction Buffer]

Tris-HCl and disodium ethylenediaminetetraacetate are dissolved in water so that their concentrations are 92.3 mM and 12.0 mM respectively to prepare a reaction buffer adjusted to pH 8.

[3. Preparation of Substrate Solution]

Angiotensin I is dissolved in water to prepare a 1.54 mM substrate solution.

[4. Preparation of Test compound Solution]

A test compound is dissolved in dimethyl sulfoxide to prepare $3.0 \times 10^{-3}$ M, $3.0 \times 10^{-4}$ M, $3.0 \times 10^{-5}$ M and $3.0 \times 10^{-6}$ M test com solutions.

[5. Measurement of Chymase Enzymatic Activity]

1. The reaction buffer (32.5 μl), the substrate solution (75.0 μl), the chymase enzyme solution (37.5 μl) and the test compound solution (5 μl) are mixed.
2. The obtained mixture is incubated at 37° C. for one hour.
3. To the mixture is added 15% trichloroacetic acid (225 μl), and the whole is centrifuged at 4° C. and 14,000 rpm for five minutes.
4. The supernatant is taken out. A 1% orthophthalaldehyde/methanol solution (165 μl) is added to 300 μl of this supernatant, and the whole is stirred and allowed to stand at room temperature for 10 minutes.
5. 1.5 M Hydrochloric acid (300 μl) is added to the resulting mixture, and the whole is stirred and centrifuged at 4° C. and 14,000 rpm for two minutes.
6. The supernatant is taken out and irradiated with light having a wavelength of 340 nm, and fluorescence intensity is measured at a wavelength of 455 nm.

The blank of this test is defined as follows. The same procedures as in the above 1 to 6 are repeated provided that a 20 mM Tris-HCl buffer (pH 7.4, 37.5 μl) containing 1% Triton X-100 and 2.0 M potassium chloride is used instead of the chymase enzyme solution (37.5 μl), and dimethyl sulfoxide (5 μl) is used instead of the test compound solution (5 μl) in the above 1. The obtained absorbance is the blank value. The control of this test is defined as follows. The same procedures as in the above 1 to 6 are repeated provided that dimethyl sulfoxide (5 μl) is used instead of the test compound solution (5 μl) in the above 1. The obtained absorbance is the control value.

[6. Calculation of Chymase Inhibition Rate]

Chymase inhibition rates of the test compounds are calculated by the following equation from the measured fluorescence intensity.

Chymase inhibition rate (%)=[1−(Fluorescence intensity in using test compound solution−Blank fluorescence intensity)/(Control fluorescence intensity−Blank fluorescence intensity)]×100

[7. Results]

Concentrations required to inhibit a chymase enzymatic activity by 50% were calculated from the obtained chymase inhibition rates of the test compounds.

As examples of test results, Table 1 shows concentrations of the following test compounds (Compound Nos. 2-1, 2-19, 2-20, 2-21, 2-25, 2-26, 2-37 and 6-2) required to inhibit the chymase enzymatic activity by 50%, i.e., $IC_{50}$.

TABLE 1

| Test compound | $IC_{50}$ (M) |
| --- | --- |
| Compound No. 2-1 | $4.7 \times 10^{-8}$ |
| Compound No. 2-19 | $5.6 \times 10^{-8}$ |
| Compound No. 2-20 | $4.4 \times 10^{-8}$ |
| Compound No. 2-21 | $2.6 \times 10^{-8}$ |
| Compound No. 2-25 | $3.1 \times 10^{-8}$ |
| Compound No. 2-26 | $1.2 \times 10^{-8}$ |
| Compound No. 2-37 | $6.6 \times 10^{-8}$ |
| Compound No. 6-2 | $5.7 \times 10^{-8}$ |

As shown in Table 1, the present compounds exhibited excellent chymase inhibition effects.

From the above-mentioned results, the present compounds are expected to be useful as drugs, particularly to be effective in treating various diseases originating from chymase such as cardiac infarction, heart failure, blood-vessel restenosis after PTCA, hypertension, diabetes complication, allergic diseases and asthma.

Industrial Applicability

The present invention provides novel thiazolidine derivatives which are useful as drugs such as chymase inhibitors.

What is claimed is:

1. A compound of formula [I] or a salt thereof,

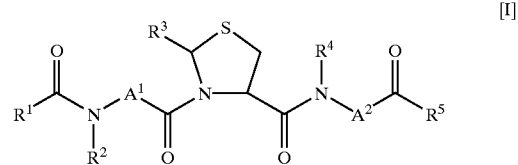

[I]

wherein $R^1$ is lower alkyl, lower alkoxy, lower alkoxy-lower alkyl, phenyl, phenyl-lower alkyl, phenyl-lower alkoxy, phenoxy, phenoxy-lower alkyl, amino, lower alkylamino or a nonaromatic heterocycle, $R^2$ is hydrogen or lower alkyl or $R^2$ joins with $A^1$ through the carbon or sulfur to form a nonaromatic heterocycle, $R^3$ is hydrogen, lower alkyl or phenyl or $R^3$ joins with $A^1$ through the carbon to form a nonaromatic heterocycle, $R^4$ is hydrogen or lower alkyl, $R^5$ is lower alkyl, halogeno-lower alkyl, hydroxy, lower alkoxy, phenyl, phenyl-lower alkoxy, phenoxy, carboxyl, lower alkoxycarbonyl, phenyl-lower alkoxycarbonyl or an aromatic heterocycle, $A^1$ is lower alkylene, wherein the lower alkylene is unsubstituted or substituted by hydroxy, lower alkoxy, phenyl, phenoxy, carboxyl, lower alkoxycarbonyl, phenyl-lower alkoxycarbonyl or an aromatic heterocycle, provided that $A^1$ is not CH(OH), $A^2$ is lower alkylene substituted by phenyl, each said nonaromatic heterocycle is unsubstituted or substituted by lower alkyl, phenyl, phenyl-lower alkyl, amino, lower alkylamino or phenyl-lower alkylamino, and each said nonaromatic heterocycle is selected from the group consisting of pyrrolidine, piperidine, homopiperidine, octahydroazocine, pyrroline, piperazine, imidazolidine, imidazoline, pyrazolidine, pyrazoline, oxazolidine and thiazolidine, said aromatic heterocycle is selected from the group consisting of pyrrole, indole, isoindole, imidazole, pyrazole, oxazole, isoxazole, benzoxazole, thiazole, isothiazole, benzothiazole, pyridine, quinoline and pyrazine, each phenyl ring of said phenyl, said phenyl-lower alkyl, said phenyl-lower alkoxy, said phenoxy, said phenoxy-lower alkyl and said phenyl-lower alkoxycarbonyl is unsubstituted or substituted by halogen, lower alkyl, hydroxy, lower alkoxy, phenyl, phenoxy, carboxyl, lower alkoxycarbonyl, amino, lower alkylamino, nitro or cyano, each lower alkyl moiety of said lower alkylamino is unsubstituted or substituted by phenyl, amino or lower alkylamino.

2. The compound of claim 1 or a salt thereof, wherein $R^1$ is selected from the group consisting of lower alkyl, lower alkoxy, lower alkoxy-lower alkyl, phenyl, phenyl-lower alkyl, phenyl-lower alkoxy, phenoxy, phenoxy-lower alkyl, amino, lower alkylamino, piperidine and piperazine, wherein each phenyl ring of said phenyl, said phenyl-lower alkyl, said phenyl-lower alkoxy, said phenoxy and said phenoxy-lower alkyl is unsubstituted or substituted by a substituent selected from the group consisting of halogen, lower alkyl, lower alkoxy and nitro, wherein the lower alkyl moiety of the lower alkylamino is unsubstituted or substituted by a substituent selected from the group consisting of phenyl and amino, wherein the piperidine is unsubstituted or substituted by a substituent selected from the group consisting of lower alkyl and lower alkylamino, and wherein the piperidine is unsubstituted or substituted by a substituent selected from the group consisting of lower alkyl and lower alkylamino;

$R^2$ is hydrogen or lower alkyl or $R^2$ joins with $A^1$ through the carbon or sulfur to form a ring selected from the group consisting of pyrrolidine and thiazolidine;

$R^3$ is hydrogen or phenyl, wherein the phenyl is unsubstituted or substituted by a substituent selected from the group consisting of halogen, lower alkyl, lower alkoxy and nitro or $R^3$ joins with $A^1$ through carbon to form a ring selected from the group consisting of pyrrolidine, piperidine, homopiperazine and octahydroazocine;

$R^4$ is hydrogen;

$R^5$ is selected from the group consisting of lower alkyl, halogeno-lower alkyl, lower alkoxycarbonyl, phenyl-lower alkoxycarbonyl, oxazole, benzoxazole, thiazole and benzothiazole; and $A^1$ is lower alkylene which is unsubstituted or substituted by a substituent selected from the group consisting of hydroxy, lower alkoxy, phenyl, carboxyl, lower alkoxycarbonyl, indole and imidazole.

3. The compound of claim 1 or a salt thereof, wherein $R^1$ is selected from the group consisting of lower alkoxy, lower alkoxy-lower alkyl, phenyl-lower alkoxy, phenoxy-lower alkyl, lower alkylamino and piperidine, wherein the phenyl ring of the phenyl-lower alkoxy is unsubstituted or substituted by lower alkoxy, the lower alkyl moiety of the lower alkylamino is unsubstituted or substituted by phenyl or amino, and the piperidine is unsubstituted or substituted by lower alkylamino;

$R^2$ is hydrogen or $R^2$ joins with $A^1$ through the carbon to form pyrrolidine;

$R^3$ is hydrogen or phenyl or $R^3$ joins with $A^1$ through the carbon to form a ring selected from the group consisting of piperidine and homopiperazine;

$R^4$ is hydrogen;

$R^5$ is lower alkoxycarbonyl or phenyl-lower alkoxycarbonyl; and $A^1$ is lower alkylene which is unsubstituted or substituted by hydroxy or indole.

4. A compound of claim 1 or a salt thereof, wherein the nitrogen atom of at least one of the amino, the lower alkylamino, the nonaromatic heterocycle and the aromatic heterocycle is protected with a protecting group selected from the group consisting of acyl, substituted lower alkyl and substituted sulfonyl.

5. The compound of claim 1 or a salt thereof, wherein $R^1$ is selected from the group consisting of methyl, tert-butoxy, methoxymethyl, phenylmethyl, phenylethyl, phenylmethoxy, (4-chlorophenyl)methoxy, (4-methylphenyl)methoxy, (4-methoxyphenyl)methoxy, (4-nitrophenyl)methoxy, phenoxy, phenoxymethyl, ethylmethylamino, N-methyl-N-phenylmethylamino, N-(2-aminoethyl)-N-methylamino, 4-(methylamino)piperidino and 4-methylpiperazino;

$R^2$ is hydrogen or methyl or $R^2$ joins with $A^1$ through the carbon or sulfur to form a ring selected from the group consisting of pyrrolidine and thiazolidine;

$R^3$ is selected from the group consisting of hydrogen, phenyl, 4-chlorophenyl, 4-methylphenyl, 4-methoxyphenyl and 4-nitrophenyl or $R^3$ joins with $A^1$ through the carbon to form a ring selected from the group consisting of pyrrolidine, piperidine, homopiperazine and octahydroazocine;

$R^4$ is hydrogen;

$R^5$ is selected from the group consisting of trifluoromethyl, isopropoxycarbonyl, benzyloxycarbonyl, oxazolyl, benzoxazolyl, thiazolyl and benzothiazolyl;

$A^1$ is selected from the group consisting of methylene, methylmethylene, ethylmethylene, isopropylmethylene, isobutylmethylene, sec-butylmethylene, tert-butylmethylene, phenylmethylene, phenylmethylmethylene, (4-phenylbutyl)methylene, (4-hydroxyphenyl)methylmethylene, [(3-indolyl)methyl]methylene, [(5-imidazolyl)methyl]methylene, (hydroxymethyl)methylene, (tert-butoxymethyl)methylene and (carboxylmethyl)methylene; and $A^2$ is methylene or phenylmethylmethylene.

6. The compound of claim 1 or a salt thereof, wherein $R^1$ is selected from the group consisting of tert-butoxy, methoxymethyl, phenylmethoxy, (4-methoxyphenyl)methoxy, phenoxymethyl, ethylmethylamino, N-methyl-N-(phenylmethyl) amino, N-(2-ethylamino)N-methylamino and (4-methylamino)piperidino;

$R^2$ is hydrogen or $R^2$ joins with $A^1$ through the carbon to form pyrrolidine;

$R^3$ is hydrogen or phenyl or $R^3$ joins with $A^1$ through the carbon to form a ring selected from the group consisting of piperidine and homopiperazine;

$R^4$ is hydrogen;

$R^5$ is selected from the group consisting of isopropoxycarbonyl and (phenylmethoxy)carbonyl;

$A^1$ is selected from the group consisting of methylene, methylmethylene, ethylmethylene, isopropylmethylene, isobutylmethylene, sec-butylmethylene, tert-butylmethylene, [5-imidazolyl)

methyl]methylene, (hydroxymethyl)methylene and (tert-butoxymethyl)methylene; and A² is phenylmethylmethylene.

7. A compound of formula [II] or a salt thereof,

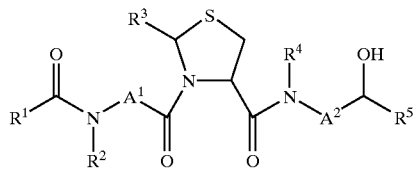

[II]

wherein R¹ is lower alkyl, lower alkoxy, lower alkoxy-lower alkyl, phenyl, phenyl-lower alkyl, phenyl-lower alkoxy, phenoxy, phenoxy-lower alkyl, amino, lower alkylamino or a nonaromatic heterocycle, R² is hydrogen or lower alkyl or R² joins with A¹ through the carbon or sulfur to form a nonaromatic heterocycle, R³ is hydrogen, lower alkyl or phenyl or R³ joins with A¹ through the carbon to form a nonaromatic heterocycle, R⁴ is hydrogen or lower alkyl, R⁵ is lower alkyl, halogeno-lower alkyl, hydroxy, lower alkoxy, phenyl, phenyl-lower alkoxy, phenoxy, carboxyl, lower alkoxycarbonyl, phenyl-lower alkoxycarbonyl or an aromatic heterocycle, A¹ is lower alkylene, wherein the lower alkylene is unsubstituted or substituted by hydroxy, lower alkoxy, phenyl, phenoxy, carboxyl, lower alkoxycarbonyl, phenyl-lower alkoxycarbonyl or an aromatic heterocycle, provided that A¹ is not CH(OH), A² is lower alkylene substituted by phenyl, each said nonaromatic heterocycle is unsubstituted or substituted by lower alkyl, phenyl, phenyl-lower alkyl, amino, lower alkylamino, phenyl-lower alkylamino or lower alkoxycarbonylamino, and each said nonaromatic heterocycle is selected from the group consisting of pyrolidine, piperidine, homopiperidine, octahydroazocine, pyrroline, piperazine, imidazolidine, imidazoline, pyrazolidine, pyrazoline, oxazolidine and thiazolidine, said aromatic heterocycle is selected from pyrrole, indole, isoindole, imidazole, pyrazole, oxazole, isoxazole, benzoxazole, thiazole, isothiazole, benzothiazole, pyridine, quinoline and pyrazine, each phenyl ring of said phenyl, said phenyl-lower alkyl, said phenyl-lower alkoxy, said phenoxy, said phenoxy-lower alkyl and said phenyl-lower alkoxycarbonyl is unsubstituted or substituted by halogen, lower alkyl, hydroxy, lower alkoxy, phenyl, phenoxy, carboxyl, lower alkoxycarbonyl, amino, lower alkylamino, nitro or cyano, each lower alkyl moiety of said lower alkylamino is unsubstituted or substituted by phenyl, amino, lower alkylamino or lower alkoxycarbonylamino.

8. A compound of claim 2 or a salt thereof, wherein at least one of the amino and the lower alkylamino is protected with a protecting group selected from the group consisting of acyl, substituted lower alkyl and substituted sulfonyl.

9. A compound of claim 3 or a salt thereof, wherein at least one of the amino and the lower alkylamino is protected with a protecting group selected from the group consisting of acyl, substituted lower alkyl and substituted sulfonyl.

10. A compound of claim 4, wherein the protecting group is selected from the group consisting of formyl, acetyl, trichloroacetyl, trifuloroacetyl, methoxycarbonyl, isobutoxycarbonyl, tert-butoxycarbonyl, 2,2,2-trichloroethoxycarbonyl, benzoyl, benzyloxycarbonyl, 4-bromobenzyloxycarbonyl, 2,4,6-trimethylbenzyloxycarbonyl, 4-methoxybenzyloxycarbanyl, 4-nitrobenzyloxycarbonyl, phenoxycarbonyl, benzyl, 2-nitrobenzyl, benzyloxymethyl, trityl, methanesulfonyl, benzenesulfonyl and toluenesulfonyl.

11. A pharmaceutical composition for inhibiting chymase comprising a pharmaceutically effective amount of the compound of claim 1 or a pharmaceutically acceptable salt thereof as an active ingredient in combination with a pharmaceutically acceptable carrier.

12. A method for inhibiting chymase comprising administering to a patient in need thereof a pharmaceutically effective amount of the compound of claim 1 or a pharmaceutically acceptable salt thereof.

* * * * *